United States Patent
Hoary et al.

(10) Patent No.: US 8,182,500 B2
(45) Date of Patent: May 22, 2012

(54) VEIN STRIPPING DEVICE

(75) Inventors: Marto Hoary, Galway (IE); Sherif Sultan, Galway (IE); Colm Anthony McCormack, County Kildare (IE)

(73) Assignee: Embricon Limited, Galway (IE)

( * ) Notice: Subject to any disclaimer, the term of this patent is extended or adjusted under 35 U.S.C. 154(b) by 139 days.

(21) Appl. No.: 12/457,049

(22) Filed: May 29, 2009

(65) Prior Publication Data

US 2009/0299331 A1 Dec. 3, 2009

Related U.S. Application Data

(60) Provisional application No. 61/136,622, filed on Sep. 19, 2008, provisional application No. 61/202,428, filed on Feb. 27, 2009.

(30) Foreign Application Priority Data

May 29, 2008 (IE) .................................... 2008/0430

(51) Int. Cl.
*A61B 17/22* (2006.01)

(52) U.S. Cl. ....................................... 606/159; 604/523

(58) Field of Classification Search .................. 606/159, 606/167, 170; 600/36, 114; 604/177, 187, 604/523
See application file for complete search history.

(56) References Cited

U.S. PATENT DOCUMENTS

| | | | |
|---|---|---|---|
| 1,644,919 A | 10/1927 | Hayes | |
| 3,568,677 A | 3/1971 | Nolan | |
| 3,955,579 A | 5/1976 | Bridgman | |
| 5,112,312 A * | 5/1992 | Luther | 604/177 |
| 5,792,155 A | 8/1998 | Van Cleef | |
| 5,893,858 A * | 4/1999 | Spitz | 606/170 |
| 6,652,549 B1 | 11/2003 | Welten | |
| 2003/0125759 A1 | 7/2003 | Mirizzi | |
| 2004/0087967 A1 | 5/2004 | Schur | |

FOREIGN PATENT DOCUMENTS

| | | |
|---|---|---|
| CH | 632659 | 12/1978 |
| FR | 2 622 805 | 5/1989 |
| WO | 87/01273 | 3/1987 |
| WO | 94/21177 | 9/1994 |
| WO | WO 94/21177 | 9/1994 |
| WO | 00/42918 | 7/2000 |
| WO | 2006/023203 | 3/2006 |
| WO | WO 2006/023203 | 3/2006 |
| WO | 2007/081842 | 7/2007 |
| WO | WO 2007/081842 | 7/2007 |

* cited by examiner

*Primary Examiner* — Victor Nguyen
(74) *Attorney, Agent, or Firm* — Jacobson Holman PLLC

(57) ABSTRACT

A vein stripping device 1 includes a catheter 2 for insertion into a vein 10 to be removed. The catheter 2 has a proximal region 3 adjacent a proximal end 4 of the catheter 2 and a distal region 5 adjacent a distal end 6 of the catheter 2. The catheter 2 is open at the distal end for passage of blood through the catheter from the distal end. The catheter 2 has a plurality of vein grippers 15, 16 at least along the distal region 5 for gripping a length of the vein 10 to the catheter 2. The vein grippers include a plurality of holes and/or gripping features 15, 16 spaced-apart along the wall of the catheter 2.

37 Claims, 52 Drawing Sheets

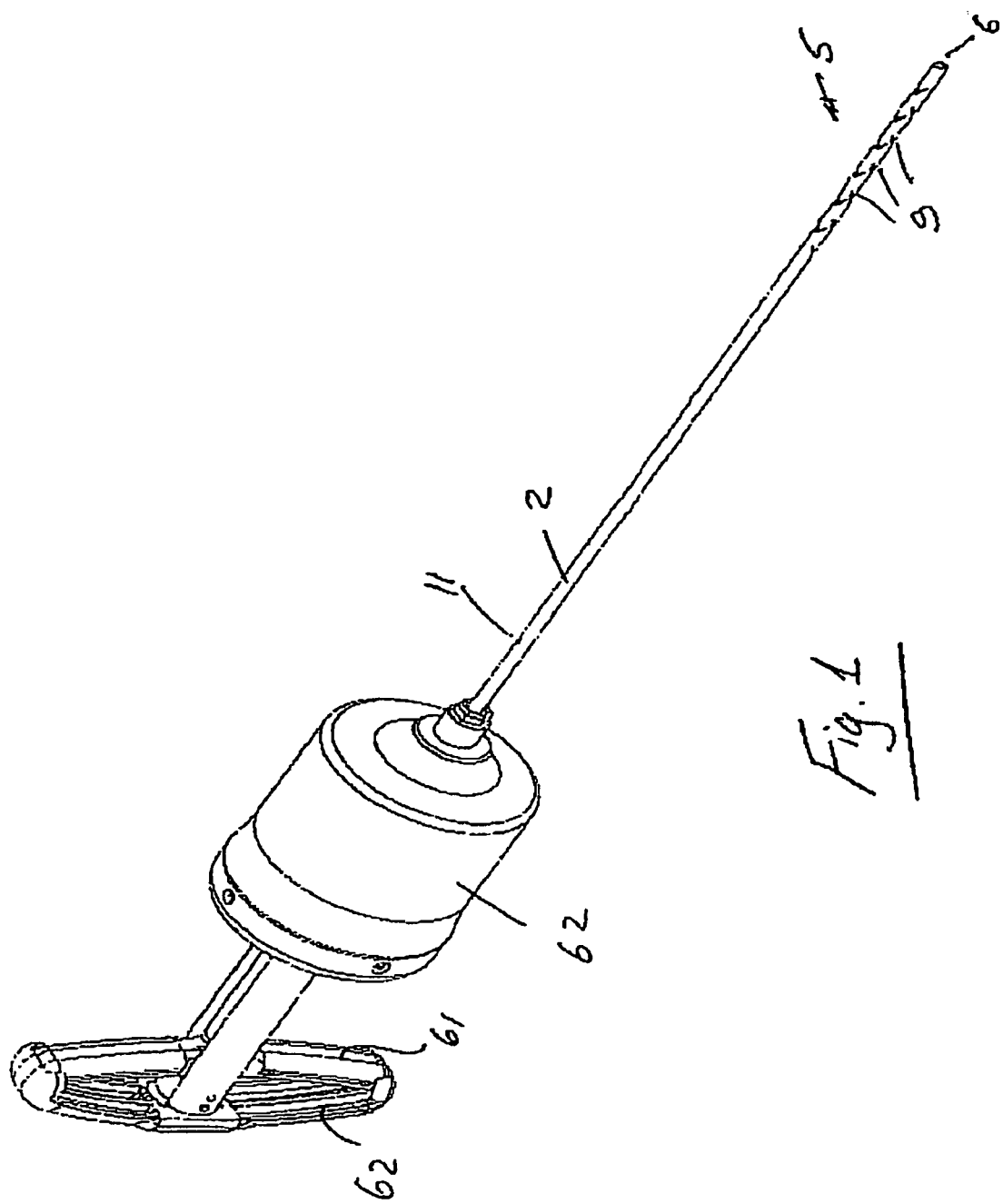

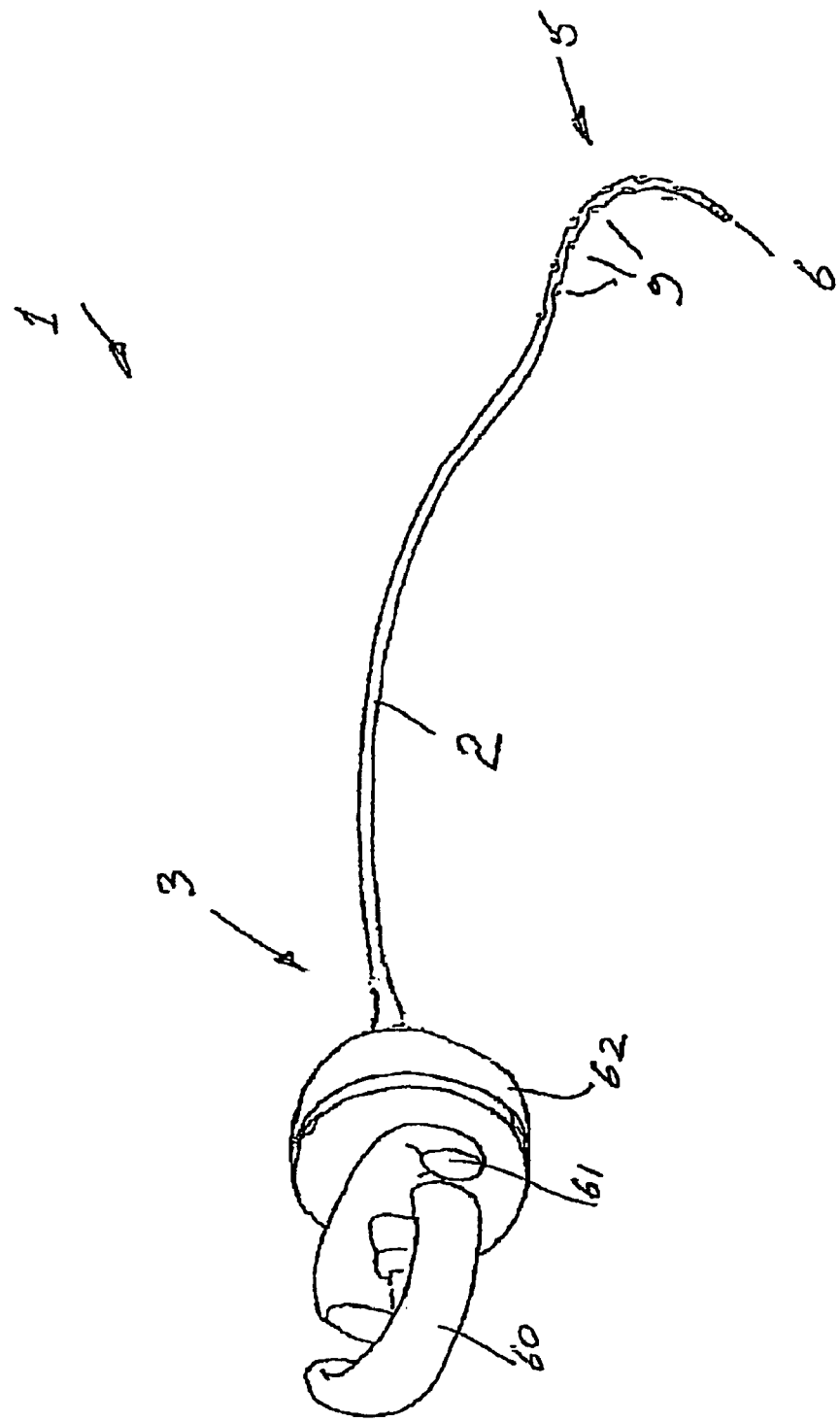

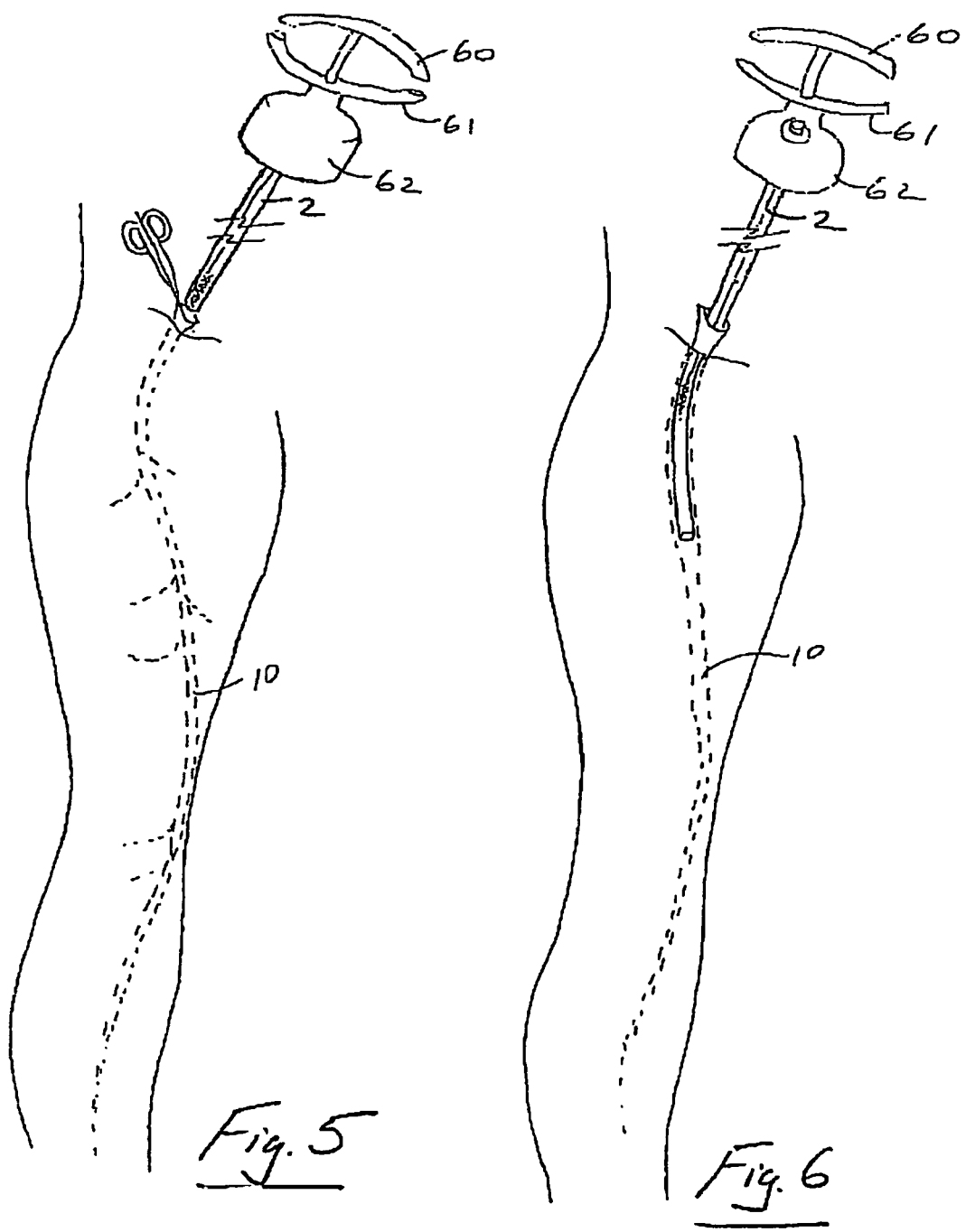

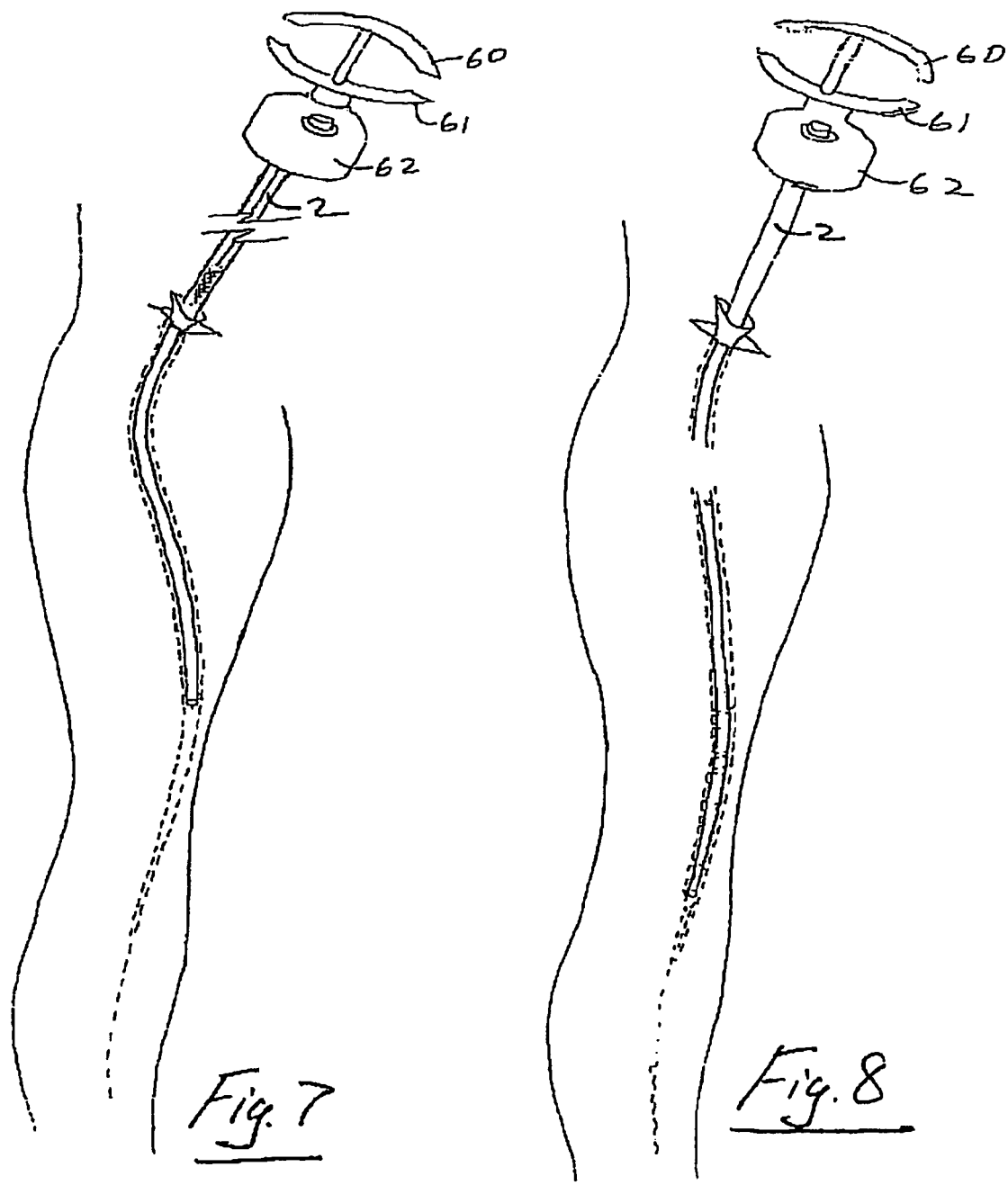

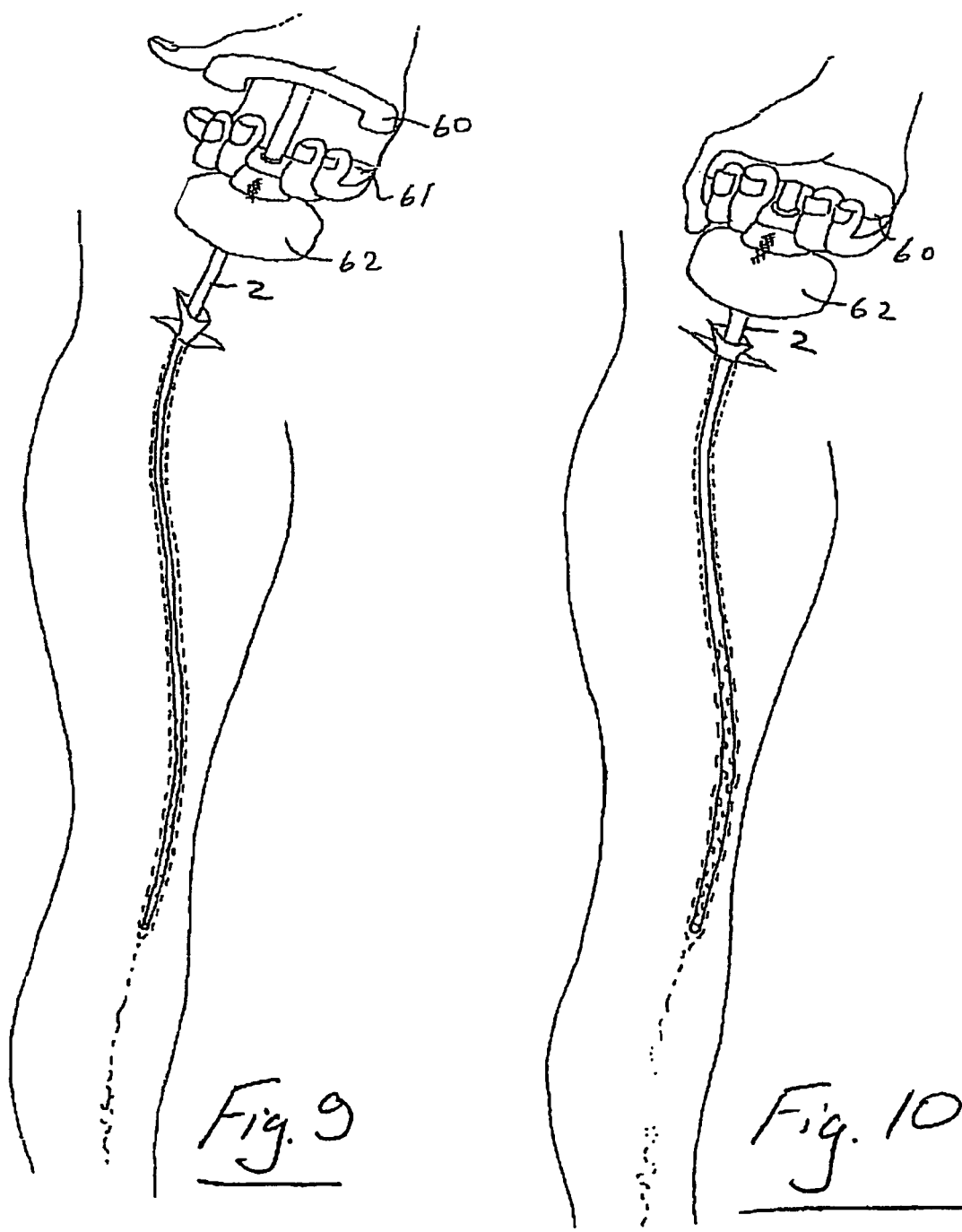

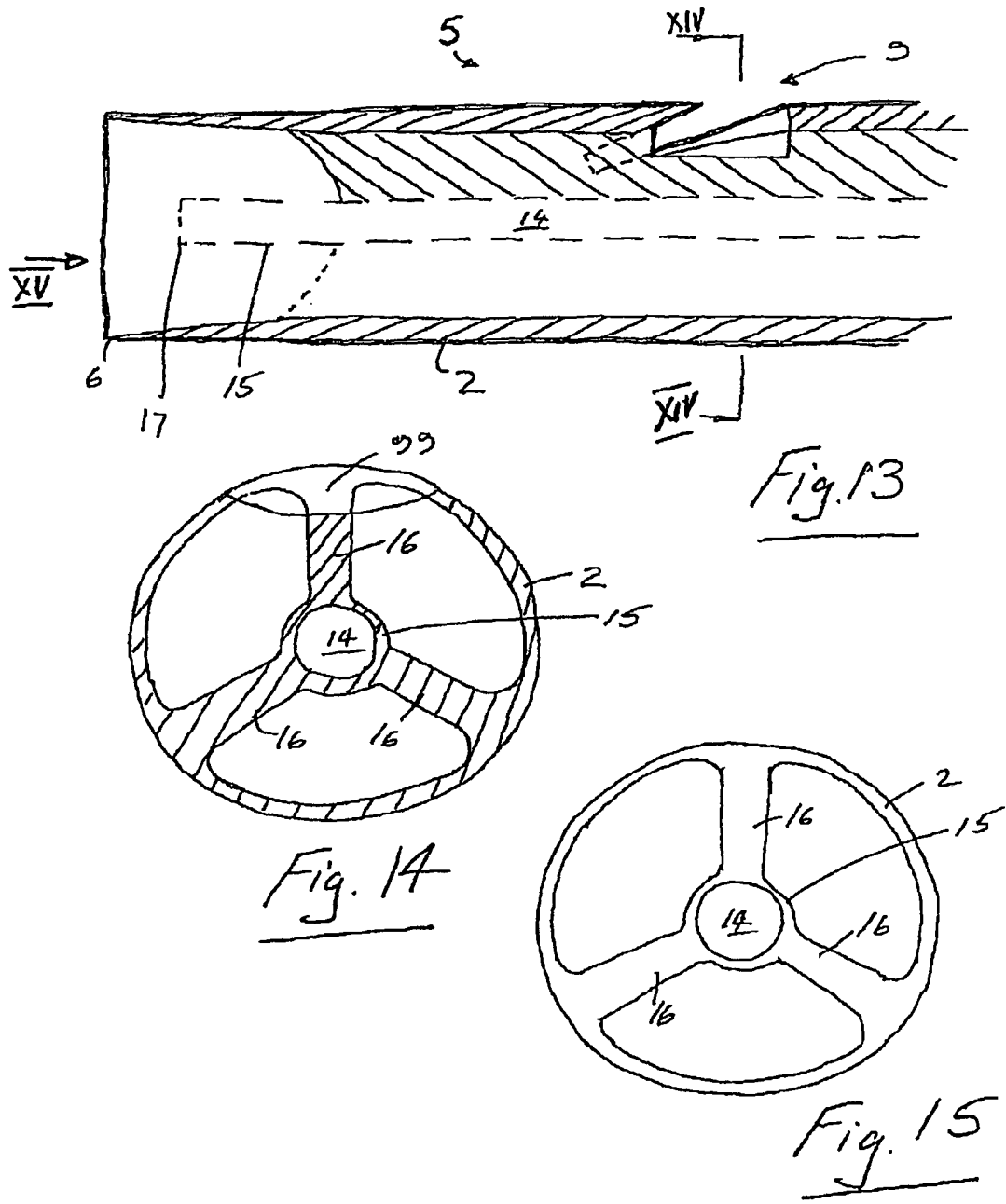

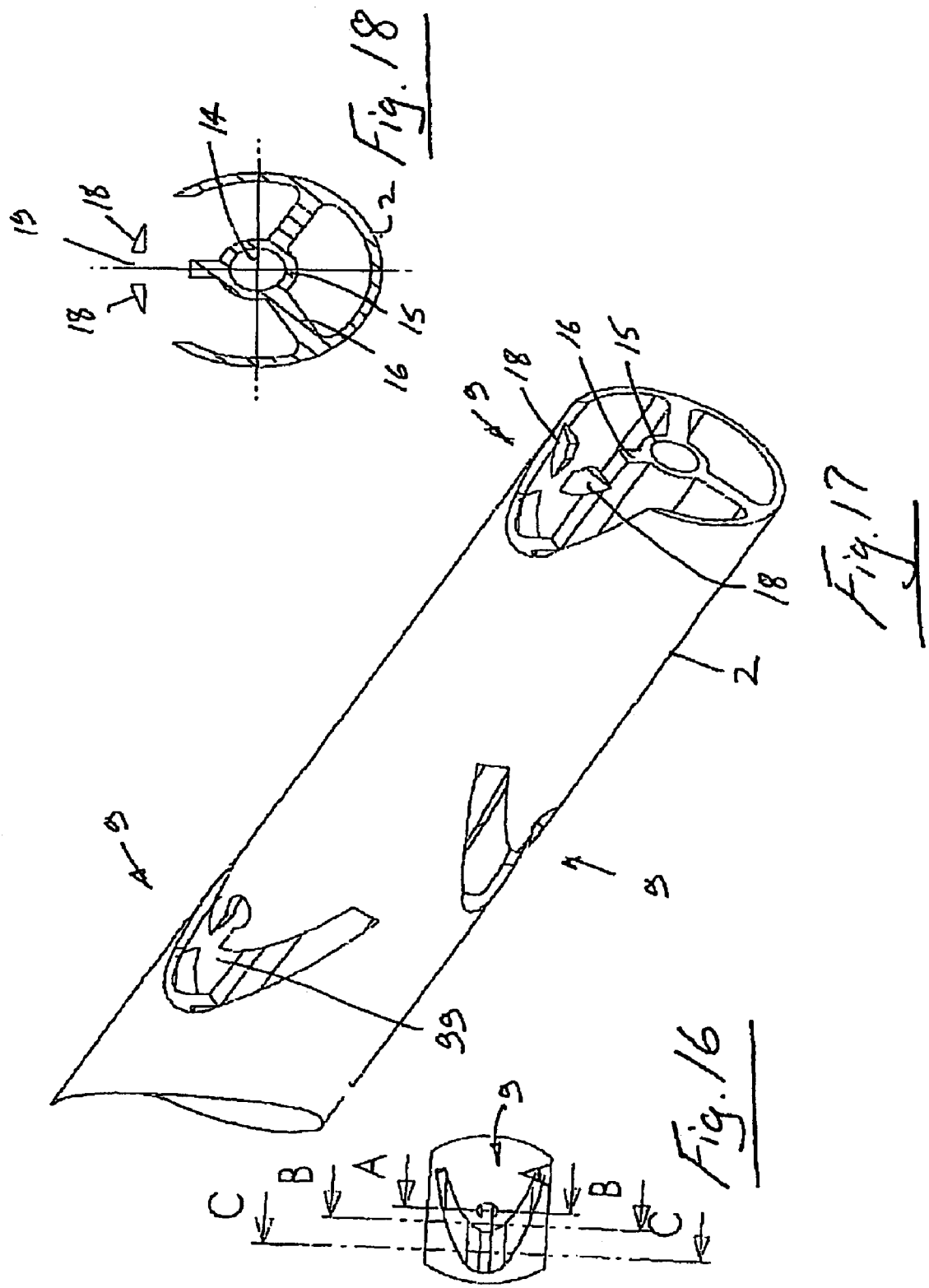

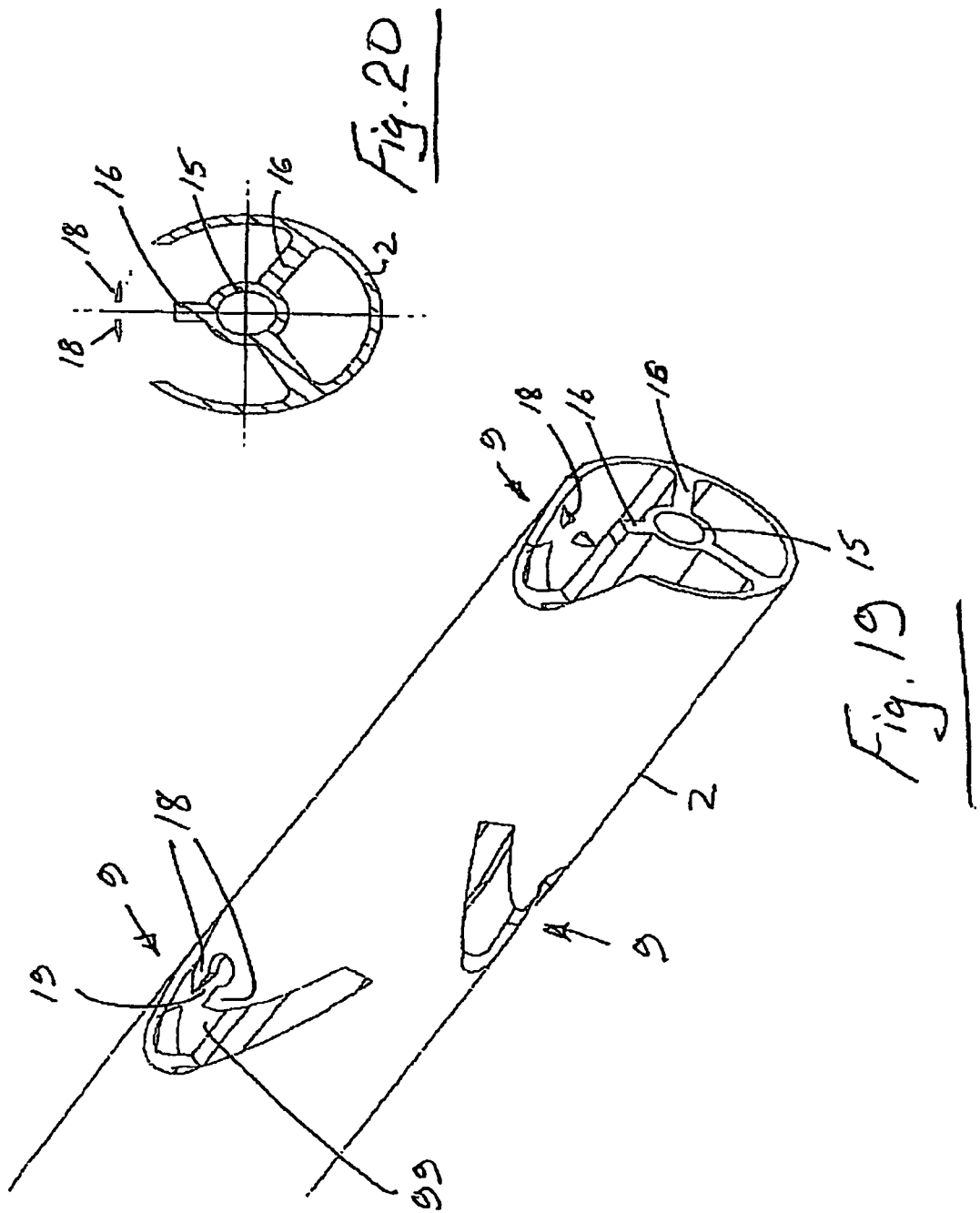

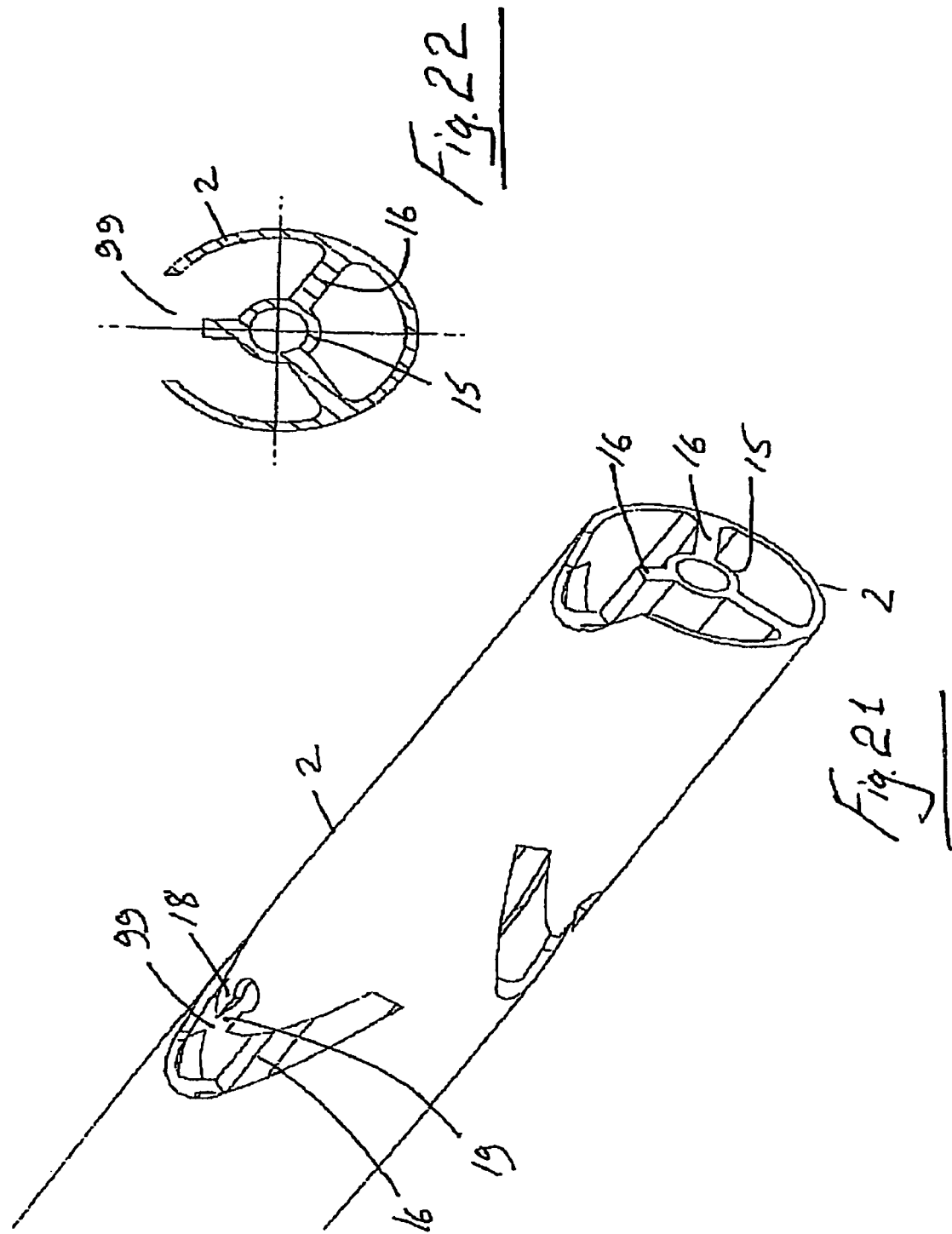

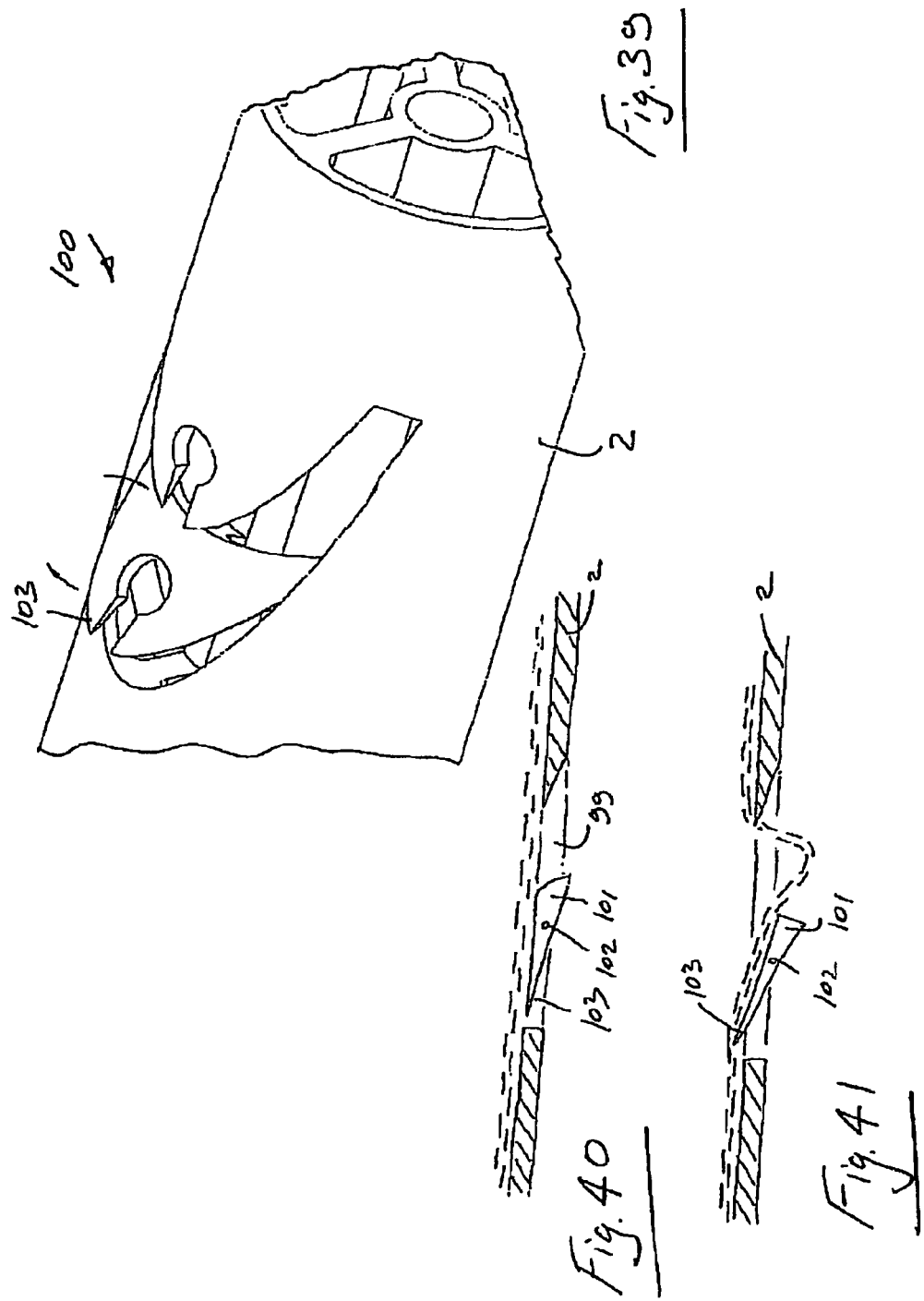

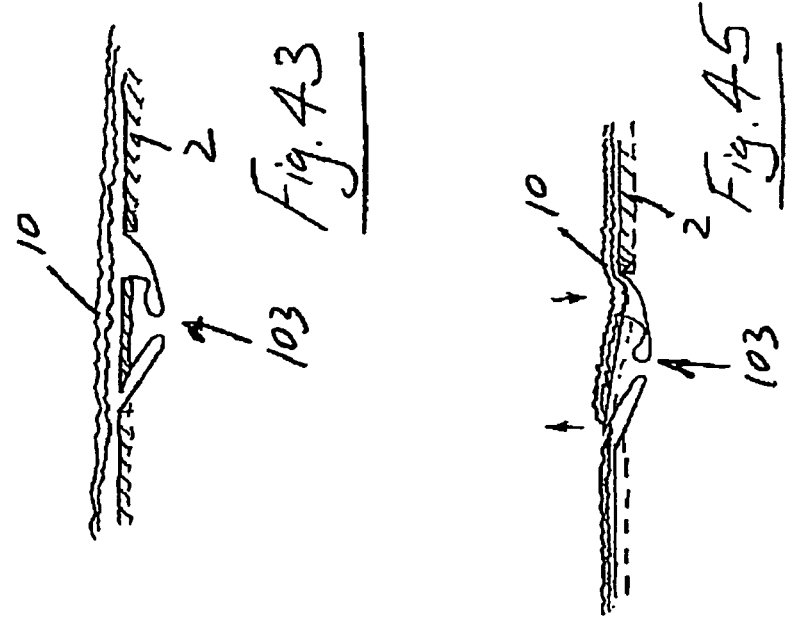
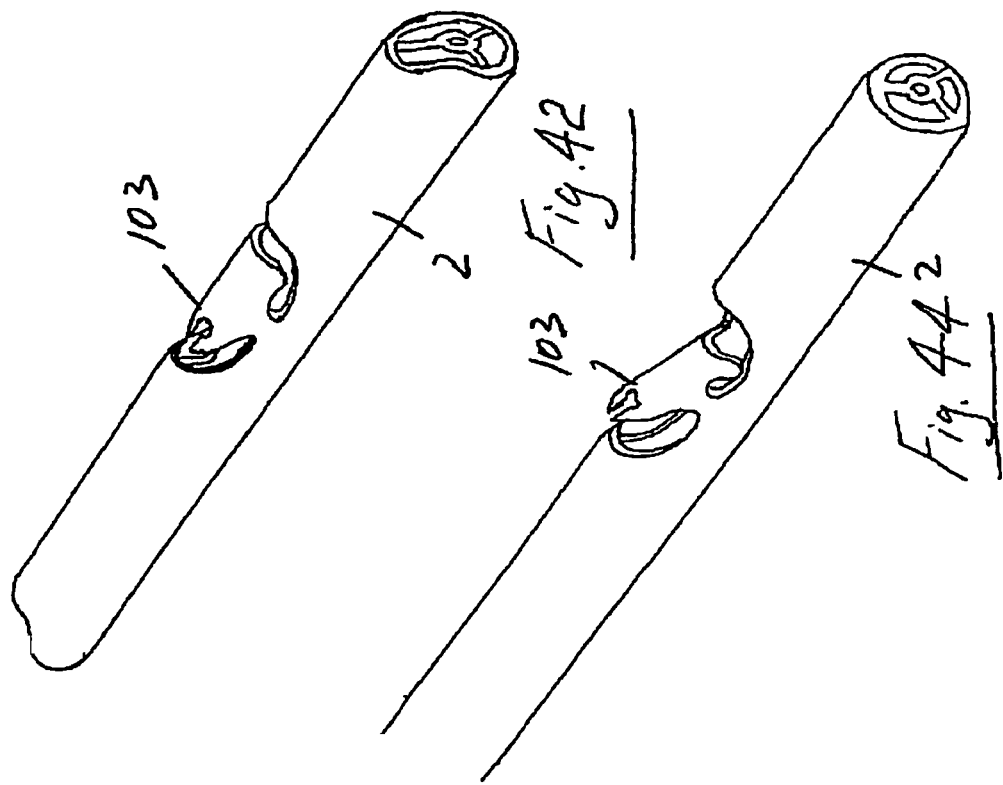

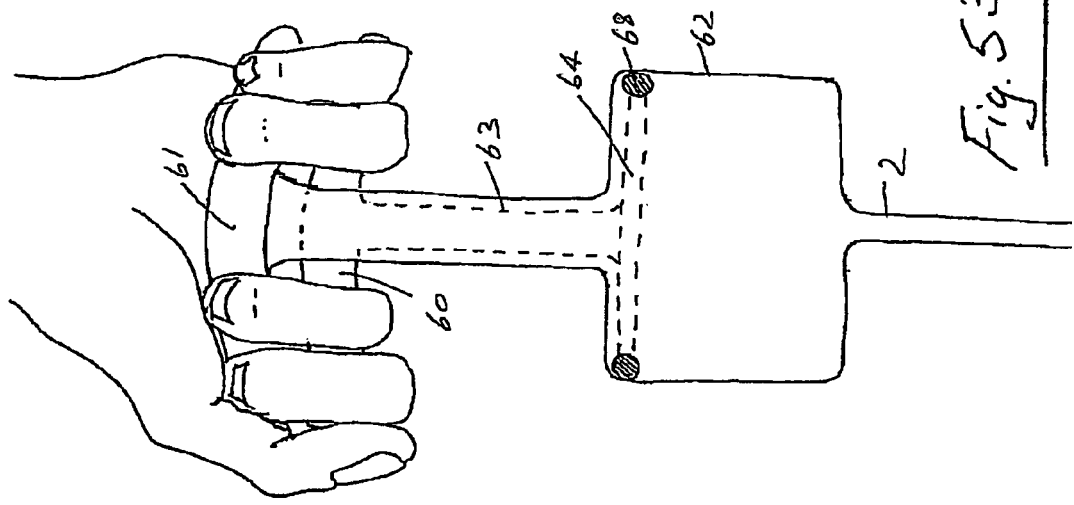
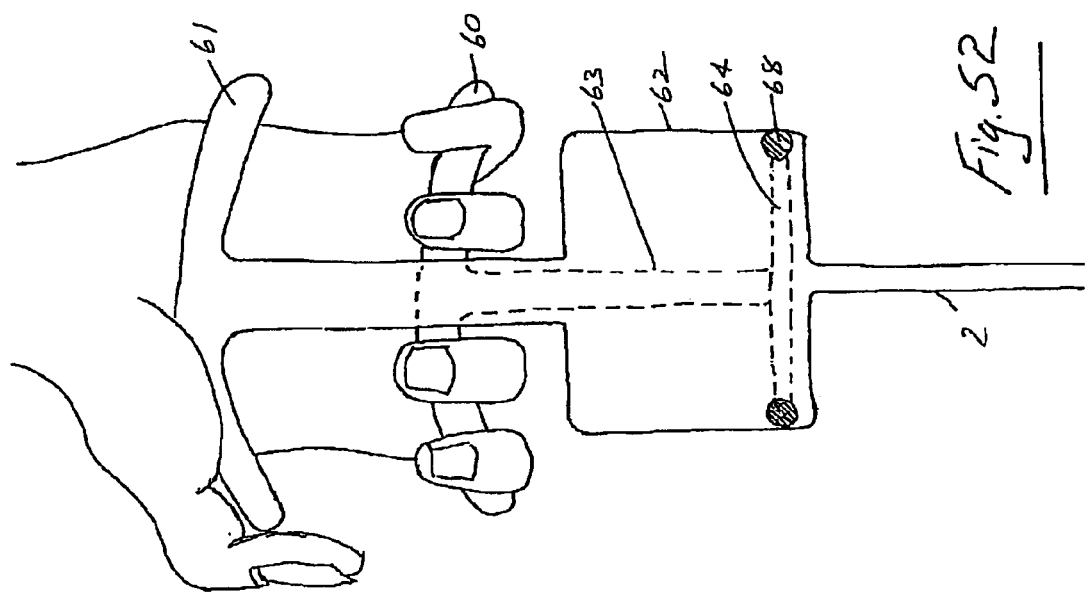

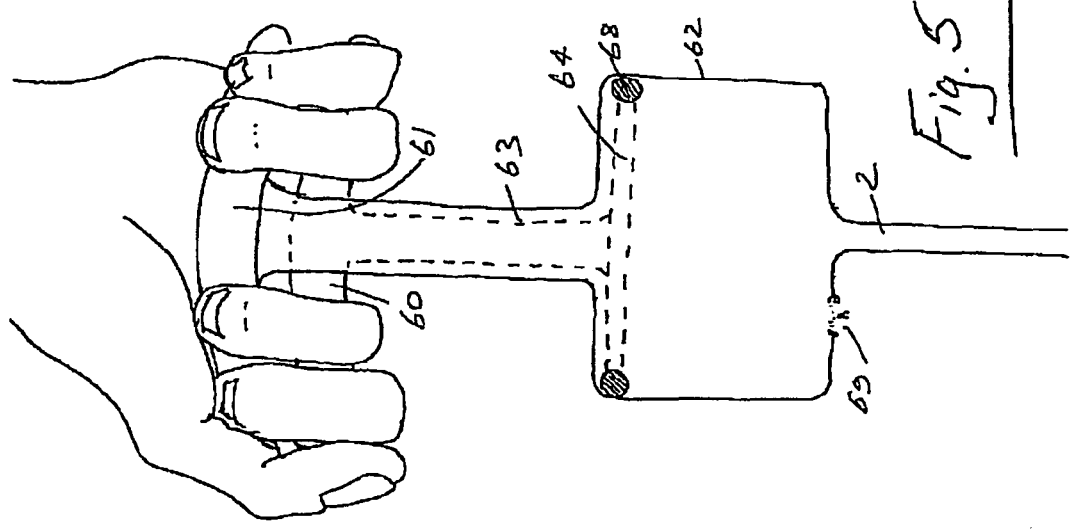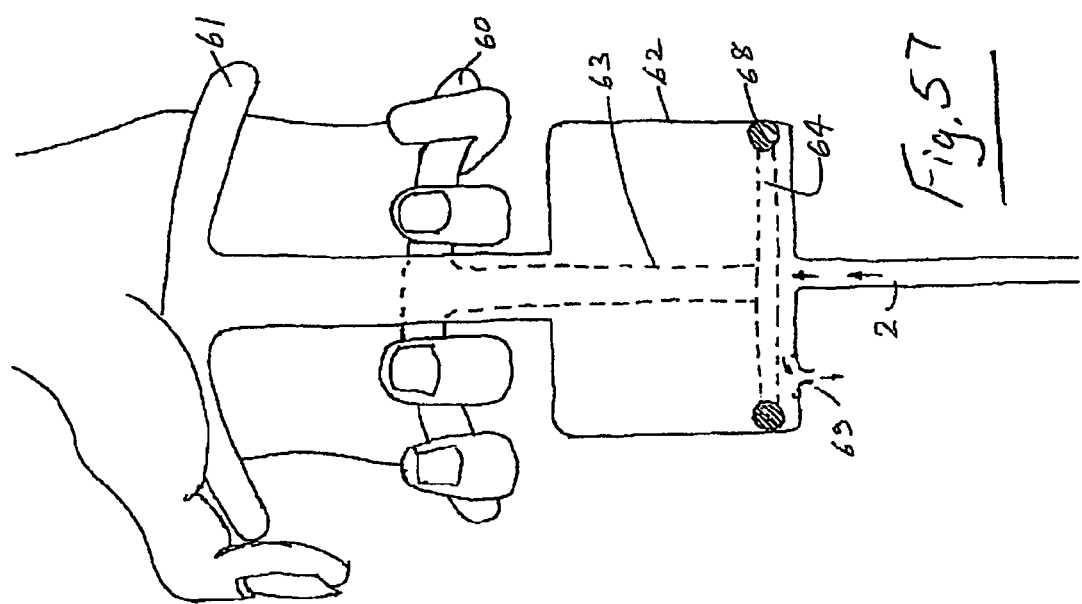

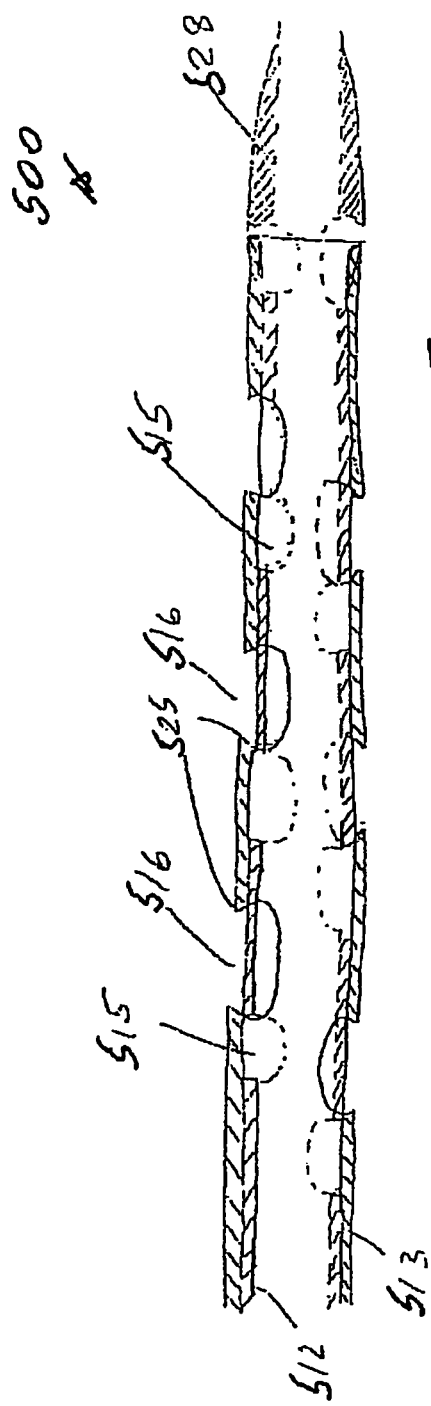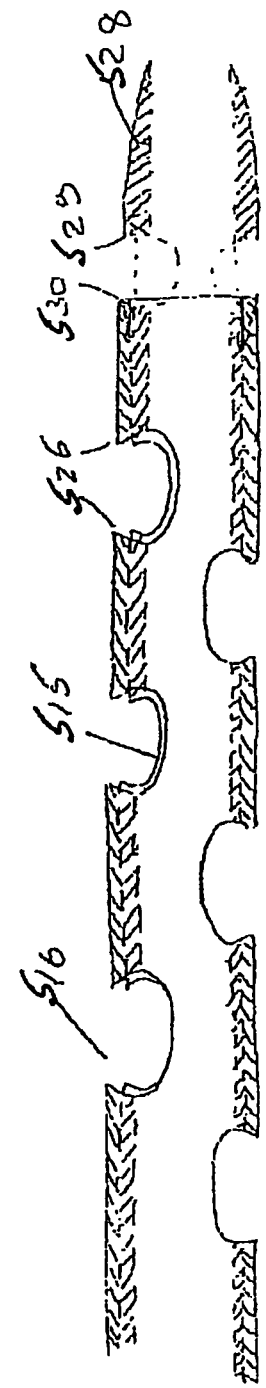

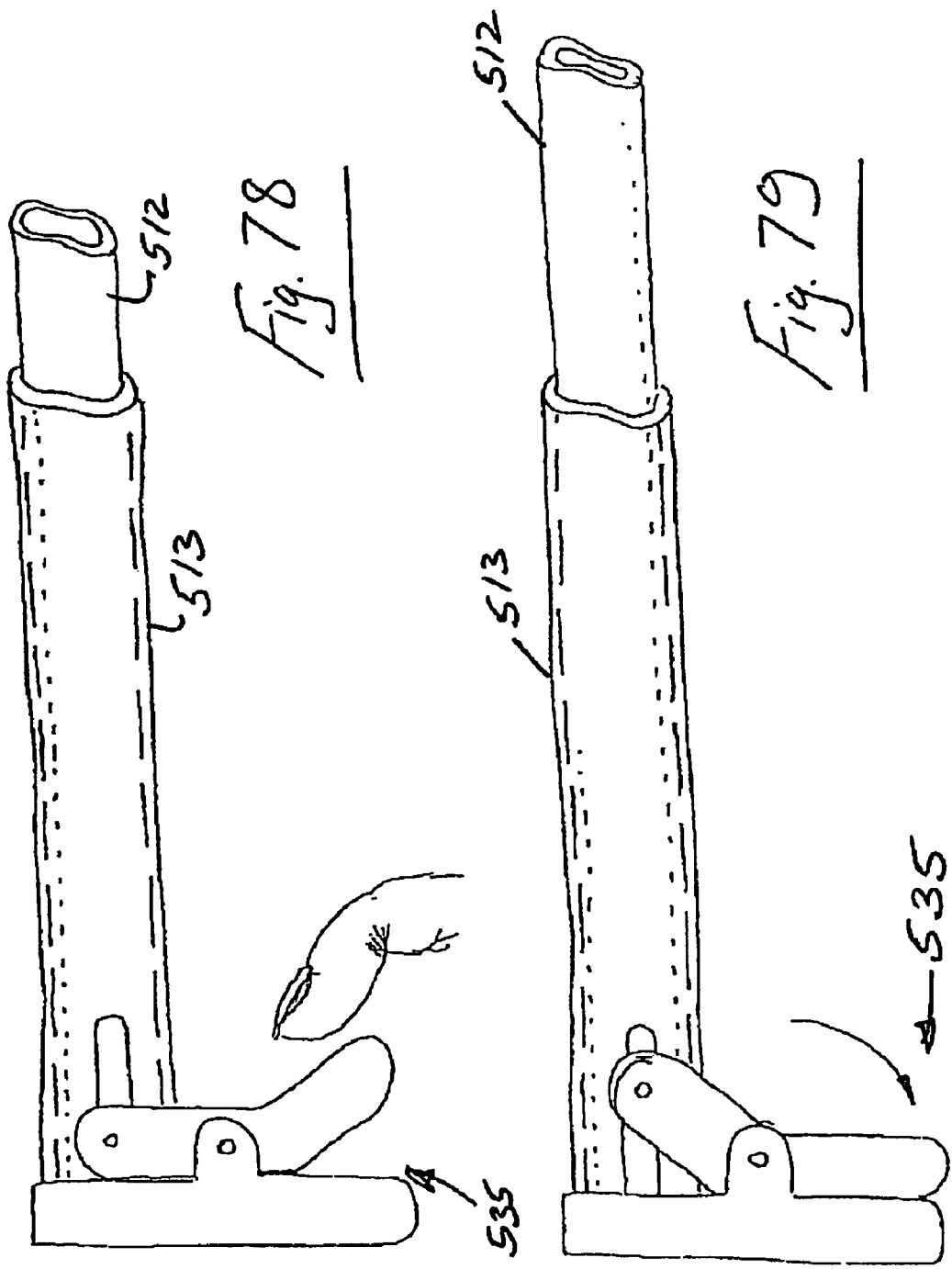

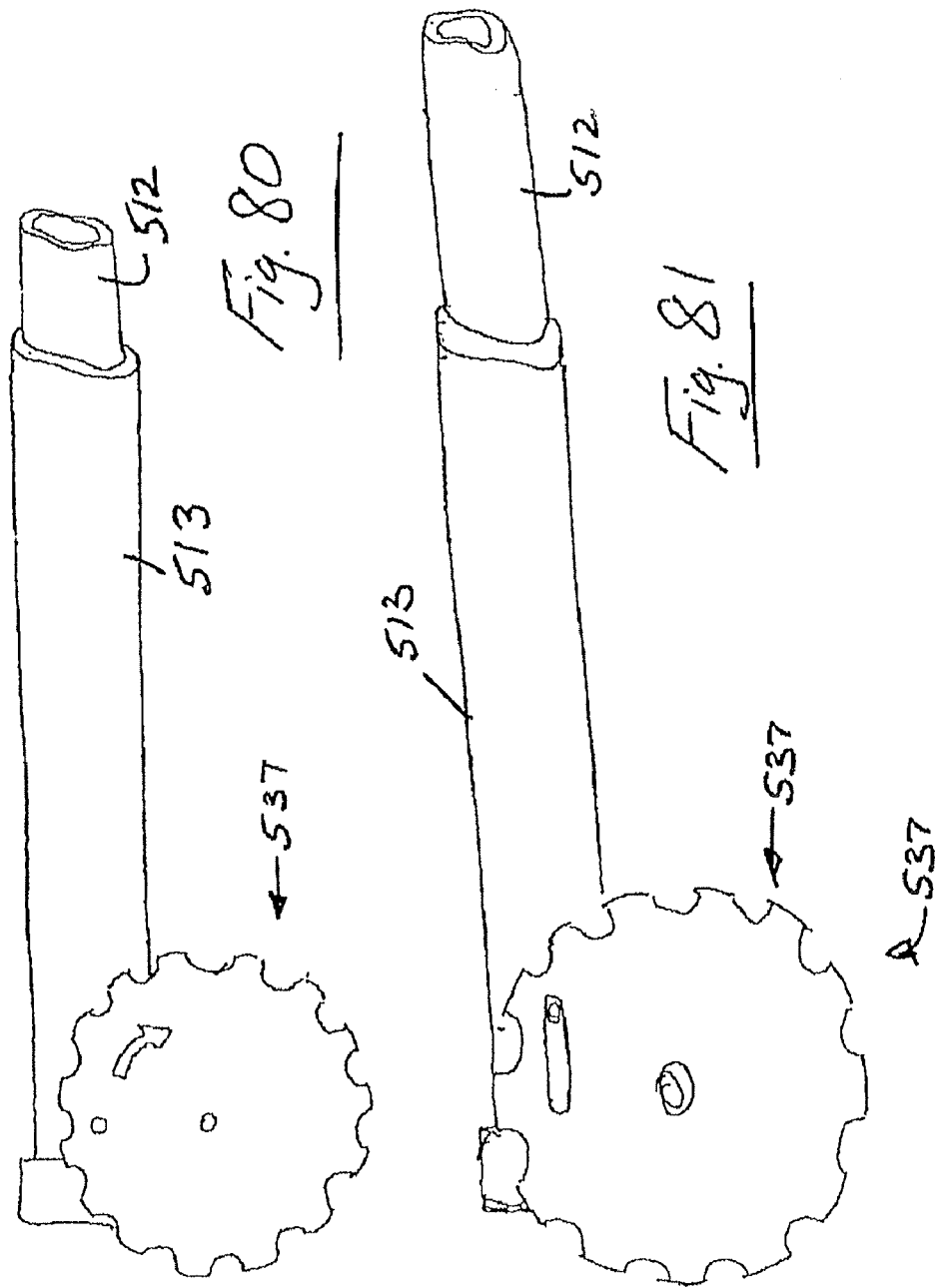

VEIN STRIPPING DEVICE

This is a complete application claiming benefit of provisional 61/136,622 filed on Sep. 19, 2008 and provisional 61/202,428 filed Feb. 27, 2009, which has a priority of Irish no. 2008/0430 filed May 29, 2008, hereby incorporated by reference.

INTRODUCTION

The invention relates to a device for stripping blood vessels such as veins. In particular, the invention relates to stripping the long saphenous vein in the treatment of varicose veins.

To strip the long saphenous vein it is known to use open keyhole technique surgery in which the groin is opened and the long saphenous vein is disconnected from the common femoral vein. It is also known to use a ball wire device. This is inserted through the incision at the groin and pulled through the incision above or below the knee, accumulating the vein on the ball as it is reamed through. This procedure is successful in that it completely removes the vein. However recovery is traumatic and slow as nerve and tissue damage are unavoidable with extensive bruising and eccymosis. In addition, when a vein is being removed in this manner blood will seep into the surrounding tissue. Once the blood leaves the environment of a blood vessel it will clot and is very difficult to remove. The blood then becomes a cause of inflammation and irritation.

One problem with other known devices for stripping veins is that in some cases the vein accumulates then folds over the accumulated mass and then shreds. When the vein shreds in this manner part of the vein may remain within the limb. This residual part of the vein which is left behind causes swelling and pain and may eventually reconstitute into a full saphenous vein. A second procedure is often required to remove the remainder of the vein within the limb. Tissue and nerves may be damaged during this second pass as there is no defined pathway through which to pass the device.

STATEMENTS OF INVENTION

According to the invention there is provided a vein stripping device comprising a catheter for insertion into a vein to be removed, the catheter having a proximal region adjacent a proximal end of the catheter and a distal region adjacent a distal end of the catheter, the catheter having a plurality of vein gripping means at least along the distal region.

In one aspect of the invention the catheter is open at the distal end thereof for passage of blood through the catheter from the distal end.

In another aspect of the invention the catheter comprises an outer tubular member and an inner tubular member which extends through at least the distal region of the catheter. In one embodiment the catheter comprises support rib means extending between the inner tubular member and the outer tubular member.

The support rib means may comprise a plurality of ribs extending between the inner and outer tubular members.

In one case the support rib means divides the lumen between the inner and outer tubular members into separate chambers.

In one embodiment the distal end of the inner tubular member is stepped back from the distal end of the outer tubular member.

In a preferred embodiment the distal end of the catheter is distally tapered.

The device may comprise an inner tubular member which extends to the distal end of the catheter. In this case the device may comprise support rib means between the inner tubular member and the outer tubular member and the rib means is distally tapered.

In one embodiment the outer diameter of the distal region of the catheter is uniform.

In another aspect of the invention the vein gripping means is movable. The vein gripping means may be movable in response to a vacuum being applied to at least the distal region of the catheter.

In one embodiment the vein gripping means is pivotally movable relative to the catheter.

The movable vein gripping means may be integral with the catheter.

In one embodiment the jaws of the vein gripping means define an entry slot for engagement with a vein. The entry slot may face towards the proximal end of the catheter. The rib may be cut-away inwardly in the region of the vein gripping means.

In one embodiment the gripping means extends on either side of a rib.

In one aspect the vein stripping device comprises:
  a proximal tube connected to the proximal region of the catheter;
  a blood collecting housing;
  the proximal tube extending through the blood collecting housing;
  a plunger which is movable through the housing to generate a vacuum in the catheter; and
  a plunger tube connected to and extending proximally of the plunger, the plunger tube having an opening through which blood from the proximal tube passes into the chamber proximally of the plunger.

In one embodiment a first handle is connected to the plunger tube and a second handle is connected to the housing, one of the handles being moved relative to the other handle to move the plunger through the housing. A movable handle may be moved towards the other handle to move the plunger through the housing.

In another aspect the vein stripping device comprises a non return valve means for venting of the catheter.

The non return valve means may be normally open and is closed on operation of the plunger.

In a further embodiment, the catheter comprises an outer tube and an inner tube, the inner tube being movable relative to the inner tube. The inner tube may be a close fit within the outer tube. In one case the inner tube comprises a plurality of holes and the outer tube comprises a plurality of holes, the tubes being movable relative to one another from an insertion configuration in which the holes in the outer tube are occluded by the inner tube to a stripping configuration in which the holes in the outer tube are aligned with the holes in the inner tube.

In another aspect the invention provides a vein stripping device comprising a catheter for insertion into a vein to be removed, the catheter having a proximal region adjacent a proximal end of the catheter and a distal region adjacent a distal end of the catheter, the catheter having a plurality of vein gripping means at least along the distal region for gripping a length of the vein to the catheter, the catheter comprising an outer tube and an inner tube, the inner tube being movable relative to the inner tube. The inner tube may be a close fit within the outer tube. The inner tube may comprise a plurality of holes and the outer tube comprises a plurality of holes, the tubes being movable relative to one another from an insertion configuration in which the holes in the outer tube are occluded by the inner tube to a stripping configuration in which the holes in the outer tube are aligned with the holes in the inner tube.

In a further aspect the invention provides a vein stripping device comprising a catheter for insertion into a vein to be removed, the catheter having a proximal region adjacent a proximal end of the catheter and a distal region adjacent a distal end of the catheter, the catheter having a plurality of vein gripping means at least along the distal region wherein the catheter comprises an outer tubular member and an inner tubular member which extends through at least the distal region of the catheter.

In a still further aspect the invention provides a method of stripping a vein comprising:
  inserting a catheter having an open distal end into a vein;
  applying a vacuum to the catheter to draw blood from the vein into the catheter;
  gripping the vein to the outer surface of at least the distal end of the catheter; and
  pulling the catheter proximally to remove the vein.

In one embodiment the method comprises turning the catheter to twist the vein before and/or during pulling of the catheter.

The vein may be a saphenous vein.

In another aspect the invention provides a vein stripping device comprising a catheter for insertion into a vein to be removed, the catheter having a plurality of vein gripping means at least along a distal region of the catheter wherein the catheter comprises a kinematic vein gripping means. In one embodiment a grip feature is displaced in use of the device (for example when suction is applied) into a gripping position. The displacement may be a kinematic displacement.

In one embodiment the device comprises means for drawing blood through the catheter from the distal end.

The means for drawing blood through the catheter from the distal end may comprise a vacuum generating means.

In one embodiment the device comprises a proximal housing for storage of blood.

As the catheter is inserted blood is allowed to vent freely through the catheter as it is being inserted. A non-return valve in the system facilitates this.

In one embodiment the catheter comprises an outer tubular member and an inner tubular member which extends through at least the distal region of the catheter. In one case the catheter comprises support rib means extending between the inner tubular member and the outer tubular member. The support rib means may comprise a plurality of ribs extending between the inner and outer tubular members.

In one embodiment the support rib means comprises a plurality of ribs extending between the inner and outer tubular members.

In one case the support rib means divides the lumen between the inner and outer tubular members into separate chambers.

In one embodiment the distal end of the inner tubular member is stepped back from the distal end of the outer tubular member.

The outer diameter of the distal region of the catheter may be uniform.

The wall thickness of the catheter may be distally tapered at the distal end thereof.

In one embodiment the vein gripping means do not extend radially outwardly of the outer circumference of the catheter.

In one case the vein gripping means comprises a hole in the catheter.

The vein gripping means may comprise engagement means for engagement with a vein wall. In one case the vein engagement means comprises jaws for engagement with a vein. The jaws may be adapted to engage with a vein in response to movement of the catheter in the proximal direction.

The jaws may define an entry slot for engagement with a vein. The entry slot may face towards the proximal end of the catheter.

In one case the jaws are biased towards a vein engagement configuration.

The gripping means may extend on either side of a rib. The rib may be cut-away inwardly in the region of the vein gripping means.

The internal ribs structurally reinforce and strengthen the vein grip features.

In one embodiment the vein stripping device comprises guide means over which the inner tubular member travels.

In one case the outer tubular member has an exit port for the guide means. The exit port may be distal of the proximal end of the catheter. In one case the inner tubular member extends to the exit port.

In one embodiment the guide means comprises a guidewire.

The guide means may comprise a hollow lumen. In this case the guide means may contain an anaesthetic and/or a pharmaceutical.

In one embodiment the vein stripping device comprises vacuum generating means for drawing a vein into the vein gripping means. The vacuum generating means for drawing a vein into the vein gripping means may be the same as the vacuum generating means for drawing blood through the catheter.

In one embodiment the vacuum generating means comprises a plunger which is movable to draw a vacuum.

In one case the plunger is movable through the catheter from the distal end towards the proximal end.

There are several methods for moving the plunger through the catheter. In one case the plunger is located at the distal end of the catheter and has a tension line attached which runs to the proximal end the tension line can be drawn by:

A rack and pinion system can be attached to the handle whereby when the handle is pushed or pulled as a rack mechanism it causes a pinion and wheel to rotate which reels in the plunger. For a balanced movement of four wheels pull four tension lines simultaneously.

A coiled leaf spring may be released to cause a wheel to rotate which will reel in the tension line at a predetermined rate.

The plunger may also be retracted through the catheter by the other methods of drawing a vacuum described herein. When retracted in this manner there is no need for a tension line. The rate of retraction is influenced by the coefficient of friction between the plunger and the body of the catheter along with the intensity of the vacuum.

The vacuum generating means may comprise a vacuum chamber in which the plunger is mounted, the plunger having a handle for drawing the plunger through the chamber. The handle may be movable proximally to draw a vacuum.

In one embodiment the vein gripping means comprise a plurality of holes and/or a plurality of grip features which may amount to a texturing of the entire surface of the catheter with gripping spaced-apart along the wall of the catheter. The holes may be longitudinally spaced-apart along at least the distal region of the catheter. At least some of the holes may be radially spaced-apart in the catheter wall.

In one embodiment the device comprises vein detaching means at a distal end of the catheter. In one embodiment the device has no means of piercing or severing the vein. The vein is gripped substantially along its length and is detached by means of pulling or tensile force.

In one embodiment the catheter is of non-circular shape in transverse cross section. The catheter may be oval in transverse cross section.

The vacuum generating means may comprise a port for connection to a vacuum generating system. Alternatively the vacuum generating means comprises a plunger. In one case the vacuum generating means comprises a syringe.

BRIEF DESCRIPTION OF THE DRAWINGS

The invention will be more clearly understood from the following description thereof given by way of example only, with reference to the accompanying drawings, in which:

FIG. 2 is another isometric view of the device;

FIG. 3 is another isometric view of the device with one type of guide means in place;

FIGS. 5 to 11 are isometric views illustrating various stages in stripping the long saphenous vein using the device of FIGS. 1 to 3;

FIG. 13 is a longitudinal cross sectional view of the device of FIG. 12;

FIG. 14 is a cross sectional view on the line XIV-XIV of FIG. 13;

FIG. 15 is an end view in the direction of the arrow XV in FIG. 13;

FIG. 16 is a plan view of one vein gripping feature of the device;

FIGS. 17 and 18 are respectively isometric and cross sectional views on the line A-A of FIG. 16;

FIGS. 19 and 20 are respectively isometric and cross sectional views on the line B-B of FIG. 16;

FIGS. 21 and 22 are respectively isometric and cross sectional views on the line C-C of FIG. 16;

FIG. 39 is an isometric, partially cut-away view of part of another vein stripping catheter;

FIGS. 40 and 41 are cross sectional views illustrating the device of FIG. 39 in different positions of use;

FIG. 42 is an isometric view of another vein stripping catheter in one configuration;

FIG. 43 is a cross sectional view of portion of the catheter of FIG. 42 with a vein in position;

FIG. 44 is an isometric view of the vein stripping catheter of FIG. 42 in a vein gripping configuration;

FIG. 45 is a cross sectional view of portion of the catheter of FIG. 44 with a vein in position;

FIGS. 50 to 53 are cross sectional views of a proximal movable end of the device at various stages during vein stripping;

FIGS. 55 to 58 are cross sectional views of an alternative proximal movable end of a vein stripping device at various stages during vein stripping;

FIG. 73 is a cross sectional view of a distal end of another vein stripping device of the invention in one configuration of use whereby vein gripping features on an outer tube are occluded by an inner tube;

FIG. 74 is a cross sectional view of the distal end of the device of FIG. 73 in another configuration of use whereby holes on the inner tube are aligned with the holes on the outer tube;

FIGS. 78 and 79 are cut-away isometric views another proximal actuating means of the device;

FIGS. 80 and 81 are cut-away isometric views of an alternative proximal actuating means;

DETAILED DESCRIPTION

Figure 1:
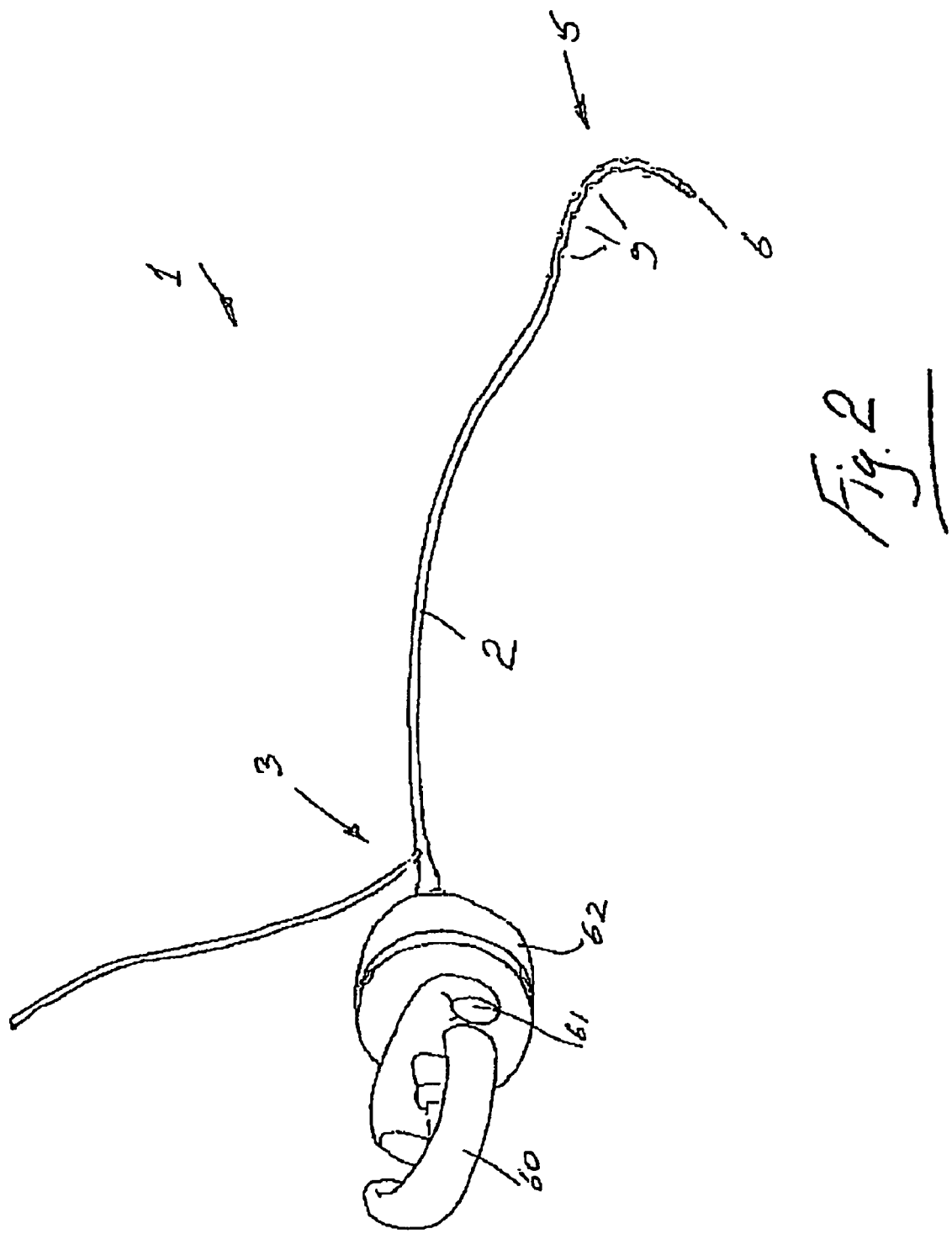
FIG. 1 is an isometric view of a vein stripping device according to the invention.
Figure 4:
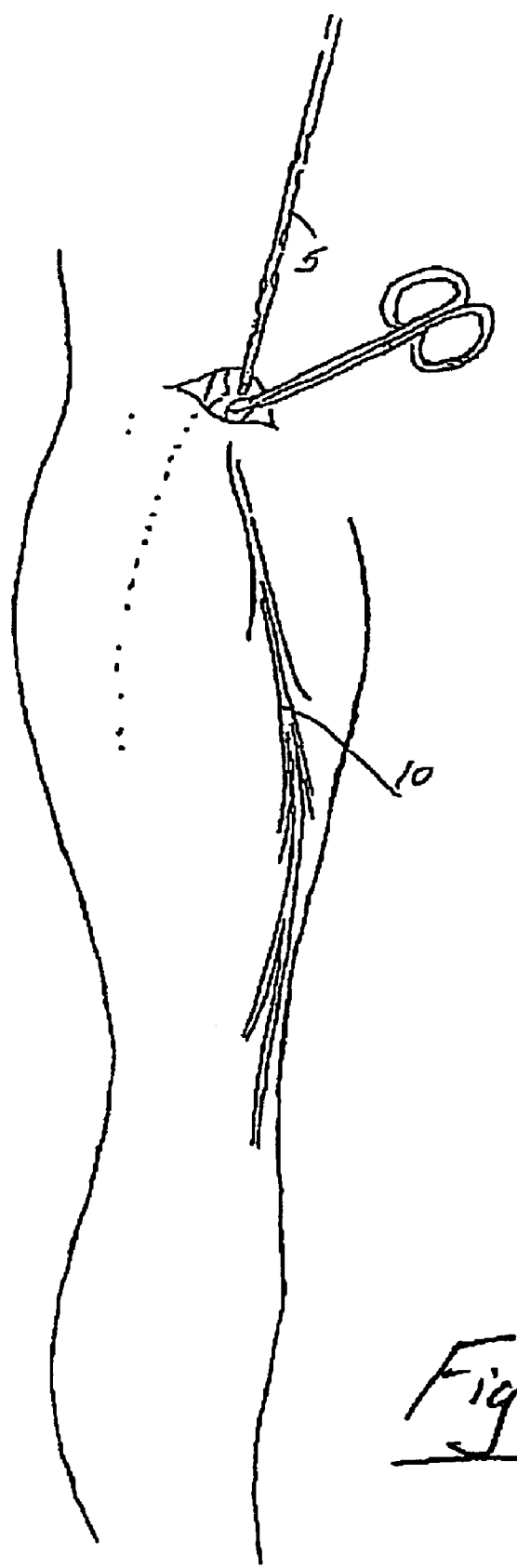
FIG. 4 is an isometric view of a distal end of the device of FIGS. 1 to 3 being inserted into the long saphenous vein.

Referring to the drawings there is illustrated a vein stripping device 1 according to the invention. In this specification the term catheter is used to denote a tube or a lumen.

The vein stripping device 1 of the invention comprises a catheter 2 for insertion into a vein such as a saphenous vein 10 to be removed. The catheter 2 has a proximal region 3 adjacent a proximal end of the catheter and a distal region 5 adjacent a distal end 6 of the catheter. The catheter has a plurality of vein gripping means 9 at least along the distal region 5 for gripping a vein 10 to the catheter.

Figure 11:
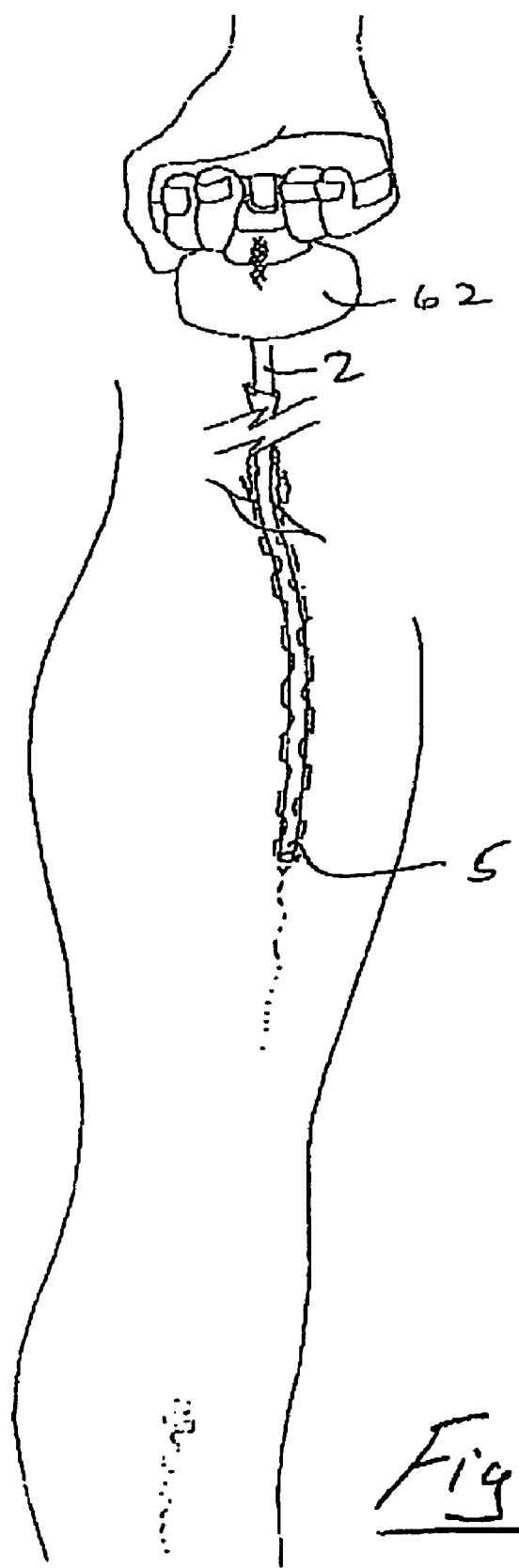

A vacuum is in this case used to draw the vein 10 against the vein gripping means 9 when the device is in the stripping configuration. Blood is also drawn out of the vein 10 at this stage. Blood may be drawn from the vein 10 as the device is being inserted into the vein 10. When a vein is gripped by the gripping means 9 the device is then pulled at the proximal end so that the vein 10 is distended and detached at either the distal tip of the device or at some point further along the length of the vein 10. The vein 10 is gripped to the catheter substantially along the length thereof. Pulling the catheter back proximally pulls the vein 10 and or the subadventitial layers of the vein to detachment so that all of the vein 10 is removed as illustrated particularly in FIGS. 10 and 11.

As the vein distends it elongates until it reaches the elastic limit. At this point it breaks or snaps apart. The remaining elongated vein recoils and shrivels into a sealed mass which prevents blood from seeping into the channel. The same process applies to tributaries or perforators.

In the invention the vein is gripped along a length of typically 3 cm to 5 cm and is peeled away from the attaching layers or membranes to minimise injury.

The device is hollow and is open at the distal end 6. This allows blood to pass freely through the device and to be evacuated from the vein 10 prior to detaching and removing the vein 10. It also improves the navigability of the device through the vein 10. A pointed tip can embed in the wall of the vein 10, because the pressure of the forward motion of the tip is concentrated at one point. In one aspect of the invention there is a hollow tip which distributes the pressure of moving forward equally around the wall of the vein 10 and therefore will not be captured by a single feature inside the vein. The means of detaching the vein is achieved by gripping the vein substantially along its length along the device so that the entire vein can be pulled or drawn. The effect of this is that the vein 10 will fail at a point of weakness along its length beyond the distal tip of the device and further down the leg into the region of the calf. The result is that more of the vein may be removed than would be removed with conventional devices and this is a better outcome for the patient.

The catheter 2 has an exit port 11 (see especially FIG. 3) in the sidewall thereof adjacent the proximal end of the device 1. The catheter 2 may be tracked over a guide means comprising a guidewire such as a hollow guidewire 12. The guidewire extends from the open distal end 6 of the catheter and exits the catheter through the proximal exit port 11.

The device is withdrawn over the wire (guiding lumen) when the vein is firmly attached to it by pulling the device at the handles proximal to it.

The guidewire 12 may also be used to deliver a pharmaceutical such as an anaesthetic to the region where the vein is removed.

In this case the catheter comprises an outer tubular member 2 and an inner tubular member 15 which extends through at least the distal region of the catheter. The inner tubular member 15 has a central lumen 14. Support means in this case comprise three support ribs 16 which extend between the outer wall of the inner tubular member 15 and the inner wall of the outer tubular member 2 to support the outer tubular member 2, especially in the region of the vein gripping features 9.

In one case the support ribs 16 divide the lumen between the inner and outer tubular members 2, 15 into separate chambers. This ensures that if for some unforeseen reason the vacuum in one chamber fails it can be maintained in the other chambers.

Figure 12:
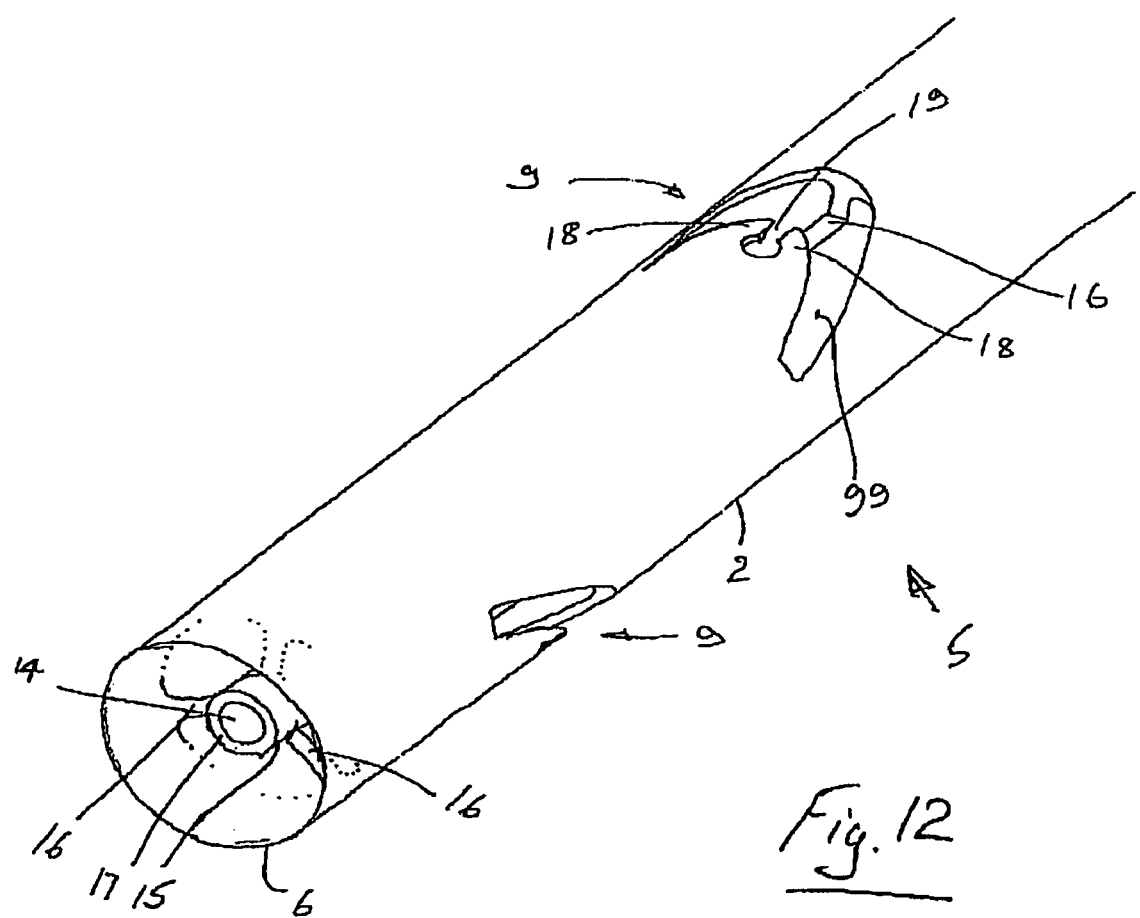
FIG. 12 is an isometric view of a distal region of a vein stripping device.

Referring to FIGS. 12 and 14 it will be noted that a distal end 17 of the inner tubular member 15 may be stepped back from the distal end of the outer tubular member 2. This ensures free flow of blood into the catheter and provides a relatively flexible tip to the device for smooth navigation through the vein.

Alternatively (such as FIGS. 27 to 31), inner ribs may step forward in a gently curved profile to aid the initial insertion of the device into a vein.

The inner tubular member 15 in this case extends to the guidewire exit port 11 in the outer tubular member 2. This facilitates tracking of the device over the guidewire 12. In the case where there is a side exit port 11 the guidewire 12 can be used in a rapid exchange (Rx) manner which facilitates ease of use as a relatively short guidewire can be used.

The outer diameter of at least the distal region of the catheter 2 is uniform to facilitate passage of the device through a vein 10 to be removed without snagging. To provide enhanced flexibility the wall thickness of the catheter is distally tapered at the distal end 6 thereof as illustrated particularly in FIG. 13.

The vein gripping means 9 do not extend radially outwardly of the catheter wall at least during insertion. This is important in providing a smooth profile to prevent snagging on the vein as the device is being inserted.

Each vein gripping means 9 comprises a hole 99 in the wall of the outer tubular member 2. There are also features which are typically laser cut to provide engagement means for engagement with a vein wall. Referring especially to FIGS. 12 to 22, the vein engagement means in this case comprises a pair of proximally extending jaws 18. The jaws 18 are adapted to engage with a vein in response to movement of the catheter in the proximal direction. The jaws 18 in this case define an entry slot 19 which faces towards the proximal end of the device so that the jaws engage with a vein as the device is moved proximally. The arrangement is such that the jaws 18 are biased towards a vein engagement configuration.

For enhanced support the vein gripping means 9 extends on either side of a rib 16. This also ensures that if a vacuum in one chamber (defined between adjacent ribs) fails, the vein is still retained by the vacuum applied to the adjacent chamber.

The grip features may have an opening proximal to a combination of pointed parts. More than one pointed part facilitates distribution of the attachment load and minimizing any possibility of the vein shredding, tearing and detaching. The grip features may also assist in capturing of the vein tissue between jaws.

Figures 23, 24:
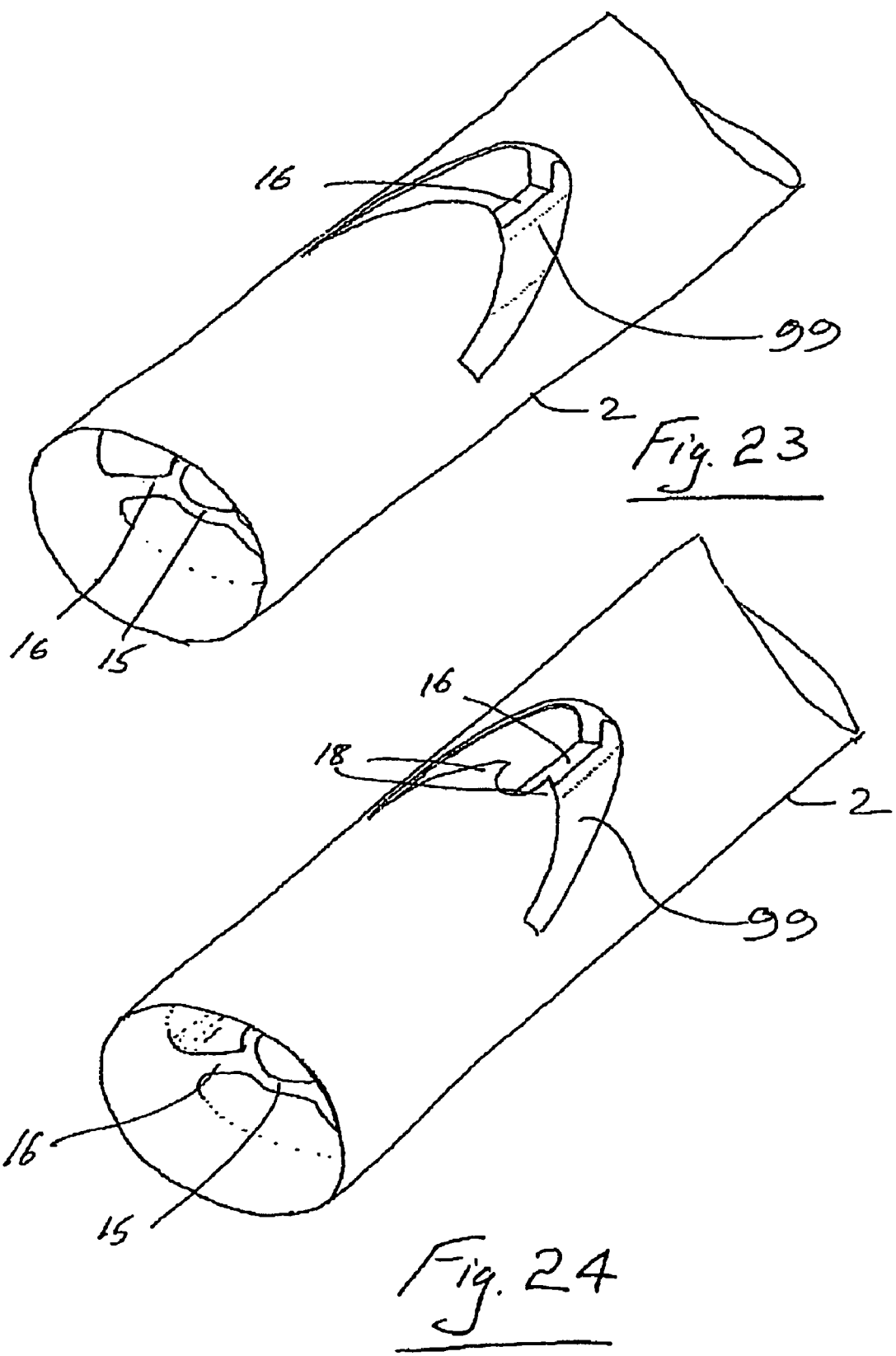
FIGS. 23 to 26 are isometric views of a distal region of vein stripping devices with alternative vein gripping features.
Figure 25:
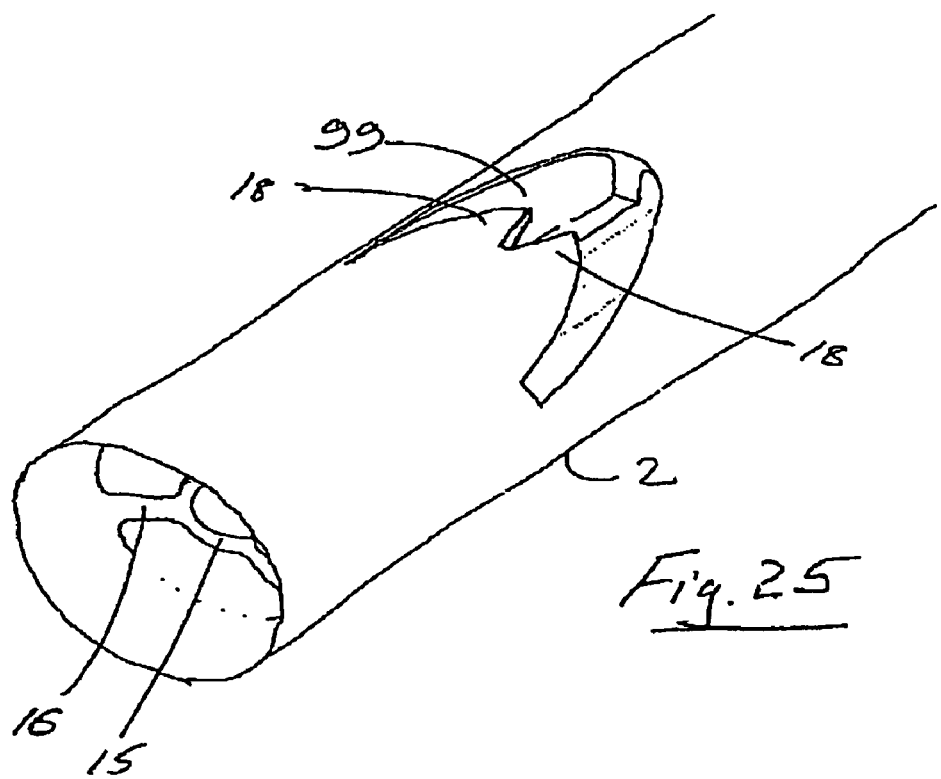

Many variations of vein gripping features are envisaged. For example, referring to FIG. 23 the hole 99 in the catheter wall may be cresent shaped. This shape or the following adaptions of this shape promote the effective gripping of the vein while being suctioned or evacuated internal to the catheter lumen through the opening proximal to this shape. In another case illustrated in FIGS. 24 and 25 the cresent-shaped hole may be further cut-away to provide gripping jaws. The jaws may be somewhat pointed in the proximal direction as illustrated in FIG. 24 to provide more positive gripping and clamping of the vein or may be V-shaped as illustrated in FIG. 25 to provide attachment of the vein. In both instances the vein will be sucked onto the cresent shaped feature through the opening proximal to it. The vein will then become securely attached to the pointed features.

In these cases the ribs 16 may be cut back radially underneath the hole 99 in order to provide an enlarged line into which the vein may be drawn.

Figure 26:
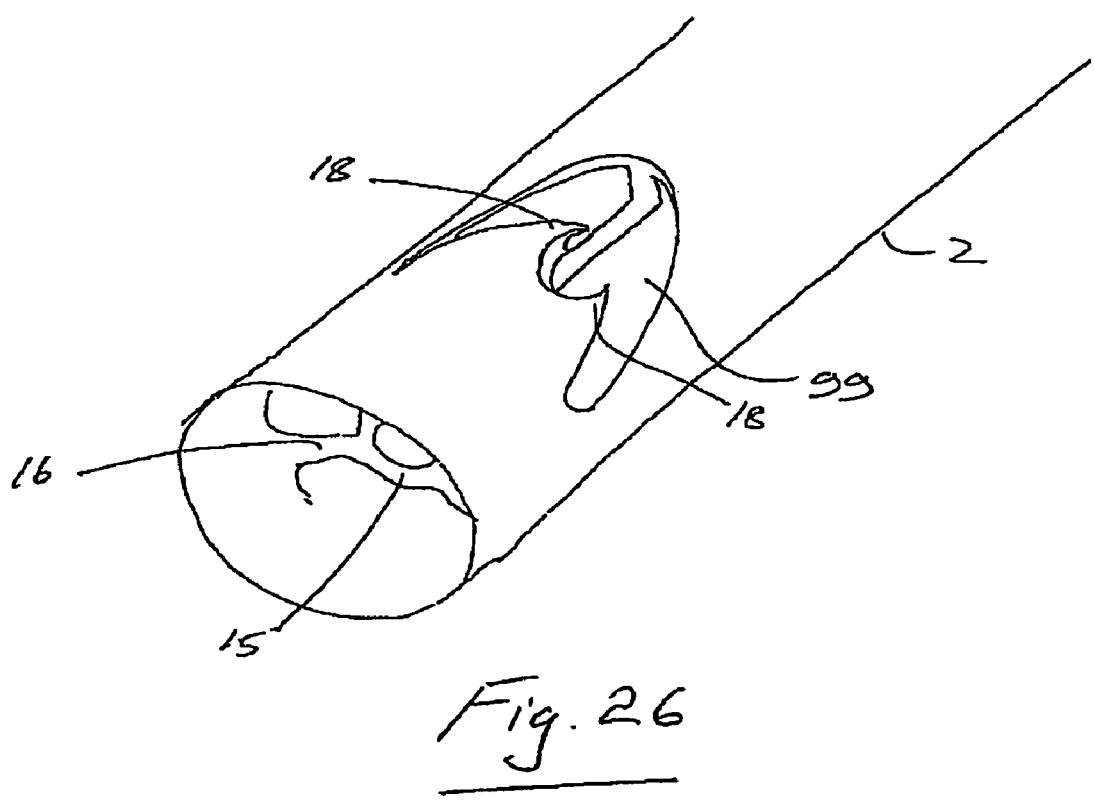

Referring to FIG. 26 the jaws 18 may be offset with respect to the underlying rib 16 so that the rib extends further upwards to support the jaw 18.

Figure 27:
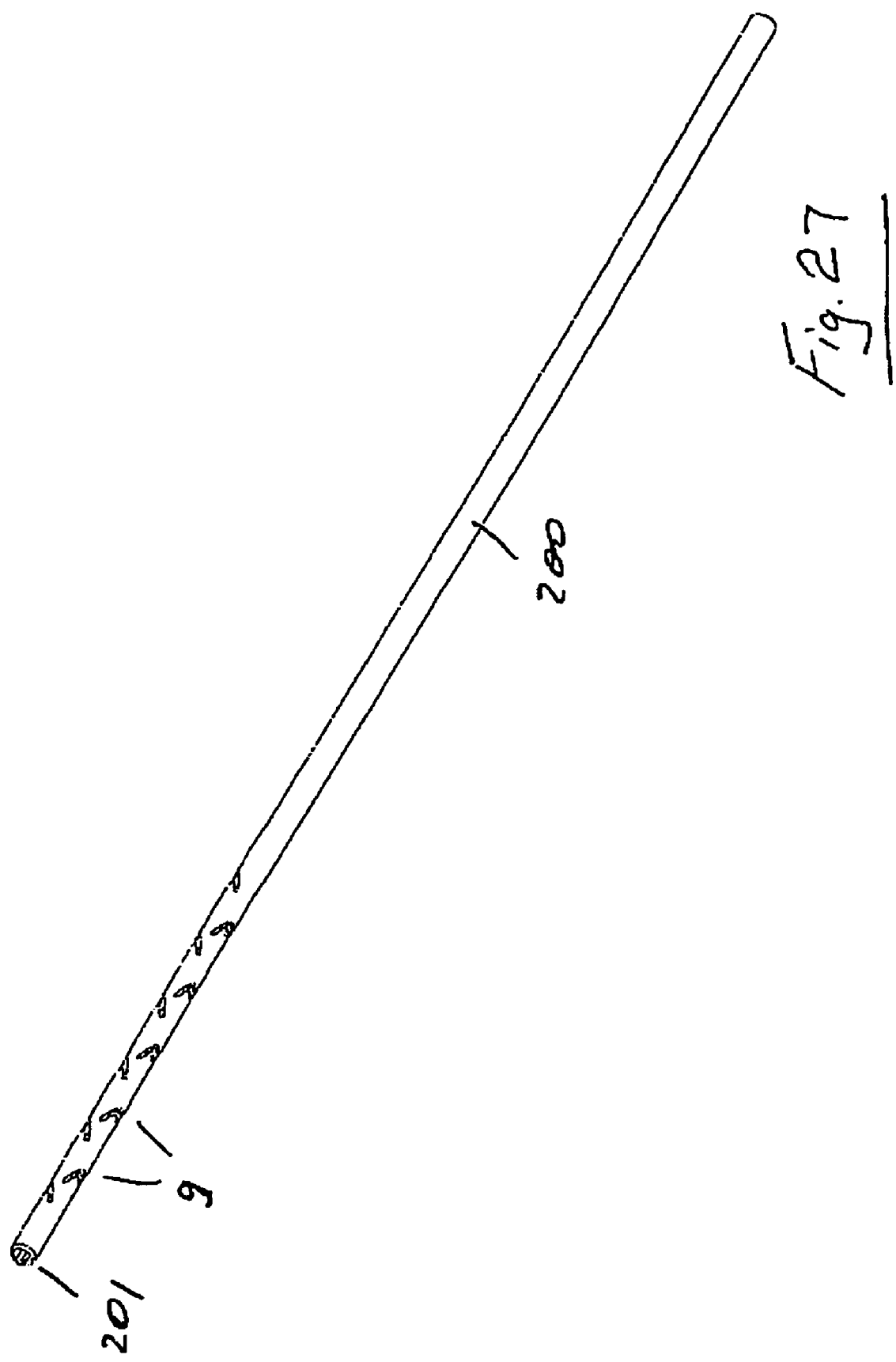
FIG. 27 is an isometric view of the catheter of another vein stripping device of the invention.
Figure 28:
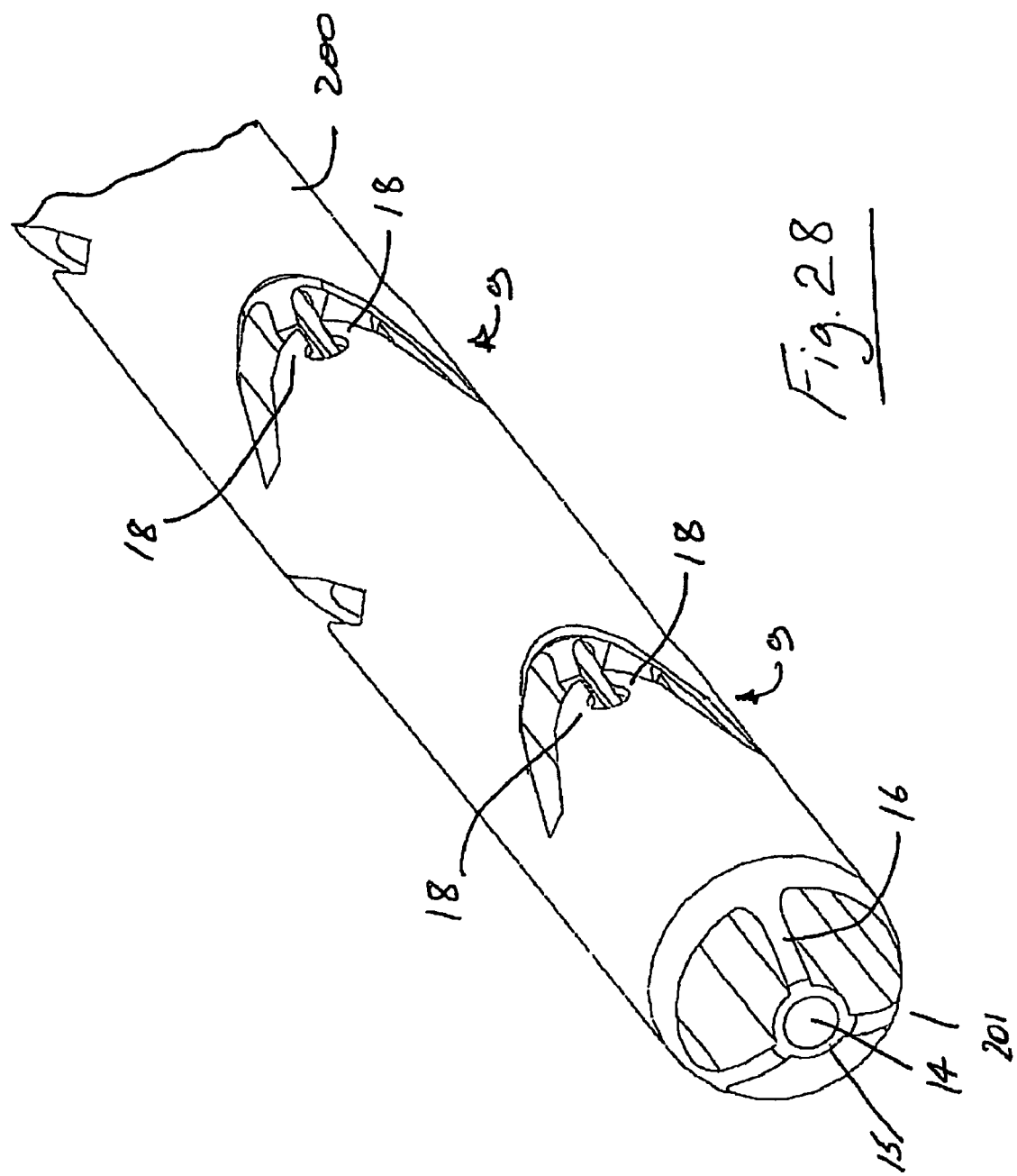
FIG. 28 is an enlarged isometric view of a distal region of the catheter.

Referring to FIGS. 27 and 28 there is illustrated a distal end of another vein stripping catheter 200 according to the invention. The catheter has some of the features of the catheters described above and like parts are assigned the same reference numerals. In this case the inner tubular member 15 projects distally and the ribs 16 are tapered distally for ease of insertion of the device into a vein to be stripped. The distal end 201 of the outer tubular member 2 is also provided/tapered distally to aid insertion into a vein.

Figure 29:
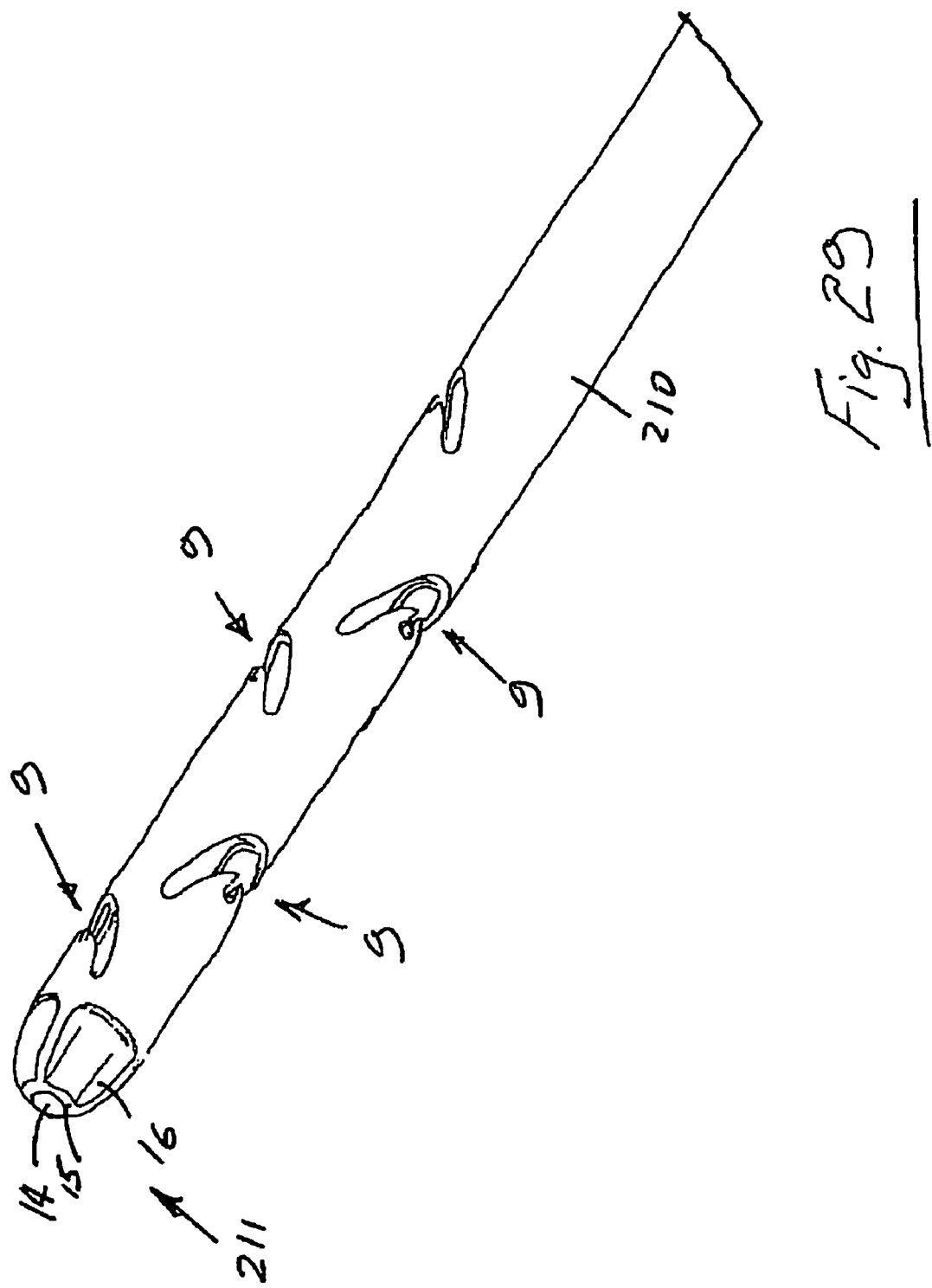
FIG. 29 is an isometric view of a distal end of another catheter.
Figure 30:
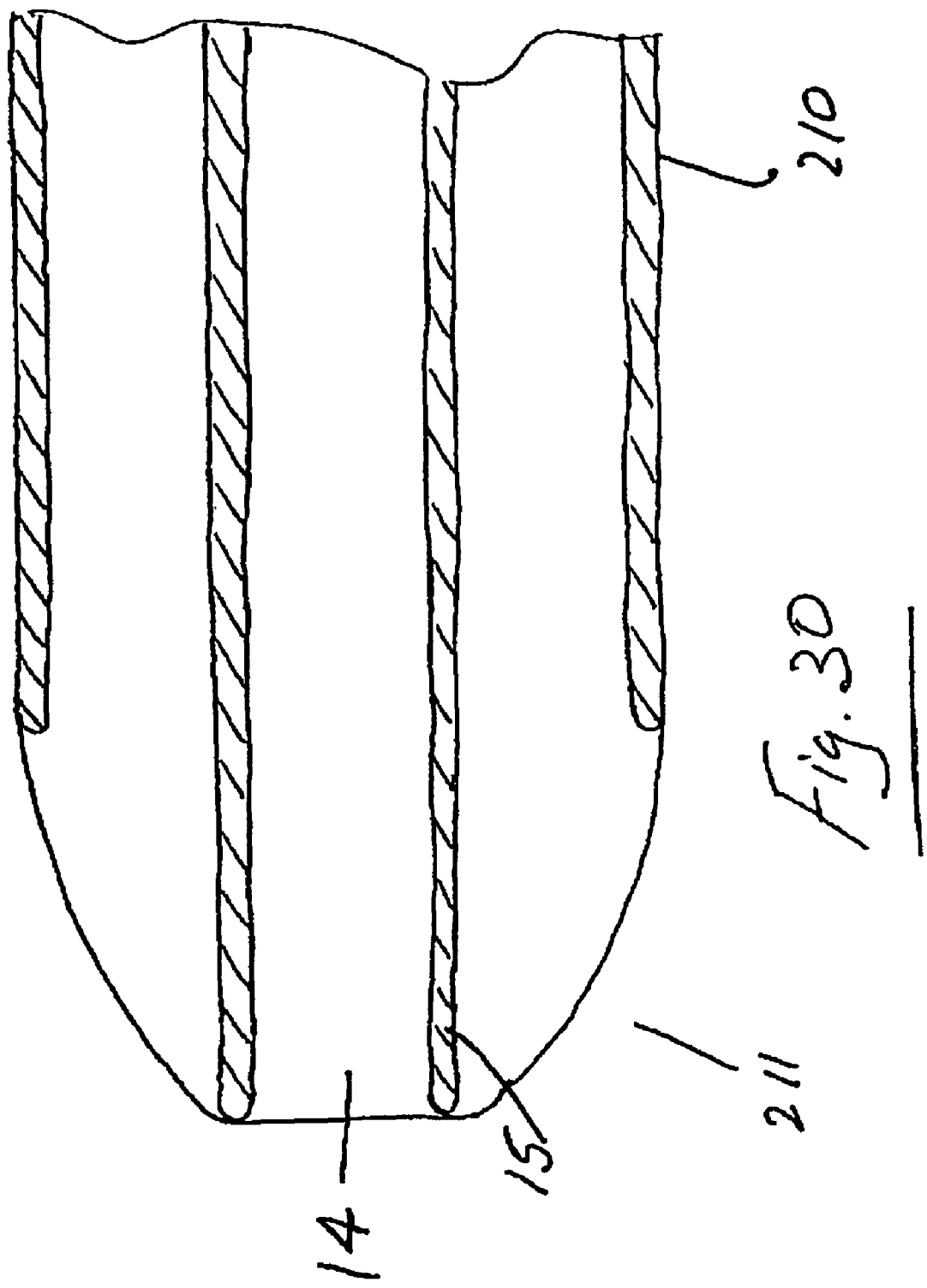
FIG. 30 is a longitudinal cross sectional view of the distal end of the catheter of FIG. 29.
Figure 31:
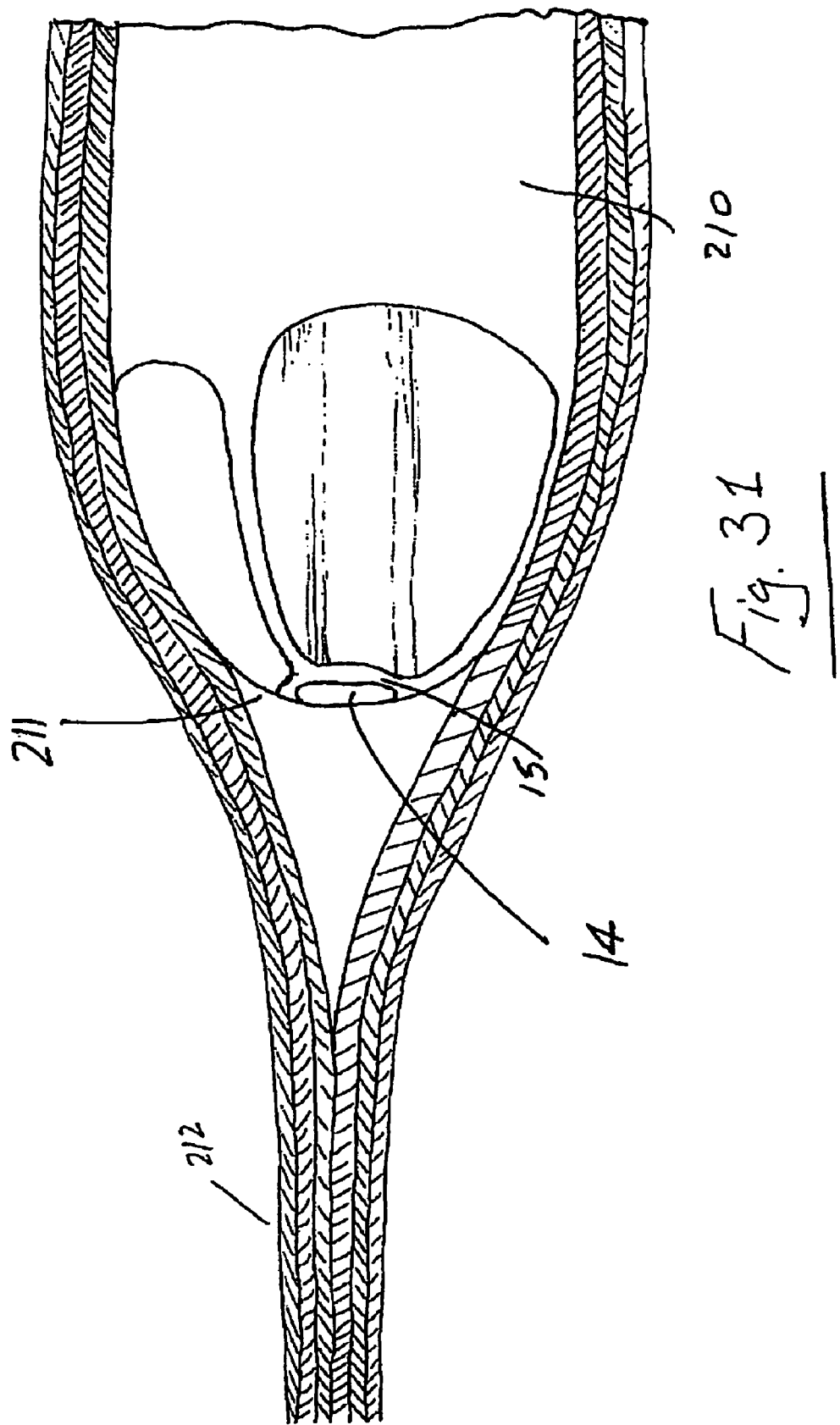
FIG. 31 is an elevational, partially cross sectional view of the distal end of the catheter of FIGS. 29 and 30 being inserted into a vein.
Figure 32:
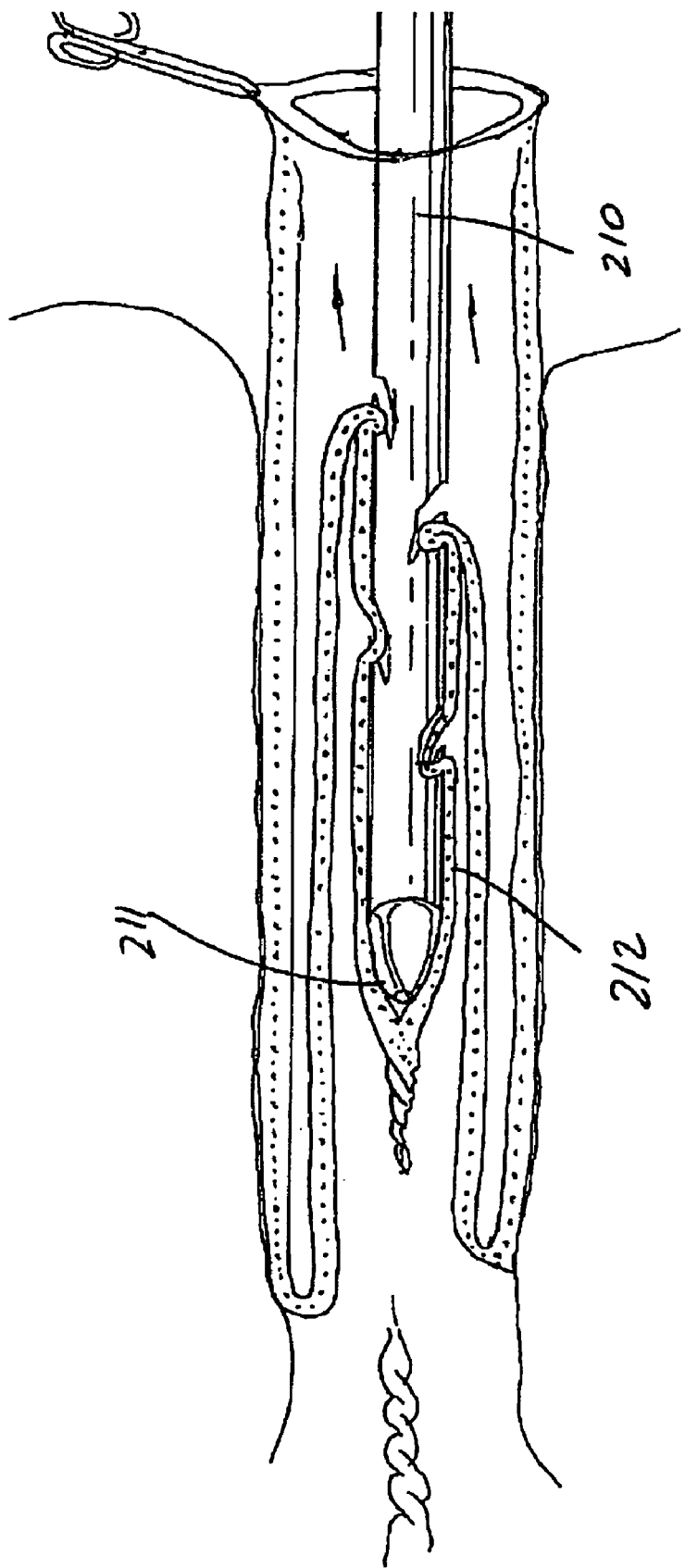
FIGS. 32 to 34 are cross sectional views of the vein stripping device in various stages of use.

Referring to FIGS. 29 and 30 there is illustrated the distal end of a further vein stripping catheter 210 in which parts similar to those described above are assigned the same reference numbers. In this case the tapered distal tip 211 is further elongated to further aid ease of insertion of the distal tip 211 into a view 212 as illustrated in FIGS. 31 and 32. The vein 212 has three layers—the intima, the media and the advantitia. The device facilitates stripping of the sub-adventitial layers. In FIG. 31 the vein is shown suctioned into the tip, the blood having being previously suctioned out through the tip.

Figure 33:
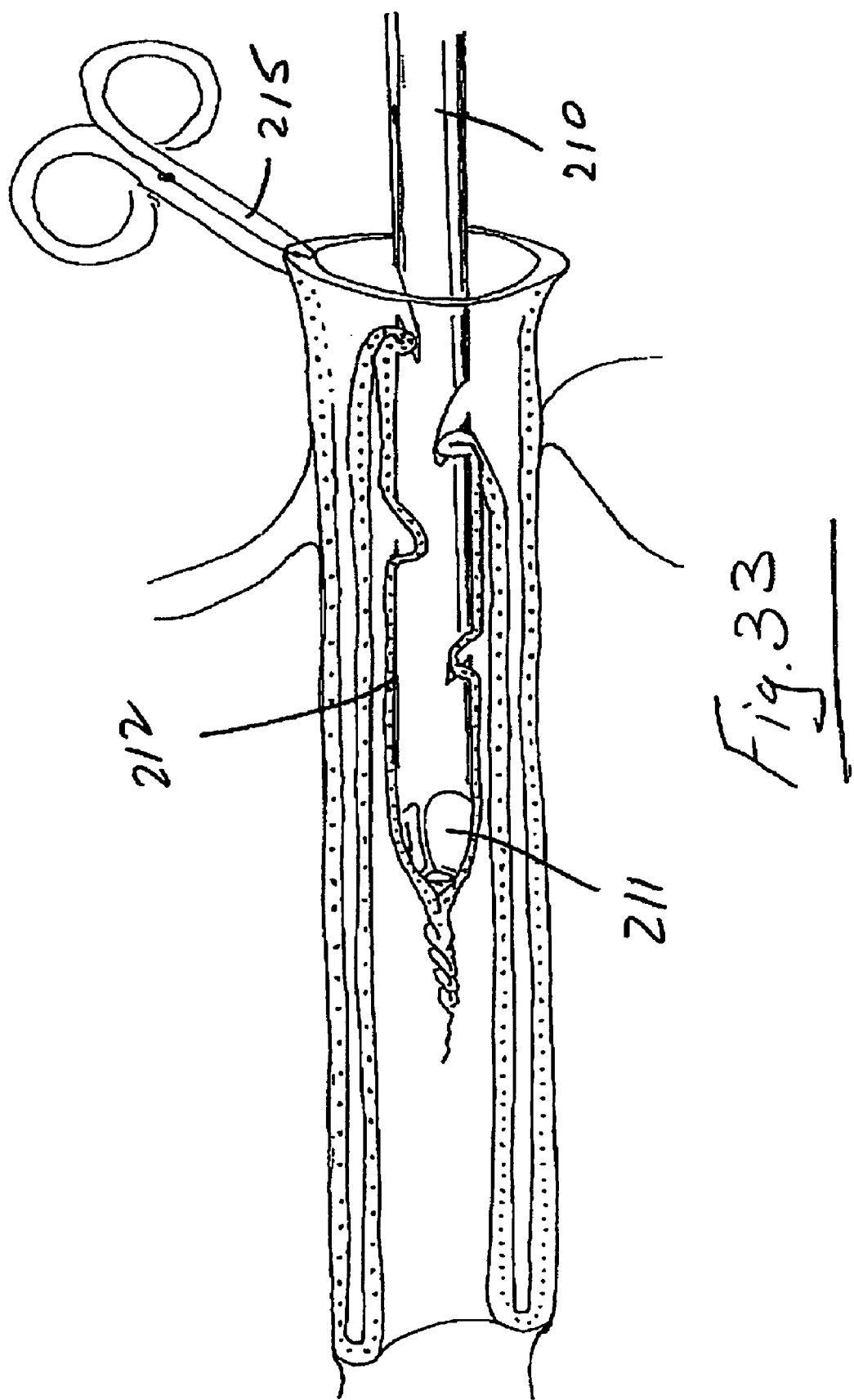
Figure 34:
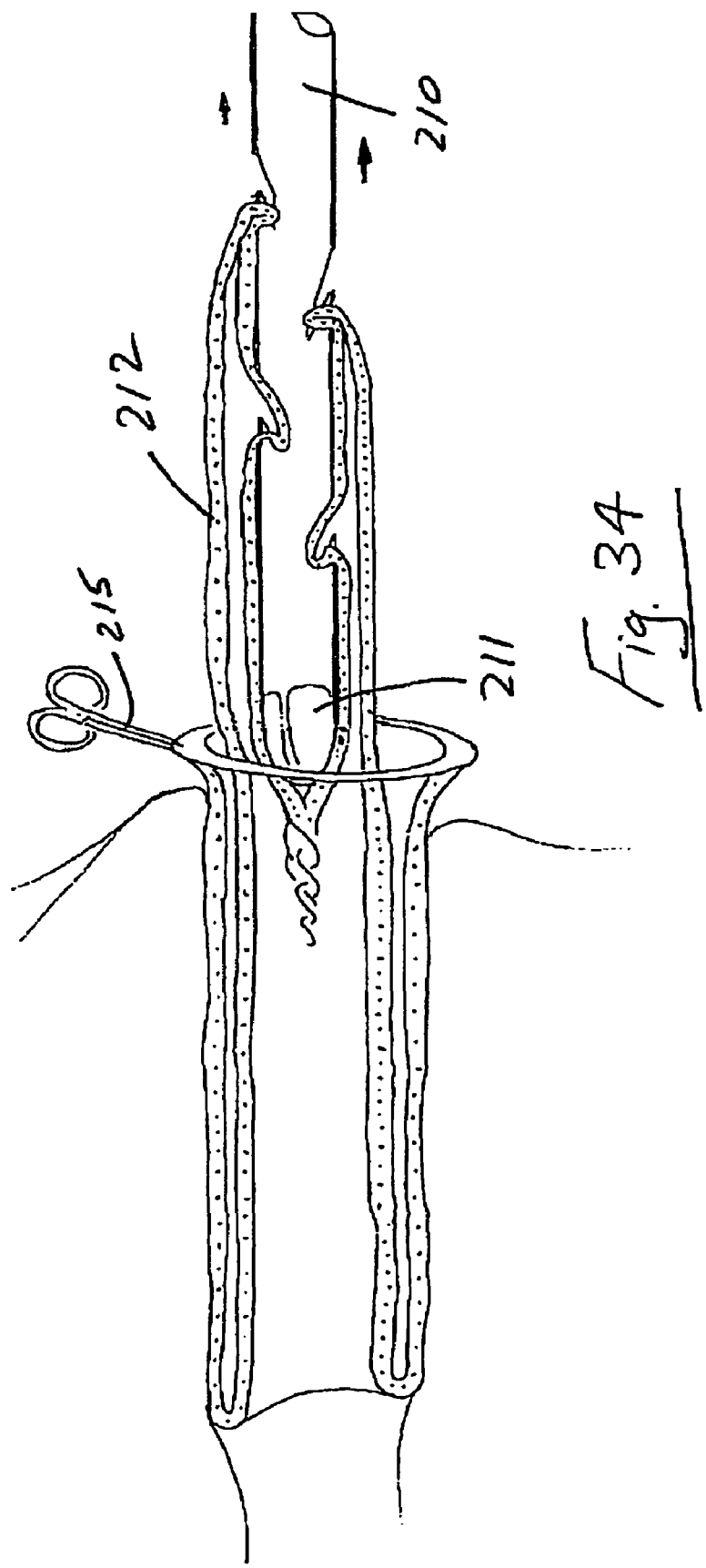

The device is shown in various configurations of use in FIGS. 32 to 34. In FIG. 32 the vein 212 has been evacuated of blood, suctioned onto the catheter, twisted and pulled to detachment. In FIG. 32 the vein is shown peeling away from surrounding membrane or advantitia as it is pulled out. FIG. 33 shows the progression of vein removal as it peels away under tension at the proximal end. In this case the vein 212 is shown being held by small clamps 215 at the proximal end. In FIG. 34 the vein 212 is almost completely removed, fully intact as it is peeled away while invented. It will be noted that the vein is note shredded but rather remains intact.

Figure 35:
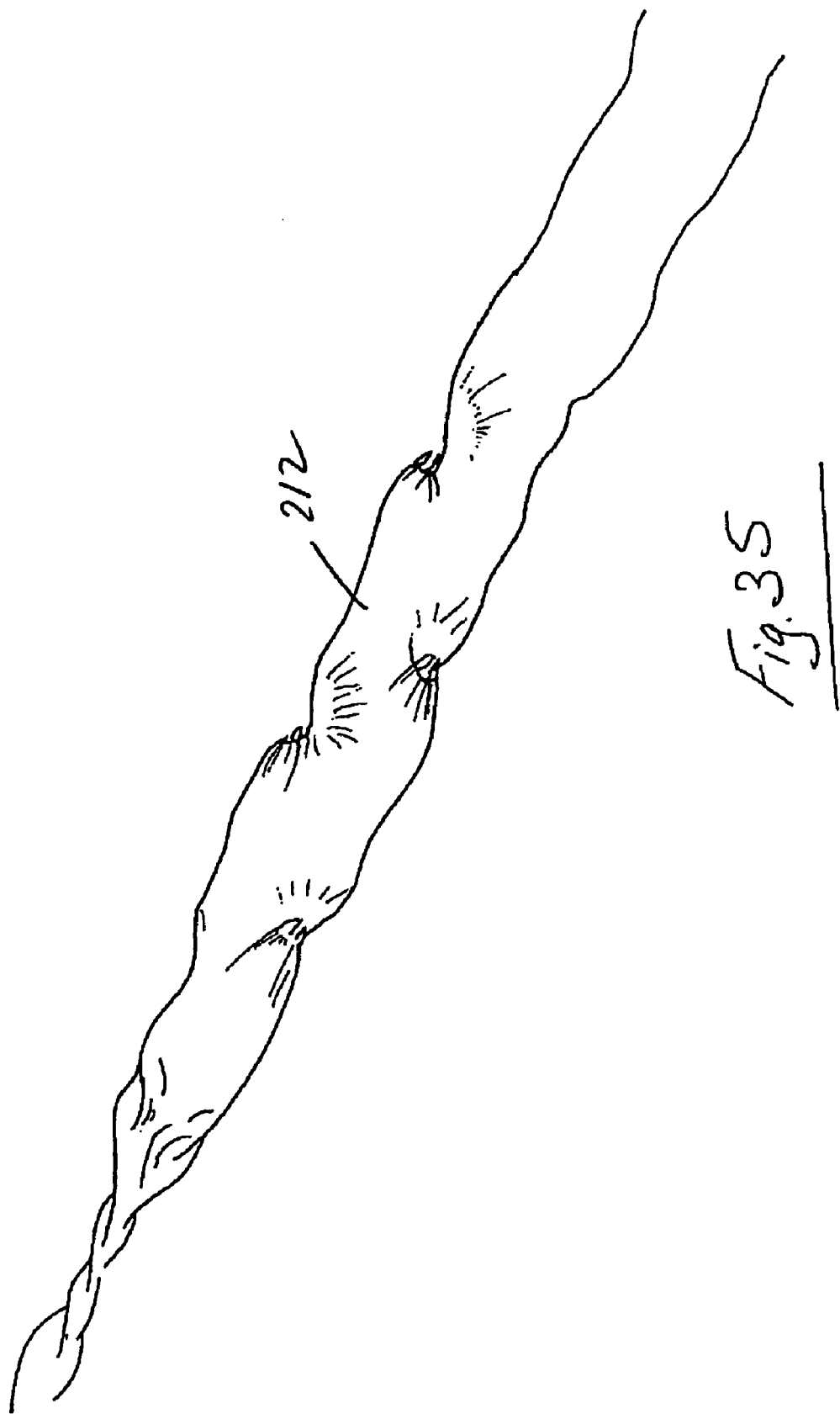
FIG. 35 is an isometric view of a vein gripped by the vein stripping device.
Figure 36:
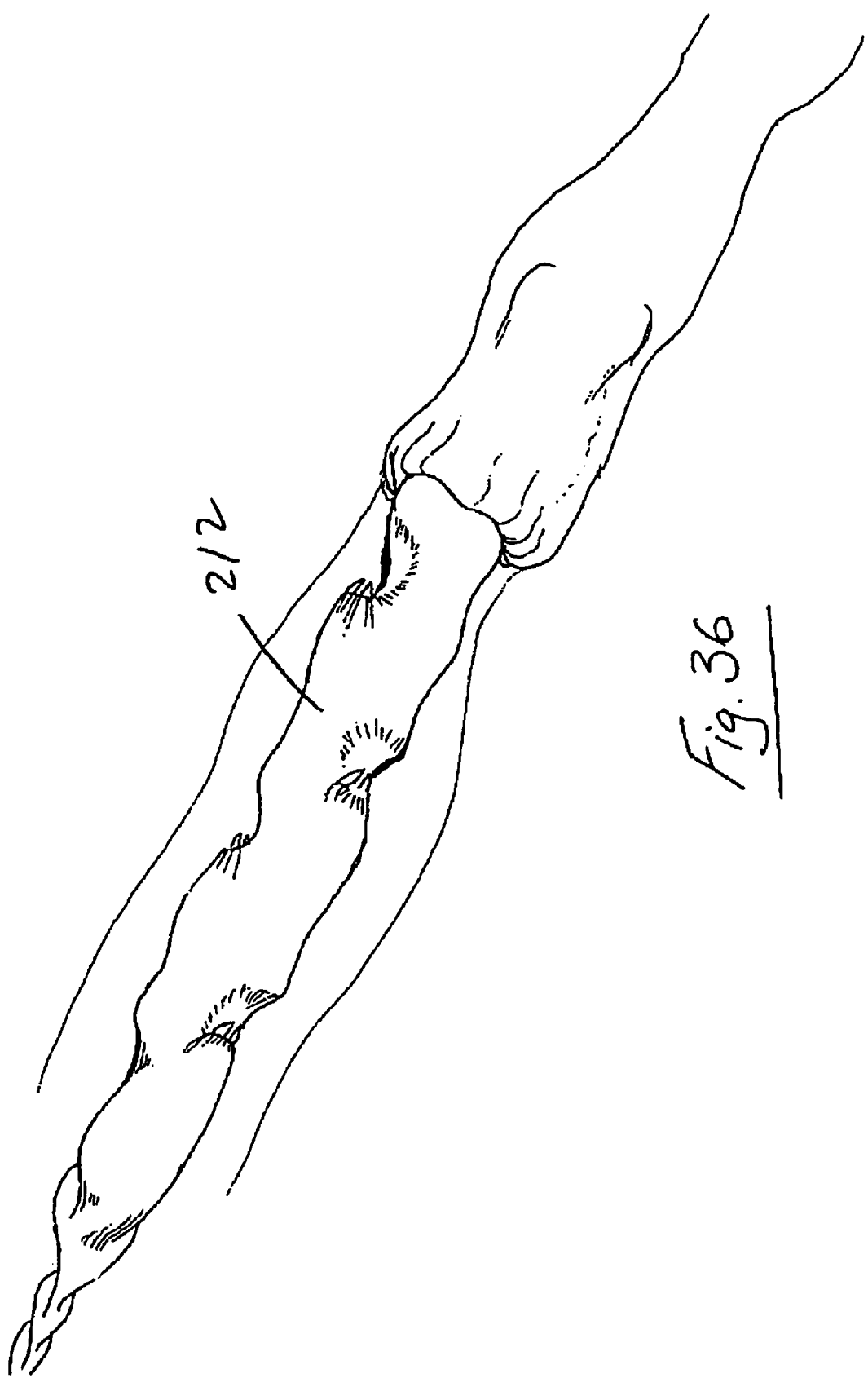
FIG. 36 is an isometric view illustrating the pulling of the vein when gripped by the vein stripping device and the partial inversion of the vein.
Figure 37:
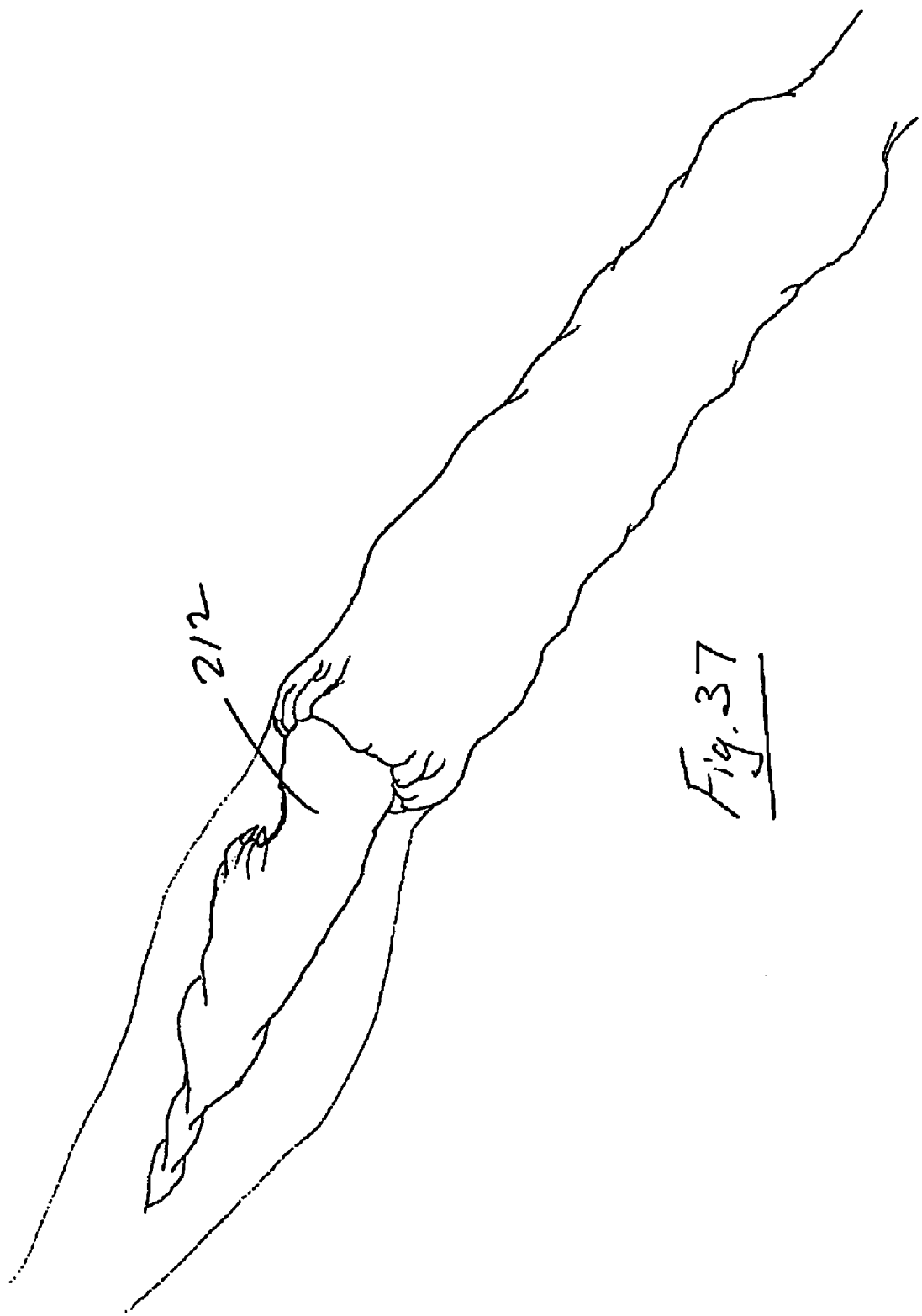
FIG. 37 is an isometric view similar to FIG. 36 illustrating further inversion of the vein.
Figure 38:
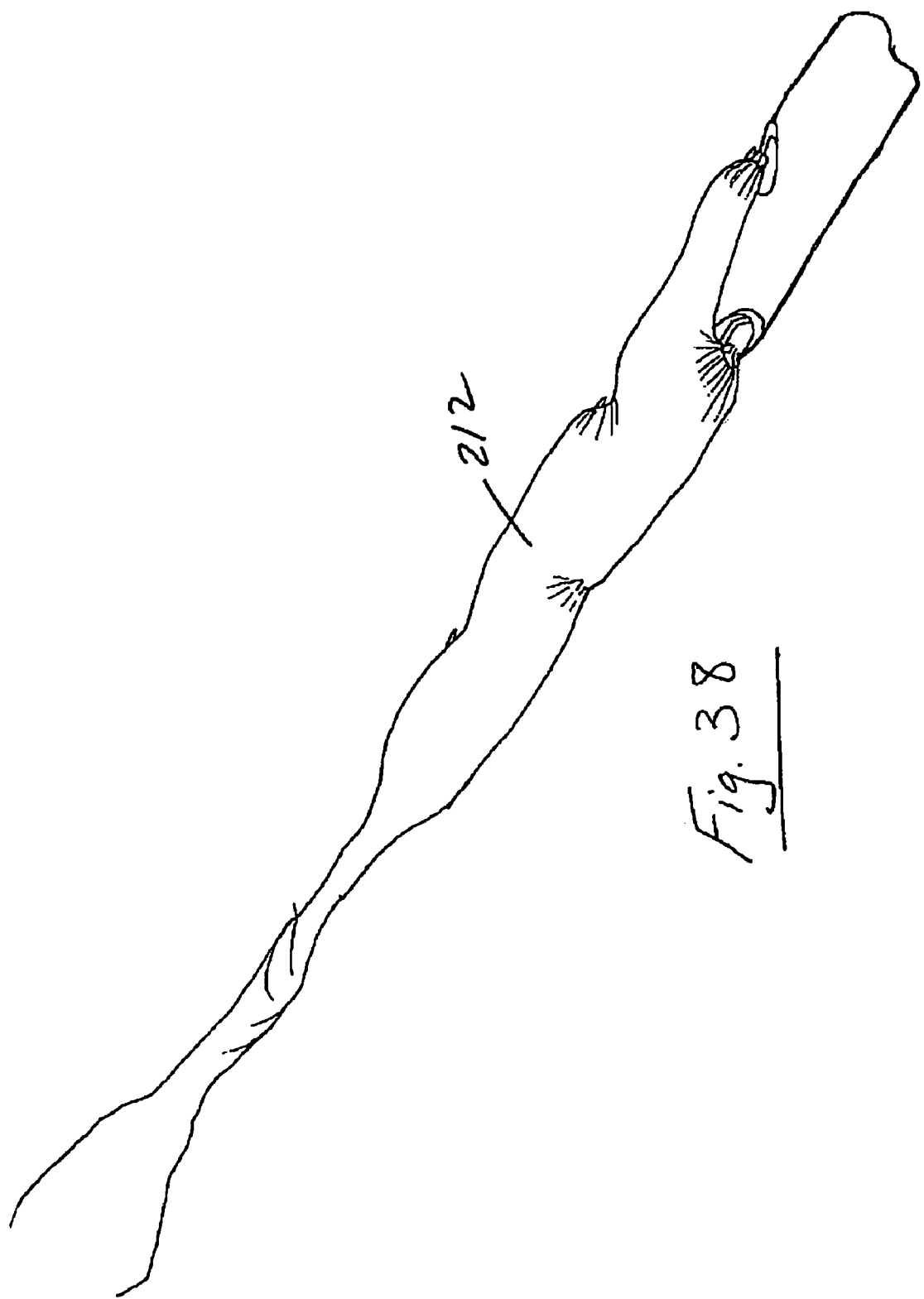
FIG. 38 is an isometric view of the vein almost completely inverted.
Figure 46:
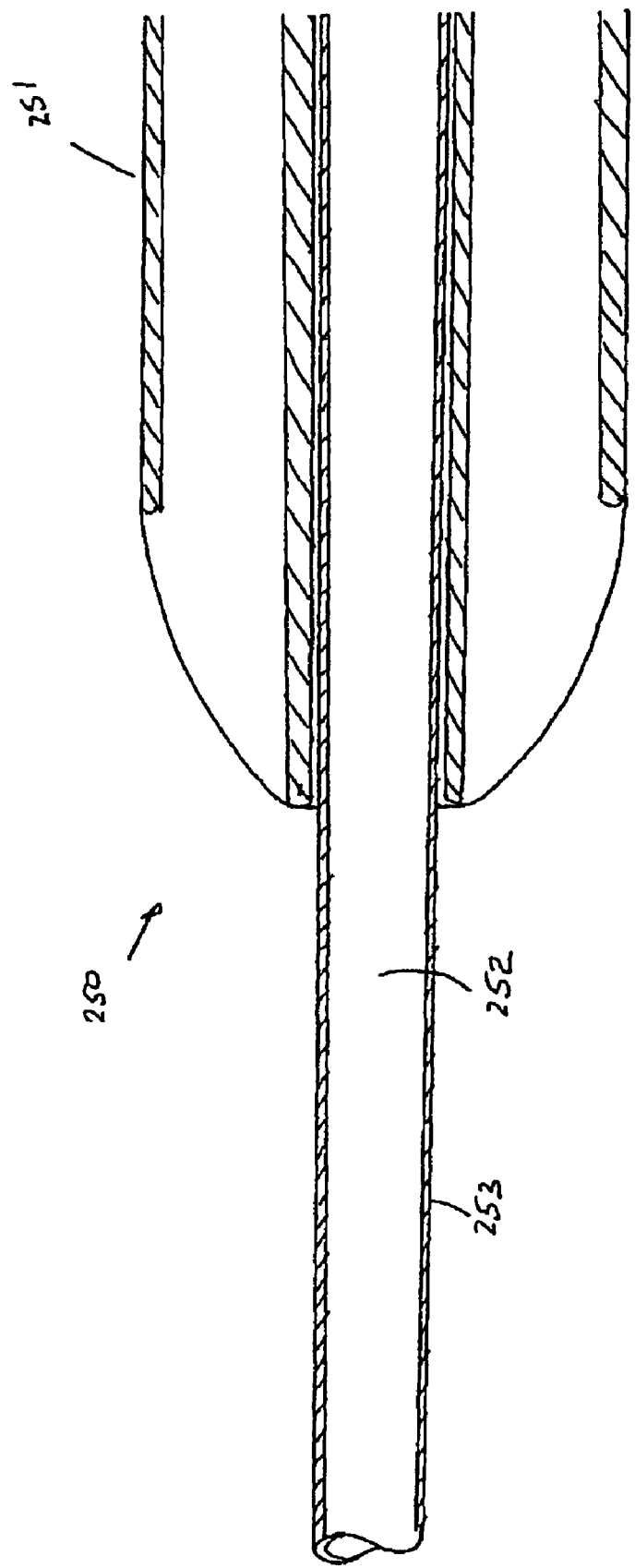
FIG. 46 is a cross sectional view of a distal tip of another vein stripping device of the invention.
Figure 47:
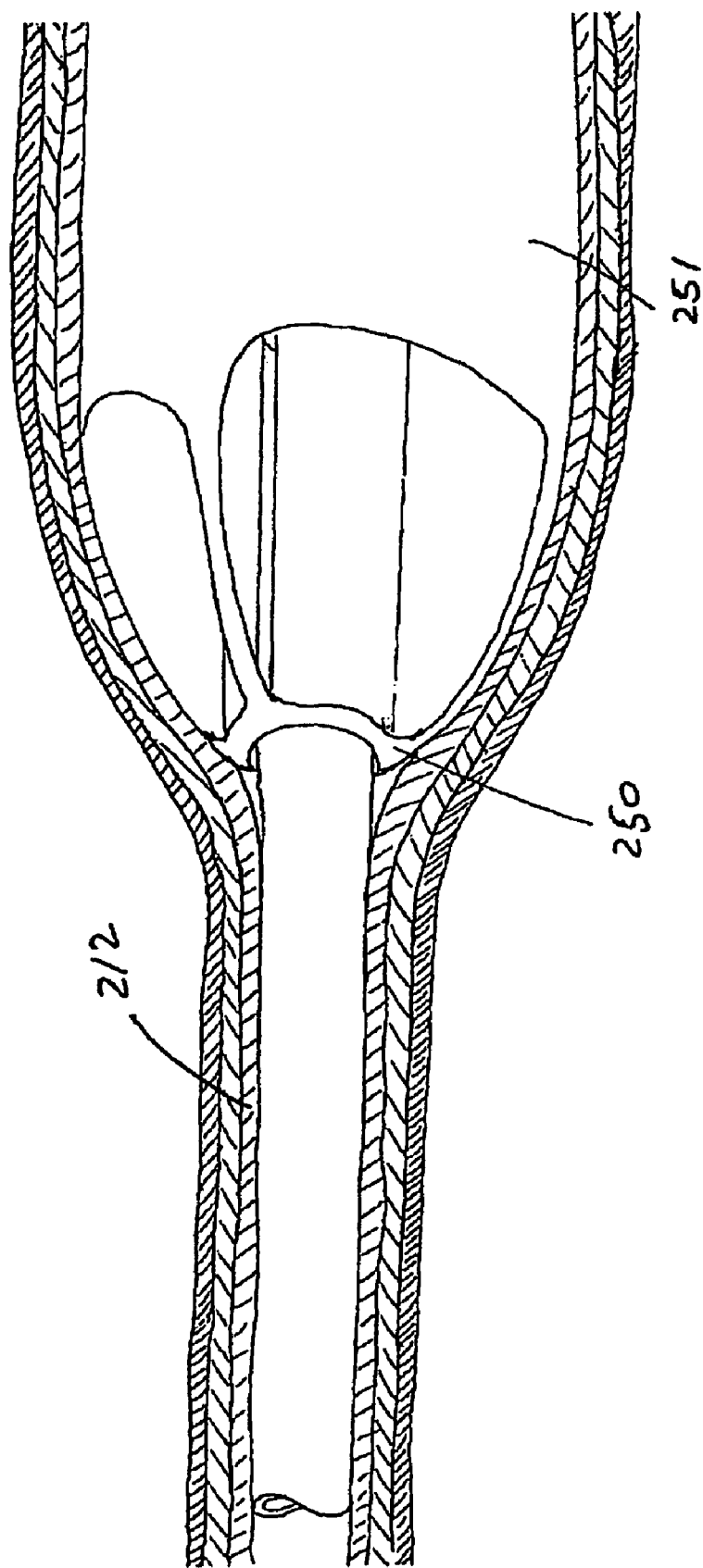
FIG. 47 is a cross sectional view of the device of FIG. 46 inserted into a vein.
Figure 48:
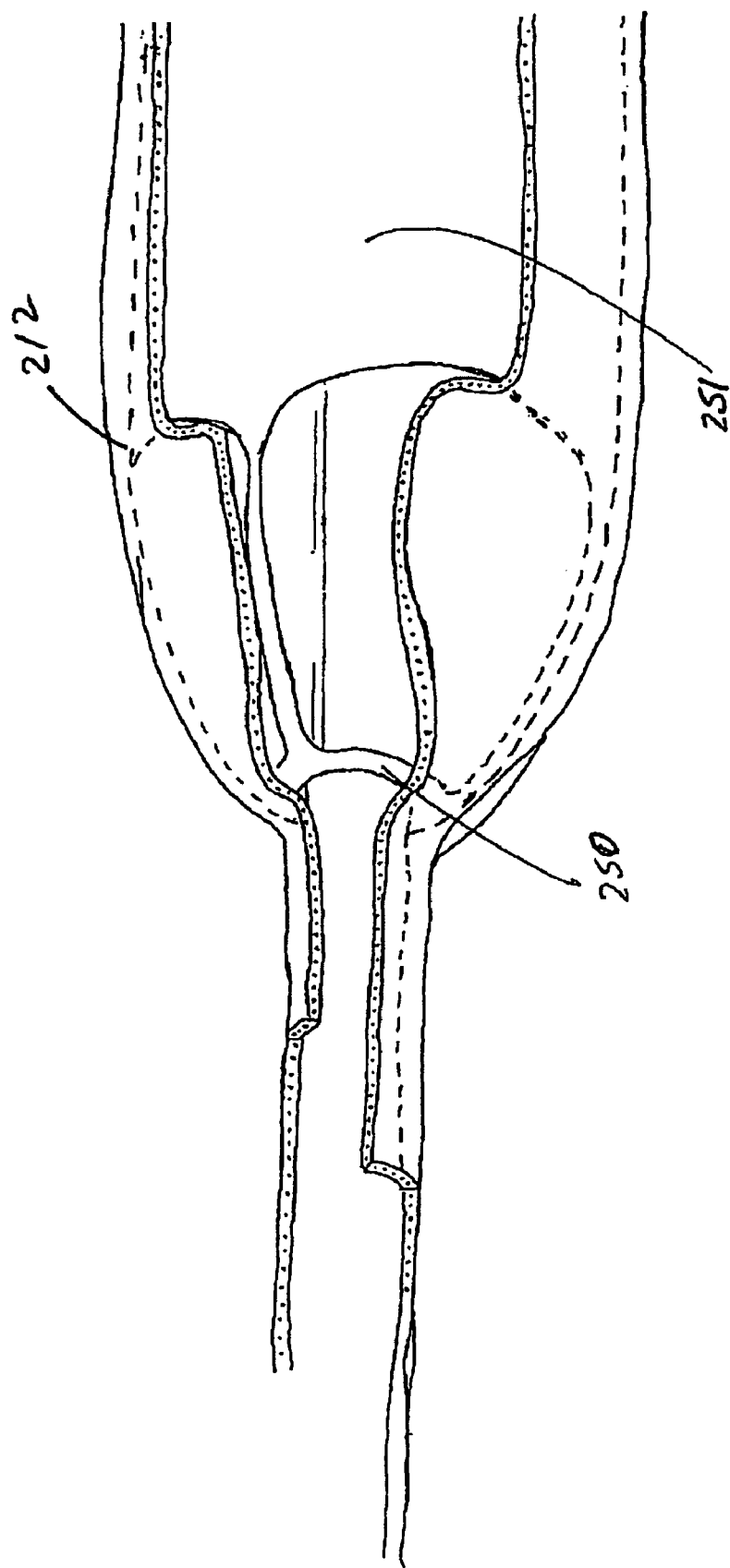
FIG. 48 is an isometric, partially cut-away view of the device of FIGS. 46 and 47 in use.
Figure 49:
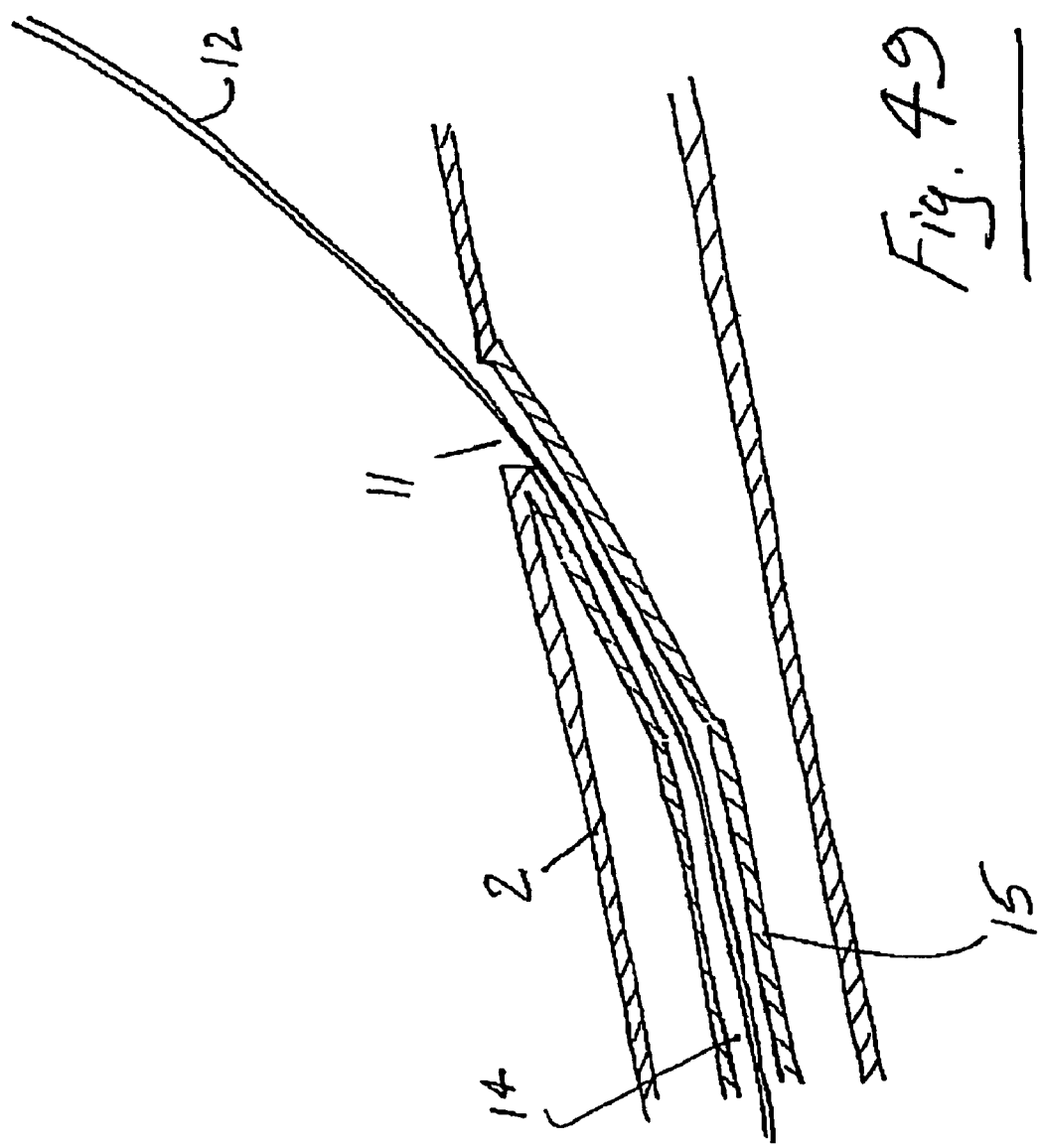
FIG. 49 is a cross sectional view of a proximal region of a vein stripping device.
Figure 50:
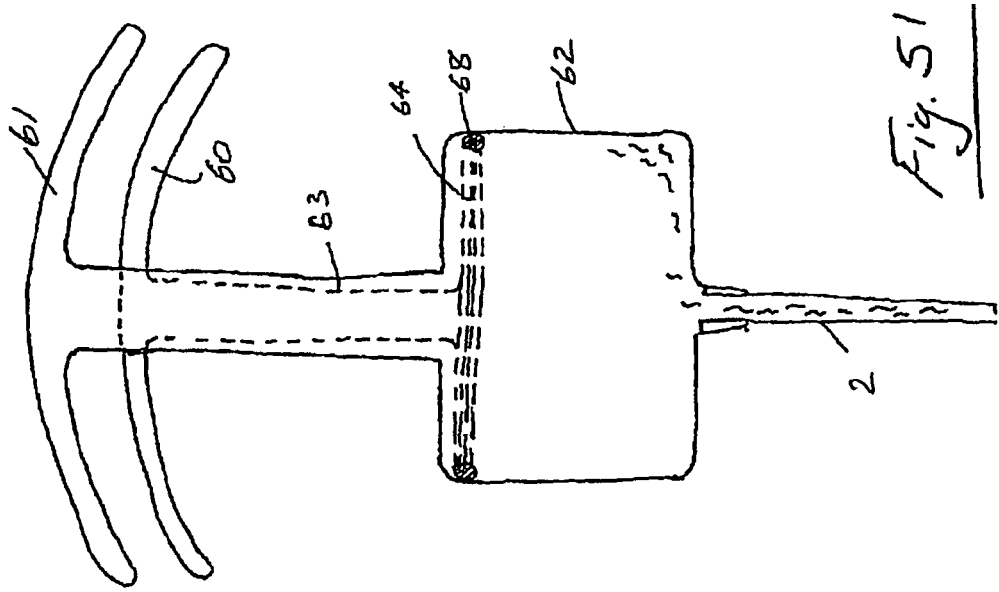
Figure 51:
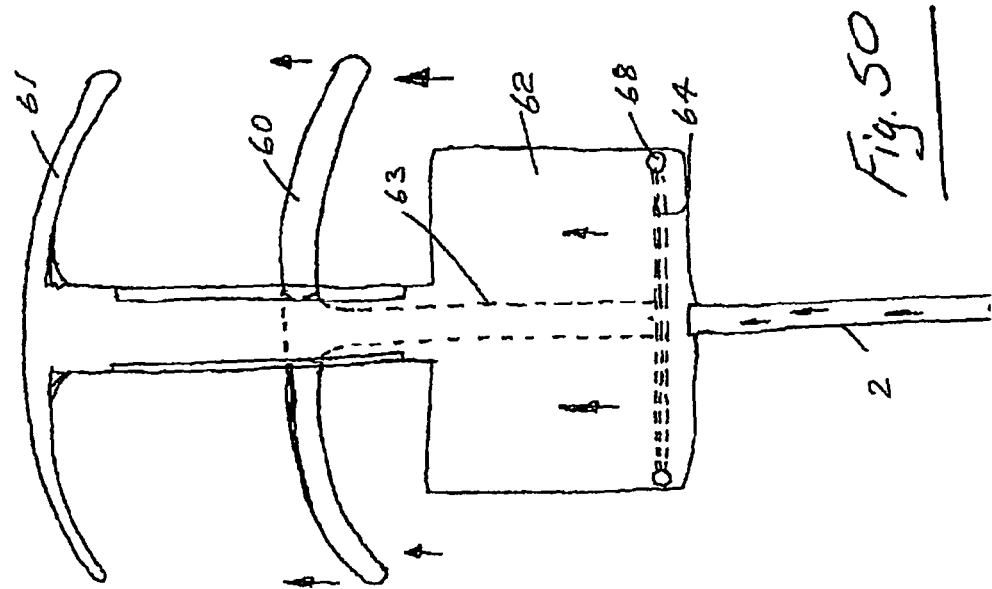

FIGS. 35 to 38 further illustrate the stripping of the vein 212 using the devices of the invention. In FIG. 35 a vein is gripped on the grip features and at the distal end as a result of the vacuum within the catheter. It can be readily twisted and pulled to detachment whilst remaining intact. The vein 212 is pulled and inverted through the channel (FIG. 36). The vein 212 further inverts as a pulling force is applied at the proximal end (FIG. 37). Finally (FIG. 38) the vein 212 is completely inverted and pulled clear of the leg.

Referring to FIGS. 39 to 41 there is illustrated another device 100 according to the invention which is similar to the device described above and like parts are assigned the same reference numerals.

In this case the device comprises a dynamic or kinematic vein gripping means. In this case the vein gripping means is provided by a gripping element 101 which is pivotal about a pivot pin 102 which extends across the hole 99 in the tubular member 2. The gripping element 101 has a vein gripping end 103 which is engagable with a vein 10 when suction is applied as illustrated in FIG. 41. When no suction is applied the gripping element 101 is in the rest position illustrated in FIG. 40.

Such kinematic vein gripping features move and lock in a more positive gripping and capturing position.

This is an example of a device in which the vein or subadvantitial layers of the vein may be gripped where in the force of the vein being suctioned into the cather causes a grip feature to kinematically displace into a gripping position when the assembly is pulled in the proximal direction.

Referring to FIGS. 42 to 45 there is illustrated another kinematic vein gripping feature which is activated by vacuum. In this case the vein 10 is pulled over one end to pivotally move the other end to grip and clamp the vein. In the configuration of FIGS. 42 and 43 there is no suction in the lumen and the vein lies along the outer wall of the catheter, overlying the grip features. When suction is actuated (FIGS. 44 and 45) the vein is sucked in and the sharp end of the grip feature 103 may project out as it pivots. In this case the kinematic grip features are integral with the catheter.

The grip means may be pivotally mounted on either the lumen wall or the lumen ribs so that the tip can move to project from the lumen surface by no more than 0.3 mm and only after the vacuum is applied. This provides a more positive grip on the vein.

Referring to FIGS. 46 to 49 there is illustrated the distal end 250 of another vein stripping catheter 251 of the invention. In this case the device comprises a guiding lumen 252 defined by an inner tube 253 which extends distally of the catheter tip 250. The guiding lumen 252 extends through the catheter to an exit port which may be at the proximal end of the device or at a distance distal from the proximal end (FIGS. 3 and 49) for rapid exchange. The device may be delivered over a guidewire. The device is free to move along the inner tube 253 or a guidewire.

It will be appreciated that in the device all of the vein gripping features may be the same or different. For example, the vein gripping features adjacent to the distal end of the catheter may be enlarged or enhanced for added gripping. The size, configuration and/or location of the vein gripping features may vary along the length of the device.

Referring especially to FIGS. 50 to 53 the proximal end 4 of the device comprises a first movable handle 60 and a second fixed handle 61. The proximal handle 60 is used to draw a vacuum in the catheter. The vacuum generating system in this case represents an inverse syringe which functions so that the intuitive squeezing of the handles 60, 61 and pulling out the vein stripper device with a single hand creates a vacuum through the lumen extending into the vein 10.

There is a reservoir 62 extending from the fixed handle. The movable handle 60 has a tubular extension 63 to which a plunger 64 is attached. The plunger 64 is located within the reservoir 62 with an O-ring seal 68 therebetween. The catheter 2 is attached to the reservoir 62.

When the handles 60, 61 are drawn together as illustrated in FIG. 52 blood is drawn up through the catheter 2 and collected in the reservoir 62. The plunger 64 is pushed through the reservoir 62 and draws the content of the catheter 2 into the reservoir 62. The plunger 64 is sealed against the wall of the reservoir. In this manner it applies the vacuum resulting in the contents of the catheter being drawn into the reservoir 62.

Figure 54:
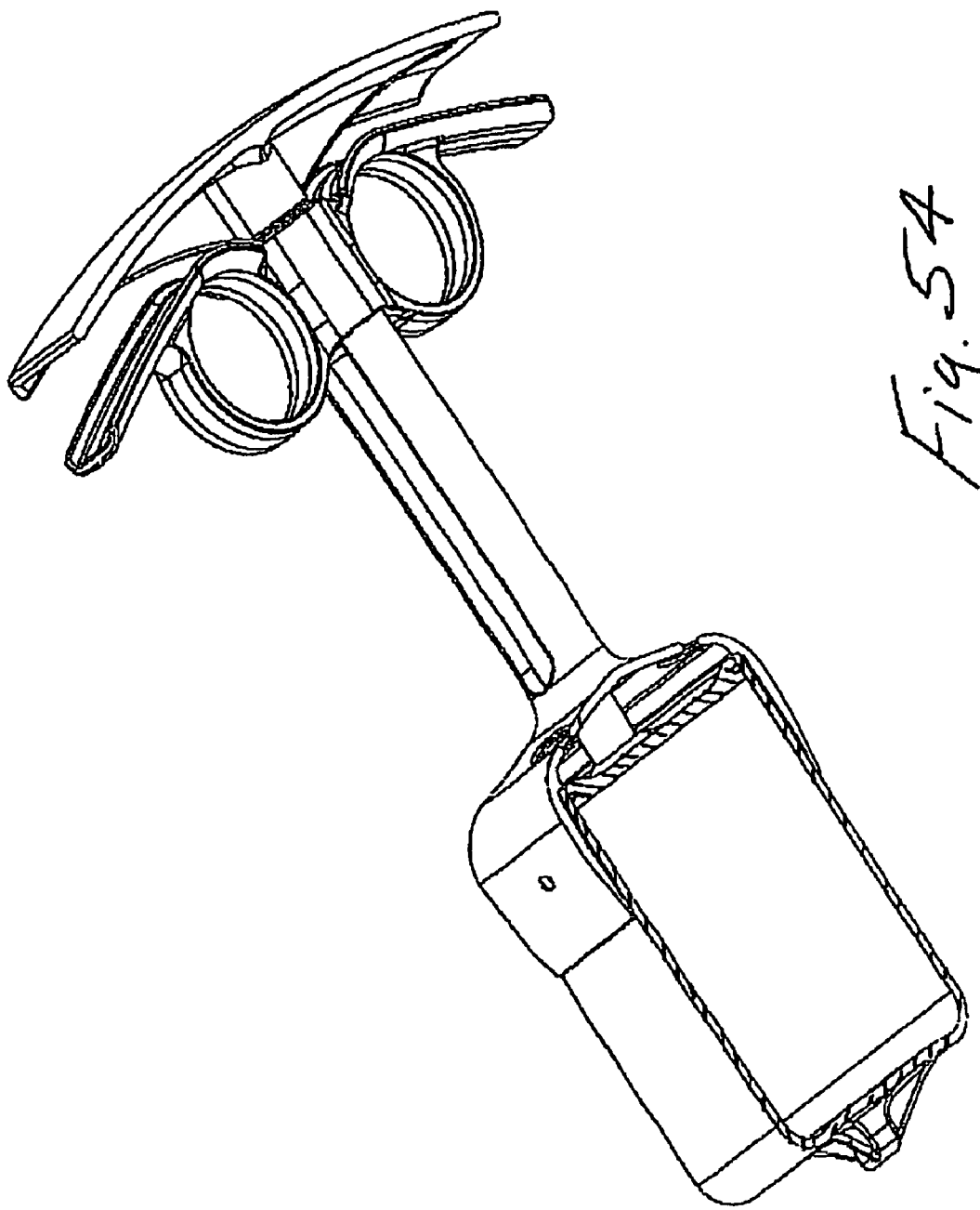
FIG. 54 is an isometric partially cross sectional view of a vacuum generator for the device.
Figure 56:
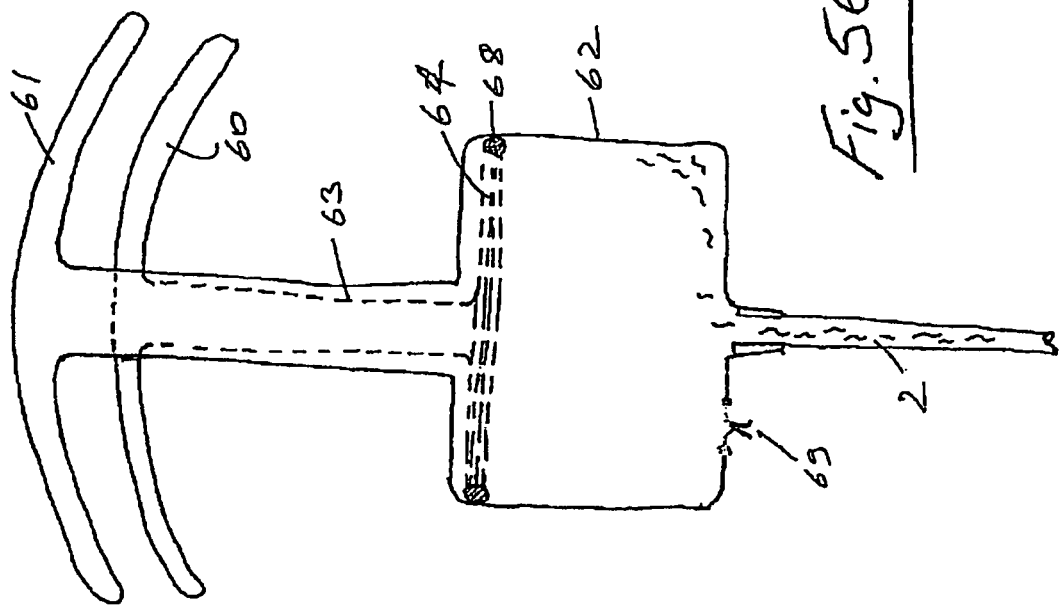
Figure 55:
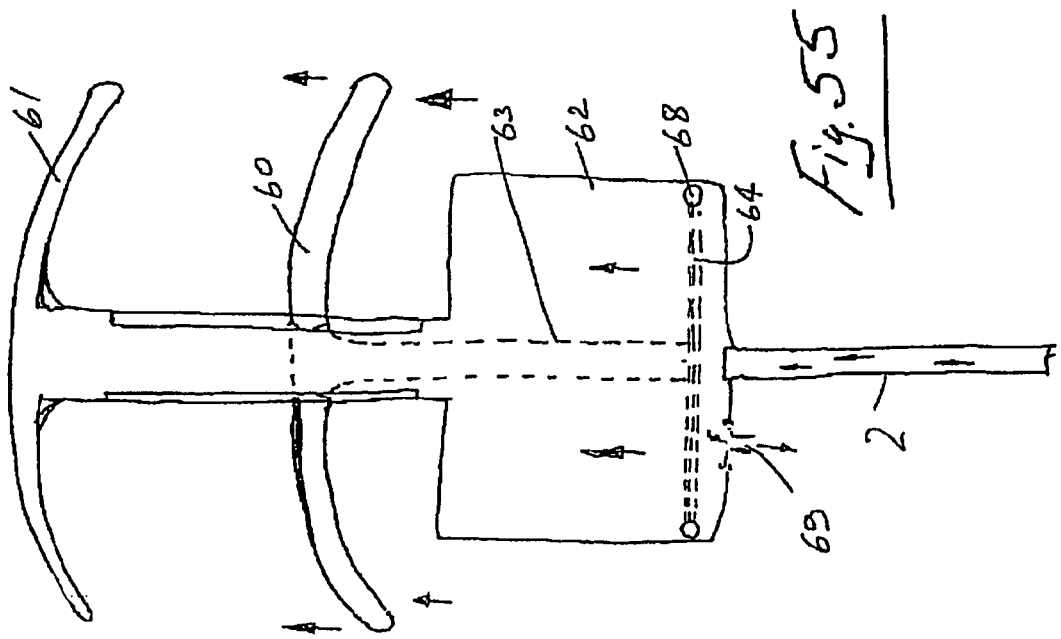

FIG. 54 illustrates a version of the device in which the handle 60 has finger loops.

Referring to FIGS. 55 to 58 in this case the chamber has a blood outlet which is closed by a one way valve such as a lipseal valve 69. As the plunger 64 is being drawn up through the chamber 62 the valve closes to maintain the vacuum. As the lumen is being inserted then the blood is free to travel into and through the device because air in the lumen will vent through the valve 69. When the vein is being removed the valve 69 is closed in order to maintain the intensity of the vacuum.

Referring to FIGS. 59 to 63 there is illustrated another vacuum generating means 300 comprising a proximal tube 301 connected to the proximal region of the catheter 2 and a proximal blood collecting housing defining a chamber 302. The proximal tube 301 extends through the blood collecting housing 302. A plunger 303 is movable through the housing 302 to generate a vacuum in the catheter 2. A plunger tube 304 is connected to and extends proximally of the plunger 303. The plunger tube 304 has an opening 305 through which blood from the proximal tube 301 passes into the chamber 302 proximally of the plunger. A first handle 310 is connected to the plunger tube 304 and a second handle 311 is connected to the housing 302. One of the handles 310, 311 is moved relative to the other handle to move the plunger through the housing. In this case a movable handle is moved towards the other handle to move the plunger 303 through the housing 302. The system incorporates a non return valve means 315 for venting of the catheter. The non return valve means 315 is normally open and is closed on operation of the plunger 303.

Figures 59, 60:
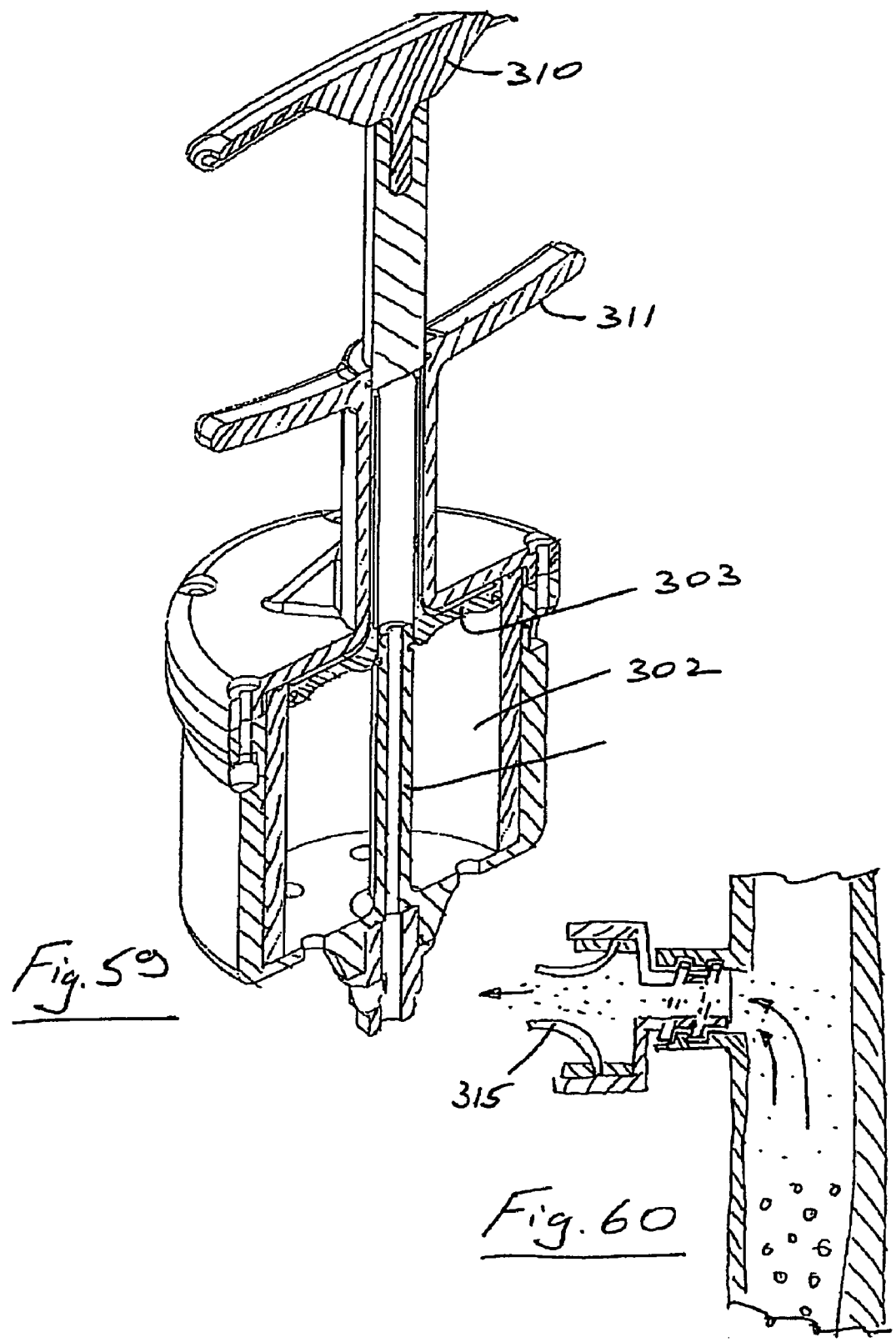
FIG. 59 is an isometric partially cut-away cross sectional view of a vacuum generator for the device in one position.
FIG. 60 is an enlarged cross sectional view of a valve feature of the device of FIG. 59.

The vacuum generating means is in the start configuration in FIGS. 59 and 60 with the plunger 303 at the primal end of the chamber 302. The valve 315 is open to facilitate venting of air from the catheter as illustrated in FIG. 60. As the handles 310, 311 are moved towards one another the plunger 303 is advanced through the chamber 302. The valve 315 closes, ensuring that blood flows up through the catheter 2 and the proximal tube 301 and through openings or slots 305 in the plunger tube 304 and into the chamber 302 behind (proximal to) the plunger 303 as illustrated in the intermediate configuration shown in FIG. 63.

Figures 61, 62:
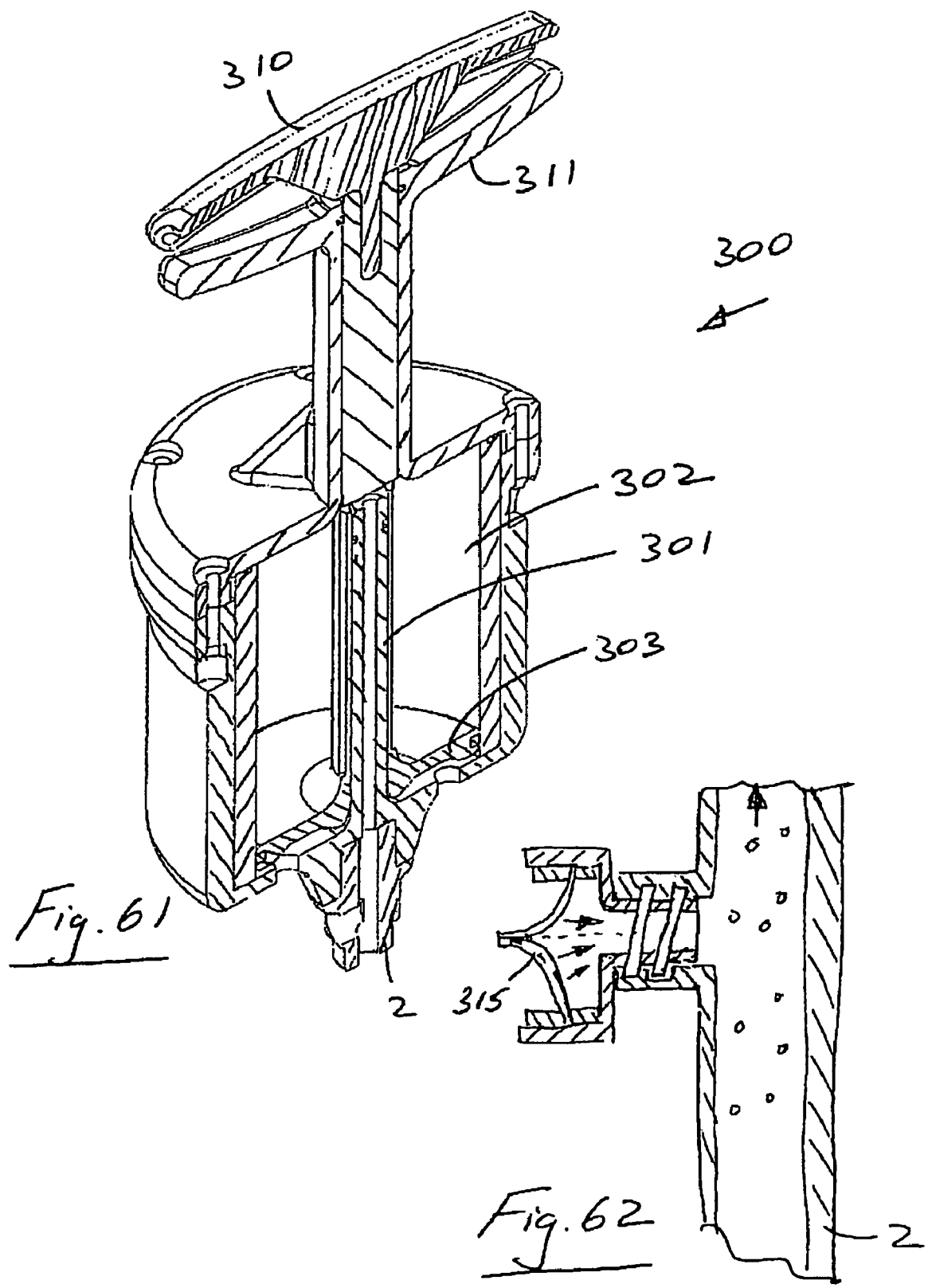
FIG. 61 is a view similar to FIG. 59 with the device in another position of use.
FIG. 62 is an enlarged cross sectional view of a valve feature of the device of FIG. 61.
Figure 63:
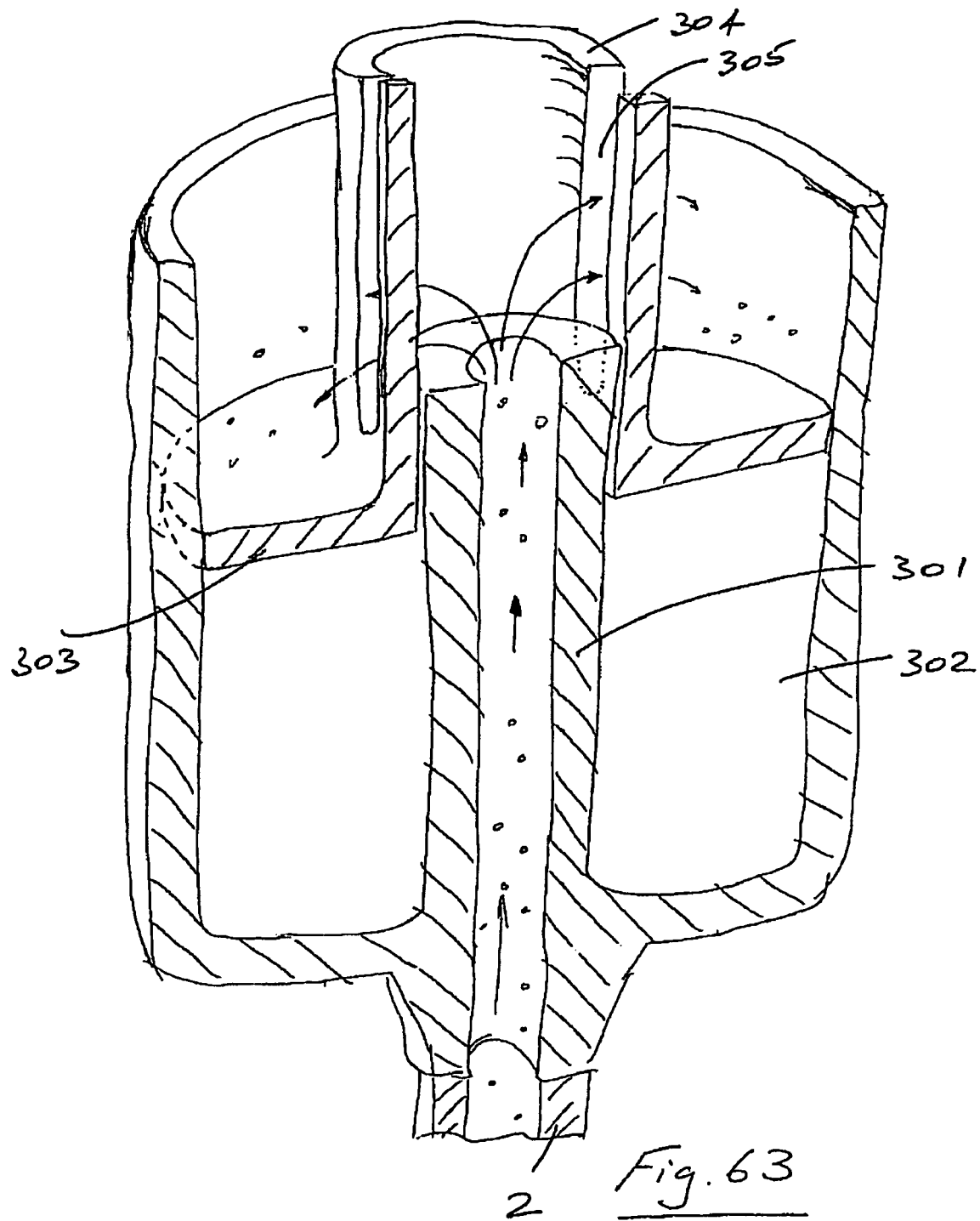
FIG. 63 is an enlarged cut-away view of the device of FIGS. 59 to 62.

In the configuration illustrated in FIG. 61 the plunger 303 has traveled through the chamber 302 and the blood has collected in the chamber 302 behind the plunger 303. The system is relatively easy to use in a controlled manner during the vein stripping procedure.

Figure 64:
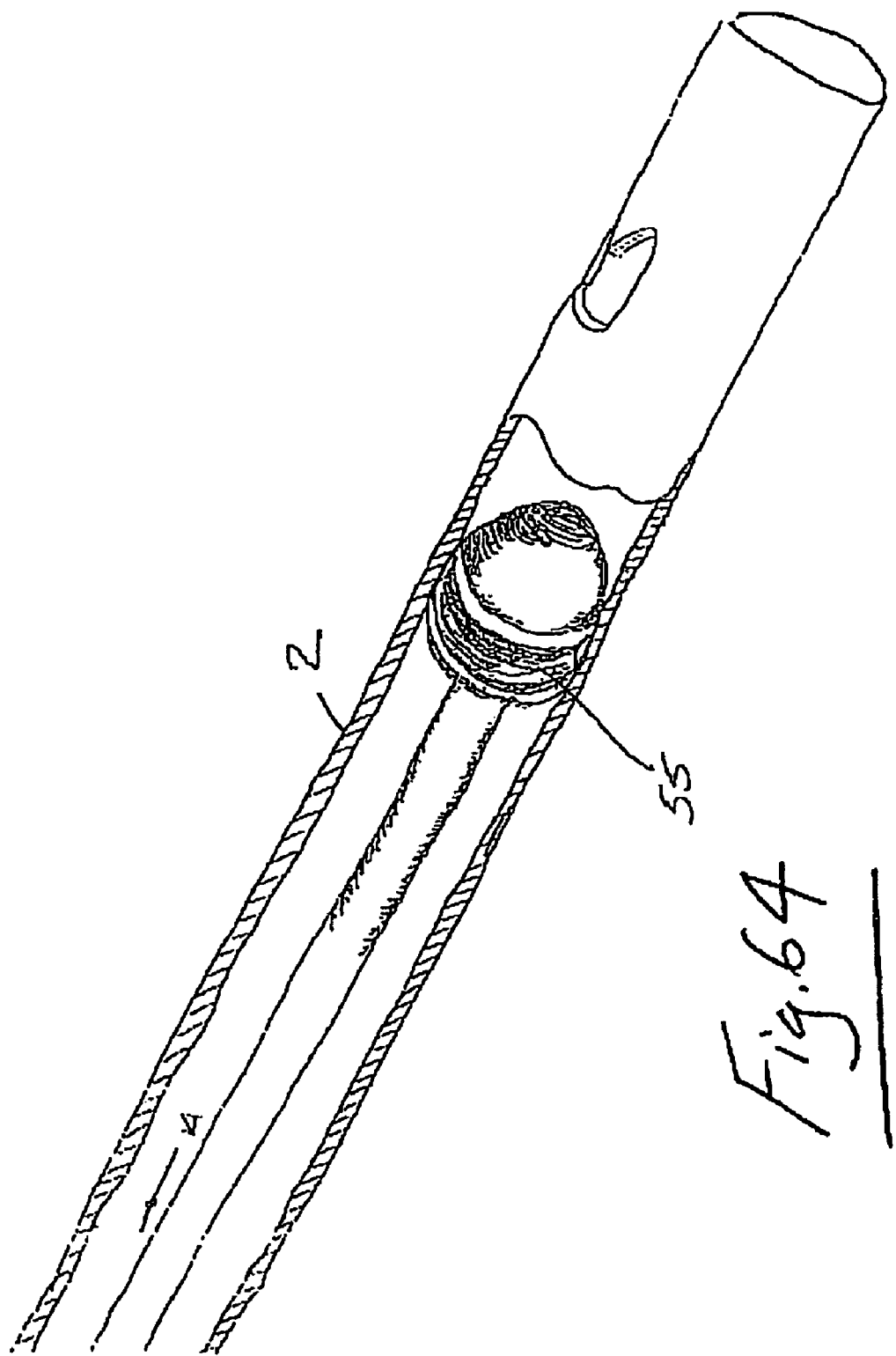
FIG. 64 is an isometric, partially cut-away view of another vacuum generating system.

Another vacuum generating system is illustrated diagrammatically in FIG. 64. In this case a plunger 55 extends through the catheter 2. As the plunger 55 is moved proximally in the direction of the arrow A, a vacuum is generated at the distal end and within the catheters from where the plunger 55 has traveled. The vacuum increases as the plunger is retracted proximally.

Figure 65:
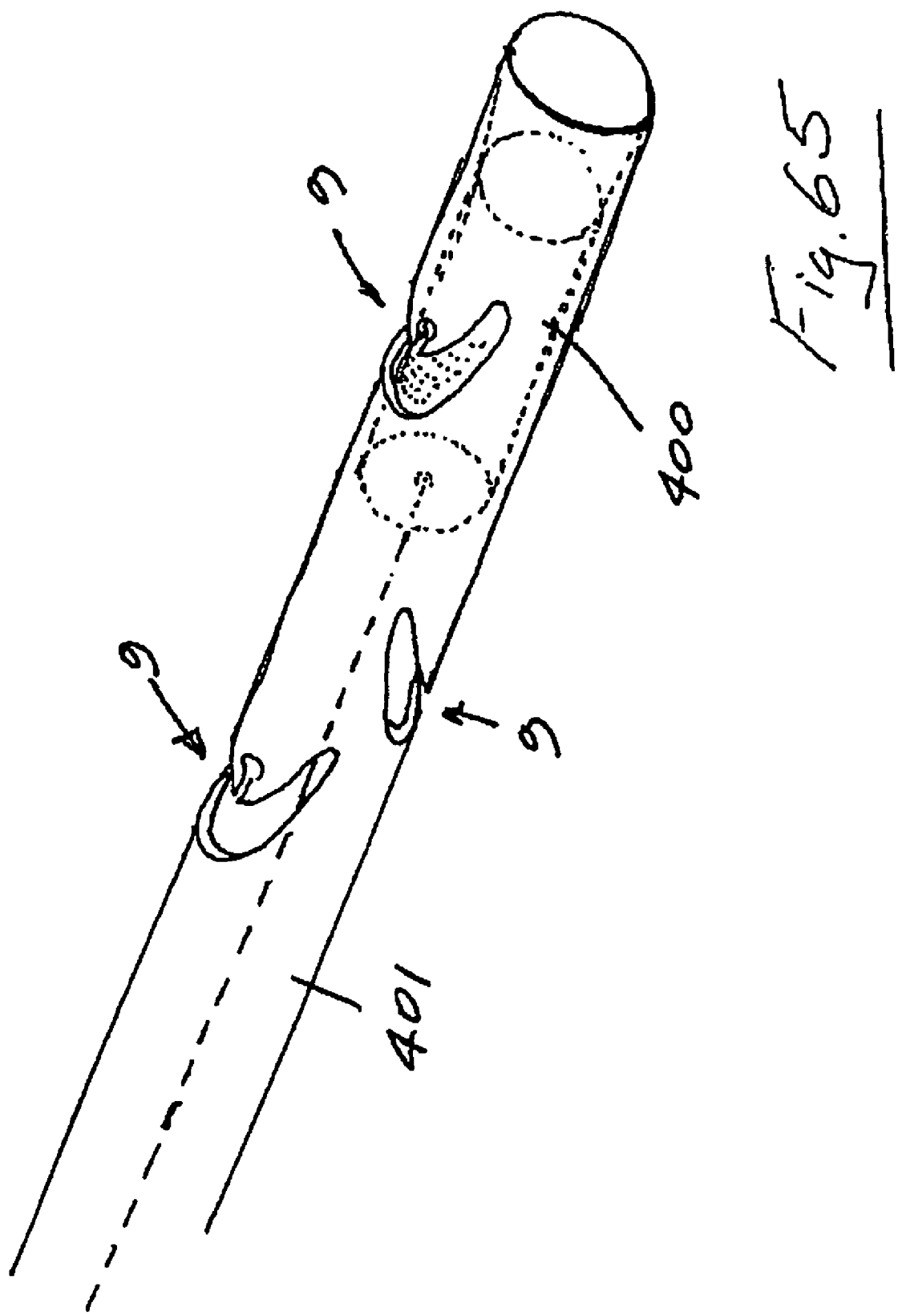
FIG. 65 is an isometric view of a distal end of another vein stripping device of the invention.
Figure 66:
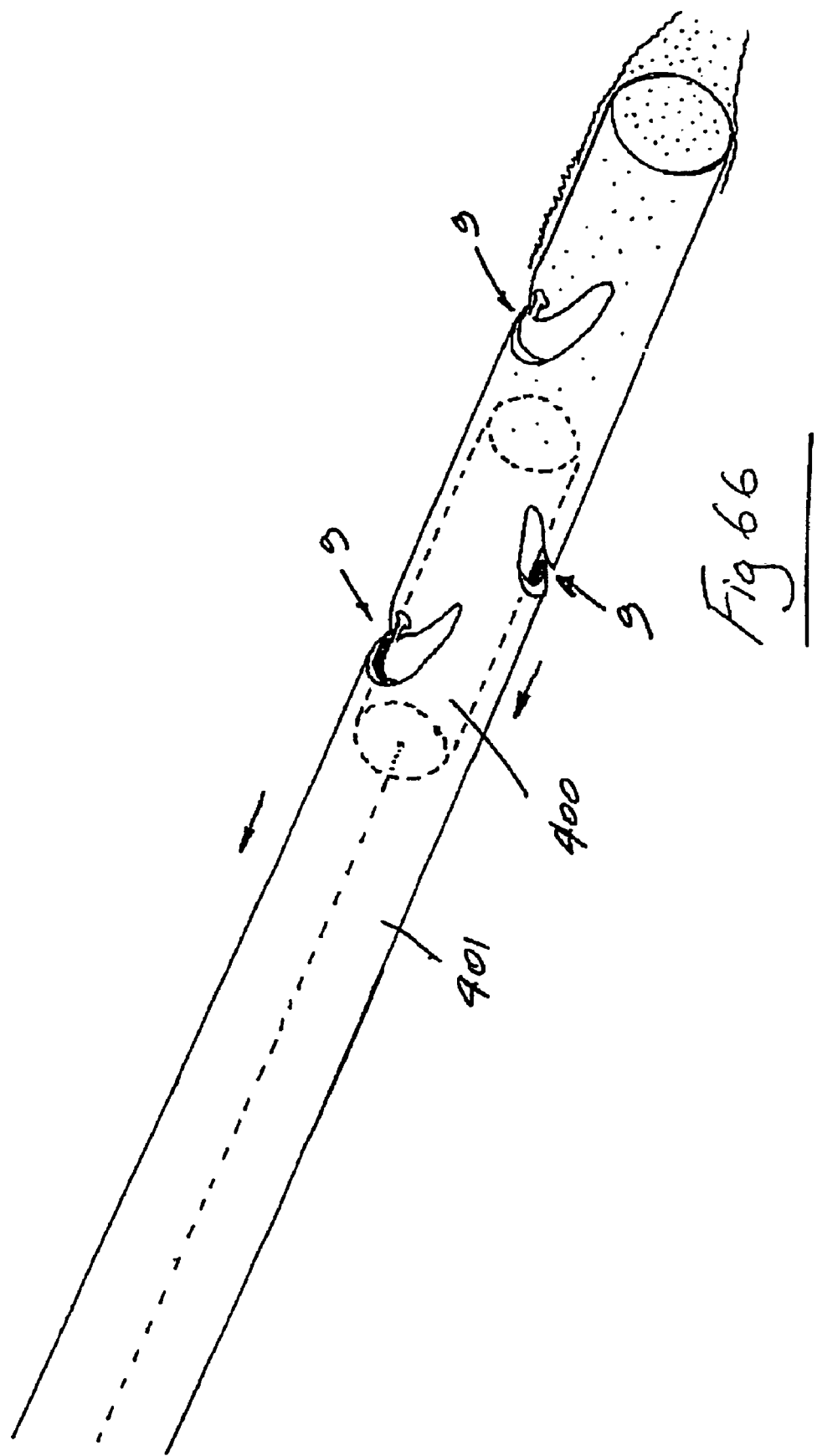
FIG. 66 is an isometric view of the device of FIG. 65, in use.

Referring to FIGS. 65 and 66 there is illustrated another vacuum generating means which in this case comprises a plunger 400 within a catheter 401. The plunger 400 extends longitudinally sufficient to occlude an entire grip feature so as to maintain a vacuum seal. The plunger 400 is pulled by a tension line to the proximal end of the catheter. As the plunger 400 retracts to the proximal end it sucks in blood in the vein and sucks the vein to attachment on the grip feature. In FIG. 66 the plunger 400 is shown occluding one or more grip features openings, drawing blood through the catheter and gripping the vein to the catheter.

Referring to FIGS. 73 to 77 there is illustrated another vein stripping device 500 according to the invention.

The vein stripping device 500 of the invention comprises a catheter 3 for insertion into a vein such as a saphenous vein 510 to be removed. The catheter has a proximal region adjacent a proximal end of the catheter and a distal region adjacent a distal end of the catheter. The catheter has a plurality of vein gripping means at least along the distal region for gripping a vein 510 to the catheter. In this case the catheter comprises an inner tube 512 and an outer tube 513 which are movable relative to one another. The inner tube 512 may be slidable relative to the outer tube 513.

Referring in particular to FIGS. 73 to 77 the inner tube 512 has a plurality of holes 515 and the outer tube 513 also has a plurality of holes 516. The tubes 512, 513 are movable relative to one another from an insertion configuration in which the holes 16 in the outer tube 513 are occluded by the inner tube 512 to a vein stripping configuration in which the holes 516 in the outer tube 513 are aligned with the holes 515 in the inner tube 512. The insertion configuration is illustrated for example in FIGS. 73 and 75 and the stripping configuration is illustrated for example in FIGS. 74 and 76.

A vein 510 is gripped by drawing it onto the outer holes 516. These holes 516 may have gripping features such as edges 525 which assist in gripping the vein around the holes 516.

The inner tube distal end in this case comprises a rounded soft distal tip 528 which may be for example of a suitable silicone material. Such a tip aids atraumatic passage of the catheter through a vein. The tip 528 defines a proximally facing land 529 against which a distal tip 530 of the outer tube 513 engages in the insertion configuration. When a vein 510 is gripped to the catheter the inner tube 512 and hence the distal tip 528 is drawn proximally and a vein 510 is gripped by the tip 530.

There may or may not be an inner tube 512. In cases where the device comprises an inner tube 512 it may extend beyond the outer tube 513 and expand to the same diameter as the outer tube 513. The vein 510 may be gripped where the inner and outer tube are pulled together at the tip.

A vacuum is in this case used to draw the vein 510 against the outer tube wall 513 when the device is in the stripping configuration. Blood is also drawn out of the vein 513 at this stage. Blood may be drawn from the vein 510 as the device is being inserted into the vein 510. The device is then pulled at the proximal end so that the vein 510 is detached at either the distal tip of the device or at some point further along the length of the vein 510. The vein 510 is gripped to the catheter substantially along the length thereof. Pulling the catheter back proximally pulls the vein 510 to detachment so that all of the vein 510 is removed, as illustrated and described above.

The device is hollow. This allows blood to pass through the device and to be evacuated from the vein 510 prior to detaching and removing the vein 510. It also improves the navigability of the device through the vein 510. A pointed tip can embed in the wall of the vein 510, because the pressure of the forward motion of the tip is concentrated at one point. In the invention there is a hollow tip which distributes the pressure of moving forward equally around the wall of the vein 510 and therefore will not be captured by a single feature inside the vein. The means of detaching the vein is achieved by gripping the vein substantially along its length along the device so that the entire vein can be pulled or drawn. The effect of this is that the vein 510 will fail at a point of weakness along its length beyond the tip of the device and further down the leg into the region of the calf. The result is that more of the vein may be removed than would be removed with conventional devices and this is a better outcome for the patient.

FIGS. 78 and 79 illustrate one mechanism that may be used to move the outer tube 513 relative to the inner tube 512 at the proximal end. A trigger type mechanism 535 is used to pull the outer tube 13 proximally relative to the inner tube 12. Another such mechanism is illustrated in FIGS. 80 and 81 which in this case utilises a thumb wheel 37.

Figure 82:
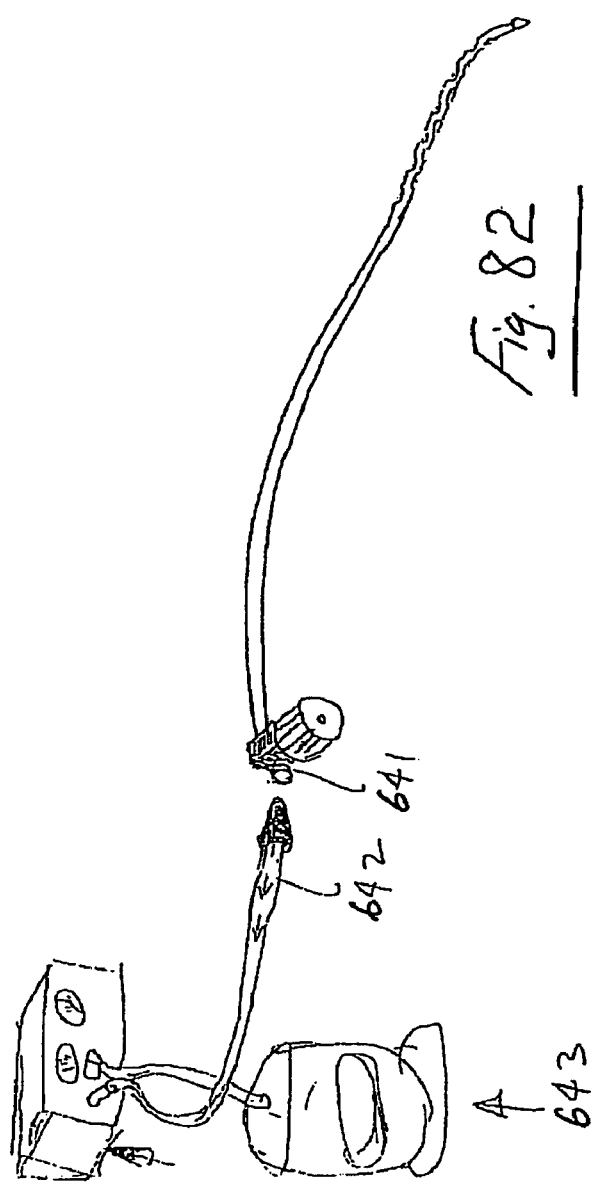
FIGS. 82 and 83 are isometric and partial cross sectional views illustrating one means of applying vacuum at a proximal end of the device.
Figure 83:
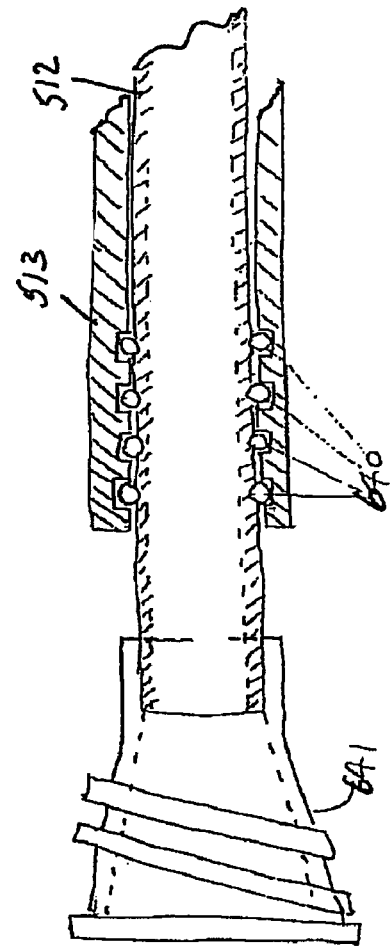
Figure 84:
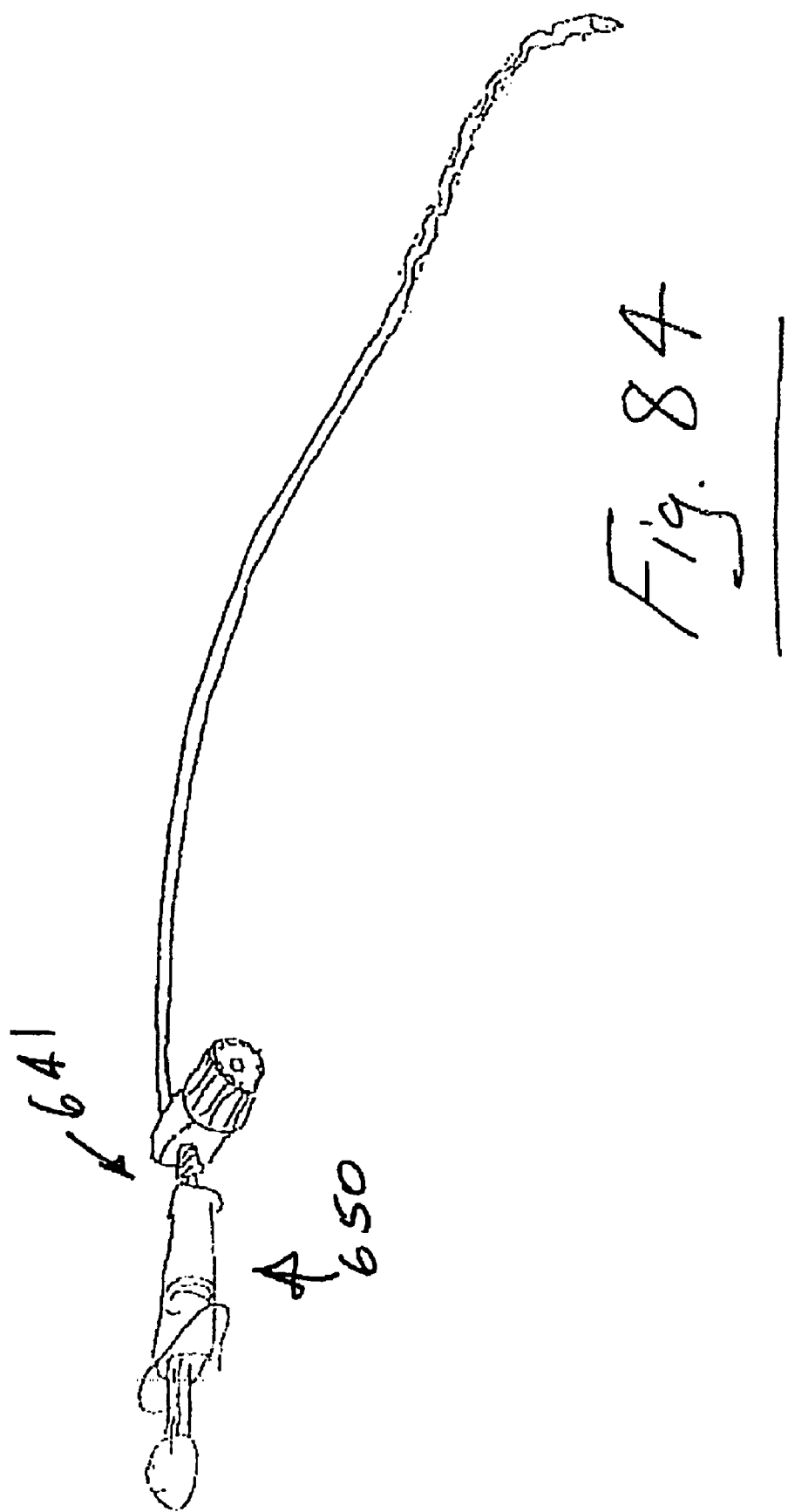
FIG. 84 is a perspective view of a device with an alternative vacuum generating system.

Referring to FIGS. 82 and 83 there is illustrated one means for applying a vacuum to draw a vein onto the outer tube holes 516. In this case there is a seal 640 between the inner and outer tubes 513, 512 at the proximal end. The inner tube 512 also has a standard leur type fitting 641 for attachment to a vacuum line 642 from a source 643 such as is available in a hospital operating theatre. As an alternative a syringe 650 may be used as illustrated in FIG. 84. The use of the syringe 650 requires the use of both hands to create the vacuum. The inverse syringe described above however requires only one hand.

In the invention the long saphenous vein is physically removed from the body and so cannot recannulise. A single incision is required. The incision is located in the region of the groin rather than just above the knee. This has cosmetic advantages. It also means that the saphenofemoral junction is surgically ligated and sutured. The ligation of the tributaries is also significant in preventing recanalisation.

In the invention post procedural pain is reduced or alleviated in a number of ways. Blood is suctioned and evacuated from the vein and the vein region prior to detachment and removal of the vein. Drug delivery may be targeted to the precise region of the vein channel. The procedure reduces the instances of inflammation and therefore the recovery time and the time to normal mobility by minimizing tissue injury. Tissue and nerve injury is minimised by the design of the tip and gripping means because the vein is suctioned into the device and away from surrounding tissue. It is designed to strip or peel the vein away from the adventitial layer.

The procedure prevents the vein from accumulating into a bulbous mass and from shredding. The device of the invention grips the vein substantially and along its length or along a length of between 2 cm and 5 cm. As the device is withdrawn the vein inverts over the length that is gripped and peels away from the attaching membrane thus avoiding nerve injury.

The procedure can be referred to as Endovenous Upward Perforate Invaginate Stripping.

The device enables suction to be applied to evacuate the vein on to the body of the catheter. The catheter has features designed to grip the vein when it is evacuated or suctioned onto the side of the catheter. The gripping features may include a micro channel through which a tumescent anaesthetic can pass through to the outer cell membrane of the vein wall.

The distal tip of the catheter may be constructed from a compliant and resilient material such as silicone. A hollow lumen tip of constant outer diameter with tapering wall thickness toward the front has the advantage that blood can pass through and it also navigates forward without causing injury. Injury is minimised because the pressure of the vein wall on the tip moving forward distally is equally and radially distributed around the tip. Pointed or narrow features may snag in the internal vein topology especially where tributaries are connected.

Additional suction can be created, manually, by using a standard medical injection syringe attached to the catheter. Such a syringe may also be used to administer a tumescent anaesthetic into the device, whereby tumescent anaesthetic may seep through the punctured walls of the vein through microfluidic channels in the gripping features.

The pharmacology may be injected into the guiding lumen after the device has been withdrawn with the vein attached, over the guiding lumen. This directs the pharmacology directly to the channel from where the vein came from.

Referring to FIGS. 36 to 41 the catheter may have a range of profiles. It may be oval in cross-sectional profile. This oval profile may continue in a straight line along the length of the lumen. Alternatively, the oval profile may rotate through 360° along the length of the lumen along various lengths of the lumen so that it creates a helical or spiral shape. The grip features may be located on the acute edges for greater mechanical strength and effectiveness.

Alternatively the outer lumen may have a lumen which is triangular in cross-sectional profile. This triangular profile may continue in a straight line along the length of the lumen. This triangular the profile may rotate through 360° along the length of the lumen along various lengths of the lumen so that it creates a spiral shape. Other non-circular profiles may also be used such as a rectangle or a square. Such non-circular profiles serve to provide better mechanical support for features embedded along the length of the lumen. The grip features may be located on the acute edges for greater effect.

The gripping features may be sharp pointed features which can grip into the blood vessel when it is forced over it. This feature may have micro channel which allows dissipation of a drug or fluid through the wall of the blood vessel where it has been penetrated by the gripping feature.

The source of the force which will pull the blood vessel over the pointed feature will be a negative pressure or a vacuum that is created within the lumen. The area adjacent to the pointed feature will create sufficient exposure to the vacuum to enable the wall of the blood vessel to be drawn over the pointed gripping feature. The gripping features may be located along the acute edge of any suitable profile.

The procedure will be quick to perform, it generally takes about 45 mins including preparation procedures such as tributary ligation.

Anaesthetic for the patient undergoing a vein stripping procedure may be general, epidural or spinal (local)

In the invention the vein is gripped along a specific length of the vein so that the pulling force is distributed along the length of the vein. The device removes blood from the vein. The guiding means may also remove blood from the region of the vein after the vein is removed. In removing blood the device is removing a source of irritation and inflammation which hinders post procedural recovery. The device can be used to administer a pharmaceutical targeted precisely to the region of the vein channel. The device may have a syringe attached to it at the proximal end. The syringe may be used to evacuate blood from any or all of the lumen inserted into the vein. The same or a different syringe may be used to administer a drug through the inner lumen to a targeted region precisely where it is required. The device can be used to remove all of the severed vein in a single operation.

A principal function of the device is to create a vacuum or negative pressure within the lumen to which the vein is evacuated and gripped. Negative pressure sucks the blood content of the vein through the lumen and into the syringe. This negative pressure or suction grips the inner surface of the vein to the device. The negative pressure may be created by a piston which can be integrated into the proximal handle, moving within a chamber integrated in the distal handle design.

The suction of the inner surface of the vein into the distal end enables the vein to be severed safely without any risk of damage to surrounding nerves. The vein will fail under tensile load at its weakest point below the tip.

The suction or negative pressure removes the blood from the vein and the surrounding tributaries and thereby reduces the cause of the irritation and inflammation in the limb tissue once the vein is removed.

The proximal end of the device consists of a handle made up of two parts which is used to control the tip elements and a syringe type device. The syringe creates a vacuum through a pushing motion rather than the pulling motion as in conventional syringes. A conventional syringe may be attached to the handle to evacuate the vein and to grip the vein through suction for the purpose of removing the vein.

The suction feature which grips the vein has the effect that one size of device can be used to remove all vein sizes.

Many or all components of the device may be made from metal or a suitable polymer. PolyEtherEtherKetone (PEEK) as high density polyethylene (HDPE) are polymers with characteristics that are particularly suited to the fabrication of the lumen required for this device. An improved form of this polymer consists of a modifier which delays kinking of the lumen through an excessive bending force. The mechanical performance of this polymer may be improved where in the mass index of the material is reduced and the mechanical strength and hardness is increased. This is achieved by heating the polymer to the melt index of the material.

The device can consist of two or more suction or evacuation mechanisms for the evacuation of blood and to grip the vein to the device. One evacuation mechanism may be integrated into the device design, which enables a vacuum to be pulled at the distal tip of the device while a pushing motion is delivered at the proximal end. Thus one hand can be used to apply the vacuum. The device may have a means of attaching a syringe through which further suction can be applied to grip the vein; blood can be extracted from the region of the removed vein; and/or a drug can be administered to a precise the target region along the path of where the vein was removed from.

Drug can be administered through a lumen which serves as a guiding means for the device. This lumen may contain a drug to be administered sealed within it. The drug is released when a syringe type device applies pressure which causes sealing membranes along the side of the device to fail mechanically and release the drug into the vein channel. Alternatively the membranes may be peeled away along the side of the lumen.

The guiding lumen ensures that a re-entry procedure to remove a partially remaining vein, that the device travels along the precise path of the vein and does not wander randomly into muscle tissue. This guiding lumen also provides for accurate and precise targeting of pharmaceuticals and drug delivery to the site of the removed vein.

Vein Grip Function

In the invention a vein is gripped internally sufficiently that the vein can be pulled. It may be sufficient to strip the subadventitial layers of the vein. The vein is stripped by means of grip features. This may be assisted by a vacuum or suction. Grip features may be internal or external to the device. Both of those functions can use the internal and external lumen.

Figure 67:
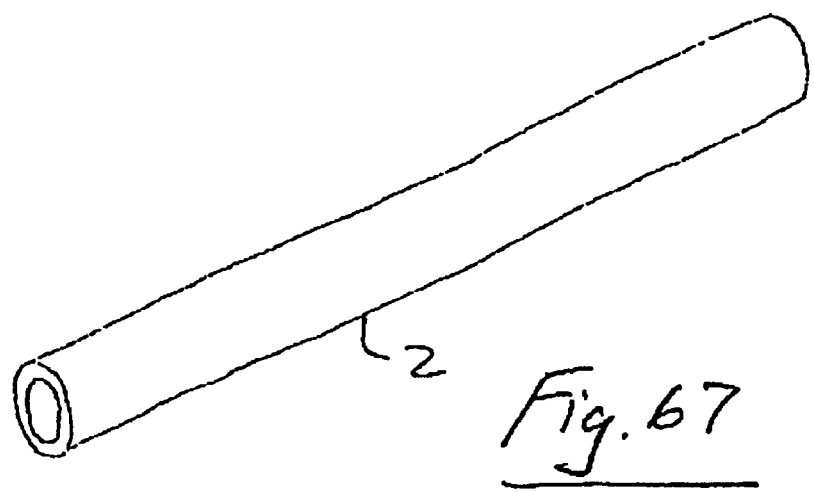
FIGS. 67 to 72 are isometric views of part of outer catheters used in the device of the invention.

The lumens of the device may be defined by elements which are not necessarily circular. For example, referring to FIG. 67 the lumen may be of oval shape. The advantage of this profile is that it has good strength on the acute edge for the location of a gripping feature.

Figure 68:
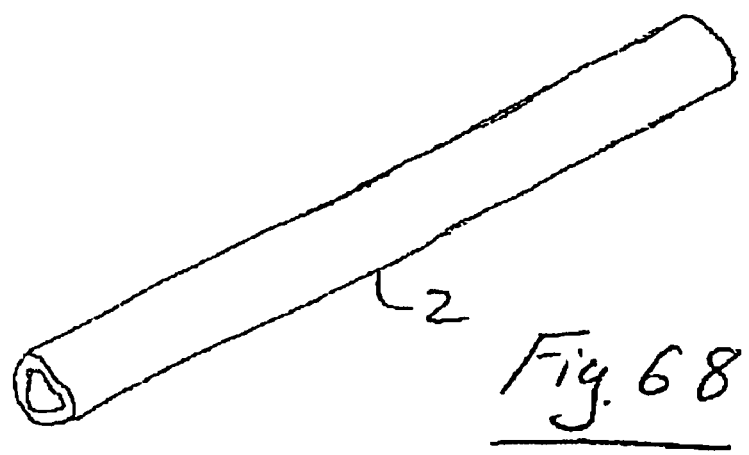

FIG. 68 shows a triangular profile with rounded or filleted edges for the outer lumen. The advantage of this profile is the higher strength allowing the acute edges for the location of gripping features.

Figure 69:
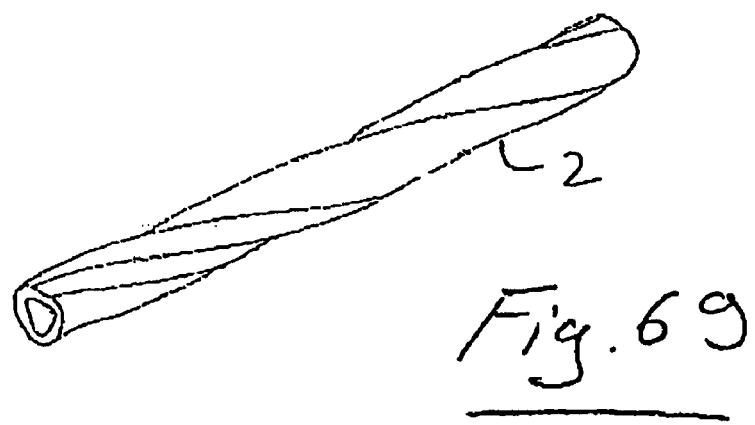

FIG. 69 shows the triangular profile role catered over the length of the lumen to form a helix spiral. This provides acute edges for a better distribution of gripping features.

Figure 70:
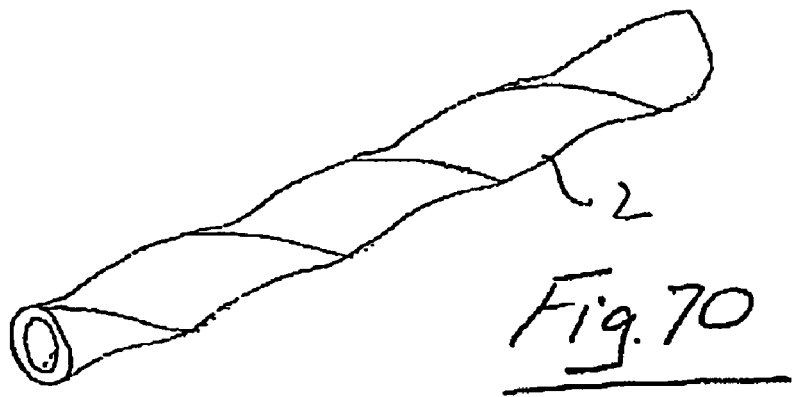
Figure 71:
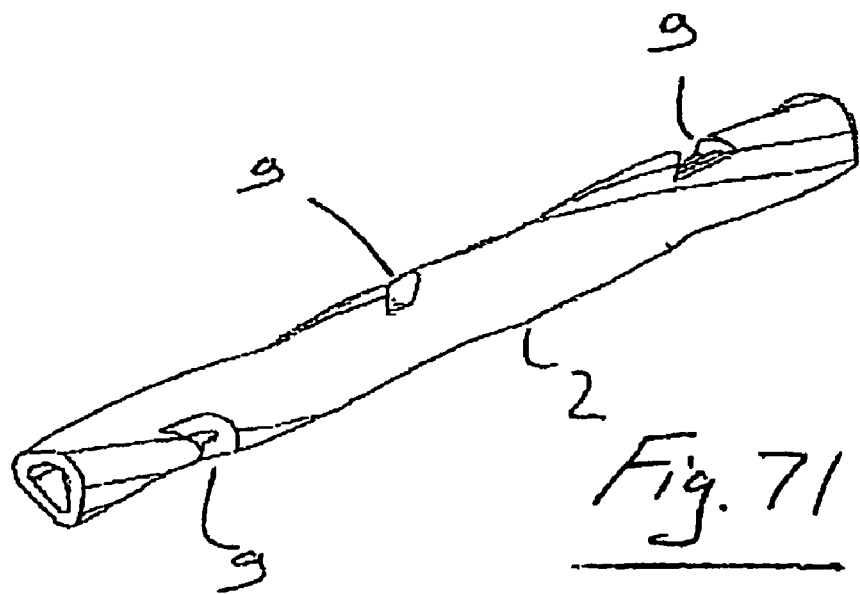
Figure 72:
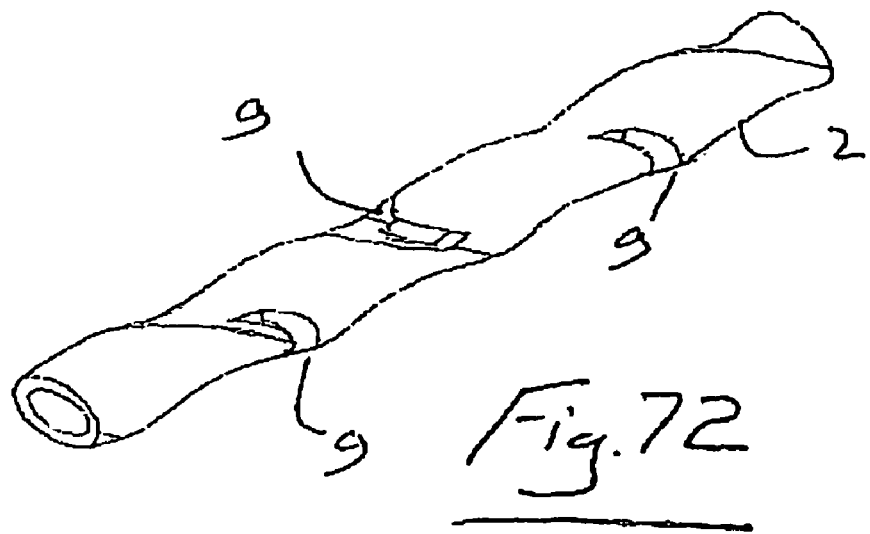
Figure 75:
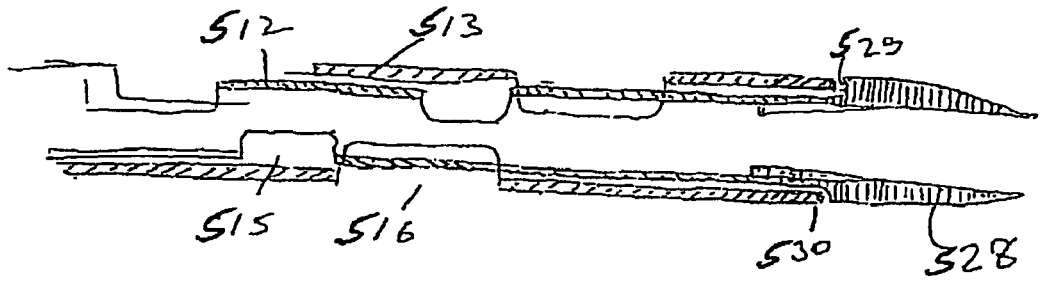
FIGS. 75 to 77 are cross sectional views illustrating the distal end of the device of FIG. 73 in various positions of use.
Figure 76:
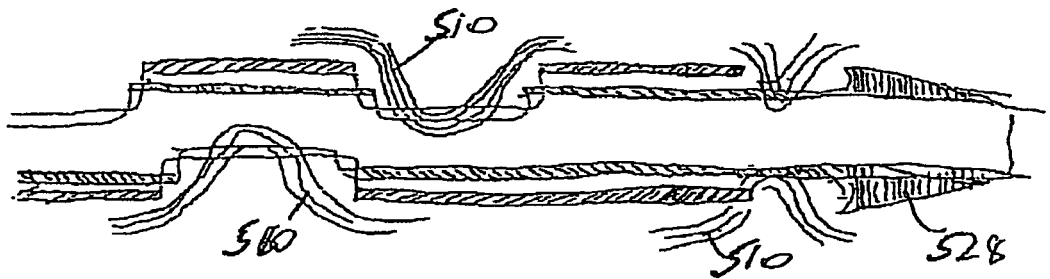
Figure 77:
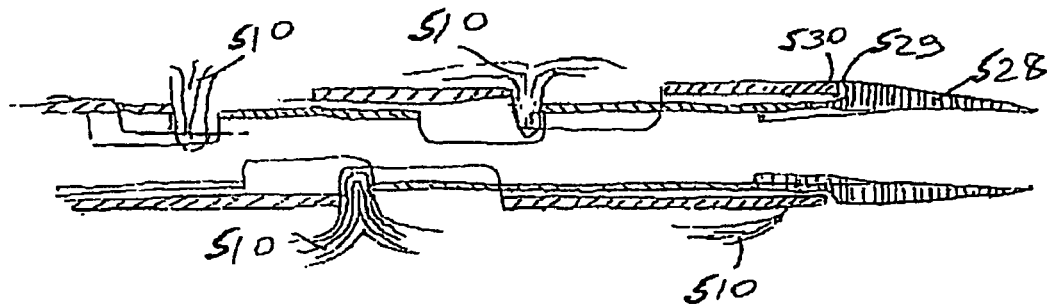

FIG. 70 shows the oval profile rotated through 260° along length of the outer lumen to represent a helix spiral. This rotating acute edge is more favorable for the distribution of gripping features.

It will be appreciated that the various features illustrated and/or described may be used as appropriate with any of the embodiments described and/or illustrated.

The invention is not limited to the embodiments hereinbefore described which may be varied in detail.

The invention claimed is:

1. A vein stripping device comprising a catheter for insertion into a vein to be removed, the catheter having a proximal region adjacent a proximal end of the catheter and a distal region adjacent a distal end of the catheter, the catheter having a plurality of vein grippers at least along the distal region of the catheter, the vein grippers comprising a plurality of holes in the wall of the catheter, the catheter being open at the distal end thereof for passage of blood through the catheter from the distal end;

wherein the device further comprises:
a proximal tube connected to the proximal region of the catheter;
a blood collecting housing, the proximal tube extending through the blood collecting housing;
a plunger which is movable through the housing to generate a vacuum in the catheter for drawing blood through the catheter from the distal end; and
a plunger tube connected to and extending proximally of the plunger, the plunger tube having an opening through which blood from the proximal tube passes into the chamber proximally of the plunger.

2. The vein stripping device as claimed in claim 1 wherein the catheter comprises an outer tubular member and an inner tubular member which extends through at least the distal region of the catheter.

3. The vein stripping device as claimed in claim 2 wherein the catheter comprises a support rib extending between the inner tubular member and the outer tubular member.

4. The vein stripping device as claimed in claim 3 wherein the support rib divides the lumen between the inner and outer tubular members into separate chambers.

5. The vein stripping device as claimed in claim 3 wherein the vein grippers extend on either side of a rib.

6. The vein stripping device as claimed in claim 5 wherein the rib is cut-away inwardly in the region of the vein gripper.

7. The vein stripping device as claimed in claim 2 wherein the support rib comprises a plurality of ribs extending between the inner and outer tubular members.

8. The vein stripping device as claimed in claim 2 wherein the distal end of the inner tubular member is stepped back from the distal end of the outer tubular member.

9. The vein stripping device as claimed in claim 2 comprising a guide over which the inner tubular member travels.

10. The vein stripping device as claimed in claim 9 wherein the outer tubular member has an exit port for the guide.

11. The vein stripping device as claimed in claim 10 wherein the exit port is distal of the proximal end of the catheter.

12. The vein stripping device as claimed in claim 11 wherein the inner tubular member extends to the exit port.

13. The vein stripping device as claimed in claim 9 wherein the guide comprises a guidewire.

14. The vein stripping device as claimed in claim 9 wherein the guide is hollow.

15. The vein stripping device as claimed in claim 14 wherein the guide contains an anaesthetic and/or a pharmaceutical.

16. The vein stripping device as claimed in claim 1 wherein the distal end of the catheter is distally tapered.

17. The vein stripping device as claimed in claim 16 wherein the device comprises an inner tubular member which extends to the distal end of the catheter.

18. The vein stripping device as claimed in claim 17 wherein the device comprises a support rib between the inner tubular member and the outer tubular member and the rib means is distally tapered.

19. The vein stripping device as claimed in claim 1 wherein the outer diameter of the distal region of the catheter is uniform.

20. The vein stripping device as claimed in claim 1 wherein the wall thickness of the catheter is distally tapered at the distal end thereof.

21. The vein stripping device as claimed in claim 1 wherein the vein grippers do not extend radially outwardly of the outer circumference of the catheter.

22. The vein stripping device as claimed in claim 1 wherein the vein grippers comprise an engager for engagement with a vein wall.

23. The vein stripping device as claimed in claim 22 wherein the vein engager comprises jaws for engagement with a vein.

24. The vein stripping device as claimed in claim 23 wherein the jaws are adapted to engage with a vein in response to movement of the catheter in the proximal direction.

25. The vein stripping device as claimed in claim 23 wherein the jaws define an entry slot for engagement with a vein.

26. The vein stripping device as claimed in claim 25 wherein the entry slot faces towards the proximal end of the catheter.

27. The vein stripping device as claimed in claim 23 wherein the jaws are biased towards a vein engagement configuration.

28. The vein stripping device as claimed in claim 22 wherein the vein grippers are movable in response to a vacuum being applied to at least the distal region of the catheter.

29. The vein stripping device as claimed in claim 22 wherein the vein grippers are pivotally movable relative to the catheter.

30. The vein stripping device as claimed in claim 1 wherein the vein grippers are movable.

31. The vein stripping device as claimed in claim 1 wherein the vein grippers are integral with the catheter.

32. The vein stripping device as claimed in claim 1 comprising a vacuum generator for drawing a vein into the vein grippers.

33. The vein stripping device as claimed in claim 32 wherein the vacuum generator for drawing a vein into the vein grippers is the same as the vacuum generator for drawing blood through the catheter.

34. The vein stripping device as claimed in claim 1 wherein the plunger has a handle for drawing the plunger through the chamber.

35. The vein stripping device as claimed in claim 34 wherein the handle is movable proximally to draw a vacuum.

36. The vein stripping device as claimed in claim 1 comprising a non return valve means for venting of the catheter.

37. The vein stripping device as claimed in claim 1, the catheter comprising an outer tube and an inner tube, the inner tube being movable relative to the inner tube.

\* \* \* \* \*